United States Patent
Bonutti et al.

(10) Patent No.: US 10,368,924 B2
(45) Date of Patent: Aug. 6, 2019

(54) METHODS AND DEVICES FOR TRAUMA WELDING

(71) Applicant: P Tech, LLC, Effingham, IL (US)

(72) Inventors: Peter M. Bonutti, Manalapan, FL (US); Matthew J. Cremens, Effingham, IL (US); Justin E. Beyers, Effingham, IL (US)

(73) Assignee: P Tech, LLC, Effingham, IL (US)

( * ) Notice: Subject to any disclaimer, the term of this patent is extended or adjusted under 35 U.S.C. 154(b) by 0 days.

(21) Appl. No.: 15/656,425

(22) Filed: Jul. 21, 2017

(65) Prior Publication Data

US 2017/0333094 A1 Nov. 23, 2017

Related U.S. Application Data

(63) Continuation of application No. 14/867,621, filed on Sep. 28, 2015, now Pat. No. 9,743,963, which is a
(Continued)

(51) Int. Cl.
*A61F 2/46* (2006.01)
*A61B 17/00* (2006.01)
(Continued)

(52) U.S. Cl.
CPC ...... *A61B 17/7233* (2013.01); *A61B 17/0401* (2013.01); *A61B 17/686* (2013.01);
(Continued)

(58) Field of Classification Search
CPC ........... A61F 2002/30065; A61B 17/80; A61B 17/86; A61B 2017/00504
See application file for complete search history.

(56) References Cited

U.S. PATENT DOCUMENTS

| 319,296 A | 6/1885 | Molesworth |
| 668,878 A | 2/1901 | Jensen |

(Continued)

FOREIGN PATENT DOCUMENTS

| CA | 2641580 | 8/2007 |
| CA | 2680827 | 9/2008 |

(Continued)

OTHER PUBLICATIONS

The Search for the Holy Grail: A Century of Anterior Cruciate Ligament Reconstruction, R. John Naranja, American Journal of Orthopedics, Nov. 1997.
(Continued)

*Primary Examiner* — David W Bates
(74) *Attorney, Agent, or Firm* — Stinson LLP

(57) ABSTRACT

The present invention provides a method for stabilizing a fractured bone. The method includes positioning an elongate rod in the medullary canal of the fractured bone and forming a passageway through the cortex of the bone. The passageway extends from the exterior surface of the bone to the medullary canal of the bone. The method also includes creating a bonding region on the elongate rod. The bonding region is generally aligned with the passageway of the cortex. Furthermore, the method includes positioning a fastener in the passageway of the cortex and on the bonding region of the elongate rod and thermally bonding the fastener to the bonding region of the elongate rod while the fastener is positioned in the passageway of the cortex.

11 Claims, 33 Drawing Sheets

Related U.S. Application Data continuation of application No. 13/149,038, filed on May 31, 2011, now Pat. No. 9,173,650, which is a continuation of application No. 11/416,618, filed on May 3, 2006, now Pat. No. 7,967,820.

(51) Int. Cl.

| | | |
|---|---|---|
| *A61B 17/68* | (2006.01) | |
| *A61B 17/80* | (2006.01) | |
| *A61F 2/40* | (2006.01) | |
| *A61B 17/04* | (2006.01) | |
| *A61B 17/70* | (2006.01) | |
| *A61B 17/72* | (2006.01) | |
| *A61B 17/86* | (2006.01) | |
| *A61B 17/88* | (2006.01) | |
| *A61B 17/82* | (2006.01) | |
| *G06F 21/10* | (2013.01) | |
| *A61F 2/28* | (2006.01) | |
| *A61F 2/30* | (2006.01) | |
| *A61F 2/32* | (2006.01) | |
| *A61F 2/34* | (2006.01) | |
| *A61F 2/36* | (2006.01) | |
| *A61F 2/38* | (2006.01) | |
| *A61F 2/42* | (2006.01) | |
| *A61F 2/44* | (2006.01) | |
| *A61F 2/82* | (2013.01) | |
| *A61B 17/11* | (2006.01) | |
| *A61B 17/17* | (2006.01) | |
| *A61B 17/32* | (2006.01) | |

(52) U.S. Cl.
CPC ...... *A61B 17/7032* (2013.01); *A61B 17/7058* (2013.01); *A61B 17/7059* (2013.01); *A61B 17/7062* (2013.01); *A61B 17/72* (2013.01); *A61B 17/725* (2013.01); *A61B 17/80* (2013.01); *A61B 17/8033* (2013.01); *A61B 17/82* (2013.01); *A61B 17/866* (2013.01); *A61B 17/88* (2013.01); *A61B 17/8863* (2013.01); *A61F 2/4081* (2013.01); *G06F 21/10* (2013.01); *A61B 17/11* (2013.01); *A61B 17/1128* (2013.01); *A61B 17/1146* (2013.01); *A61B 17/1721* (2013.01); *A61B 17/1742* (2013.01); *A61B 17/320068* (2013.01); *A61B 17/8038* (2013.01); *A61B 17/8685* (2013.01); *A61B 2017/00004* (2013.01); *A61B 2017/00504* (2013.01); *A61B 2017/044* (2013.01); *A61B 2017/0409* (2013.01); *A61B 2017/8655* (2013.01); *A61F 2/30756* (2013.01); *A61F 2/32* (2013.01); *A61F 2/3603* (2013.01); *A61F 2/38* (2013.01); *A61F 2/3804* (2013.01); *A61F 2/389* (2013.01); *A61F 2/3859* (2013.01); *A61F 2/40* (2013.01); *A61F 2/4202* (2013.01); *A61F 2/4455* (2013.01); *A61F 2/468* (2013.01); *A61F 2002/2817* (2013.01); *A61F 2002/30062* (2013.01); *A61F 2002/30065* (2013.01); *A61F 2002/3068* (2013.01); *A61F 2002/30133* (2013.01); *A61F 2002/30451* (2013.01); *A61F 2002/30604* (2013.01); *A61F 2002/30677* (2013.01); *A61F 2002/30785* (2013.01); *A61F 2002/30787* (2013.01); *A61F 2002/30878* (2013.01); *A61F 2002/30892* (2013.01); *A61F 2002/30894* (2013.01); *A61F 2002/30971* (2013.01); *A61F 2002/30973* (2013.01); *A61F 2002/3401* (2013.01); *A61F 2002/3403* (2013.01); *A61F 2002/444* (2013.01); *A61F 2002/828* (2013.01); *A61F 2210/0004* (2013.01); *A61F 2210/0071* (2013.01); *A61F 2220/0058* (2013.01); *A61F 2230/0015* (2013.01); *A61F 2250/0068* (2013.01); *A61F 2310/00011* (2013.01); *A61F 2310/00365* (2013.01); *A61F 2310/00383* (2013.01); *G06F 2221/0773* (2013.01); *G06F 2221/2137* (2013.01)

(56) References Cited

U.S. PATENT DOCUMENTS

| | | |
|---|---|---|
| 668,879 A | 2/1901 | Miller |
| 702,789 A | 6/1902 | Gibson |
| 862,712 A | 8/1907 | Collins |
| 2,121,193 A | 12/1932 | Hanicke |
| 2,187,852 A | 8/1936 | Friddle |
| 2,178,840 A | 11/1936 | Lorenian |
| 2,199,025 A | 4/1940 | Conn |
| 2,235,419 A | 3/1941 | Callahan |
| 2,248,054 A | 7/1941 | Becker |
| 2,270,188 A | 1/1942 | Longfellow |
| 2,518,276 A | 8/1950 | Braward |
| 2,557,669 A | 6/1951 | Lloyd |
| 2,566,499 A | 9/1951 | Richter |
| 2,621,653 A | 12/1952 | Briggs |
| 2,725,053 A | 11/1955 | Bambara |
| 2,830,587 A | 4/1958 | Everett |
| 3,347,234 A | 10/1967 | Voss |
| 3,367,809 A | 2/1968 | Soloff |
| 3,391,690 A | 7/1968 | Armao |
| 3,477,429 A | 11/1969 | Sampson |
| 3,513,848 A | 5/1970 | Winston |
| 3,577,991 A | 5/1971 | Wilkinson |
| 3,596,292 A | 8/1971 | Erb |
| 3,608,539 A | 9/1971 | Miller |
| 3,625,220 A | 12/1971 | Engelsher |
| 3,648,705 A | 3/1972 | Lary |
| 3,656,476 A | 4/1972 | Swinney |
| 3,657,056 A | 4/1972 | Winston |
| 3,678,980 A | 7/1972 | Gutshall |
| 3,709,218 A | 1/1973 | Halloran |
| 3,711,347 A | 1/1973 | Waner |
| 3,788,318 A | 1/1974 | Kim |
| 3,789,852 A | 2/1974 | Kim |
| 3,802,438 A | 4/1974 | Wolvek |
| 3,807,394 A | 4/1974 | Attenborough |
| 3,809,075 A | 5/1974 | Matles |
| 3,811,449 A | 5/1974 | Gravlee |
| 3,825,010 A | 7/1974 | McDonald |
| 3,833,003 A | 9/1974 | Taricco |
| 3,835,849 A | 9/1974 | McGuire |
| 3,842,824 A | 10/1974 | Neufeld |
| 3,857,396 A | 12/1974 | Hardwick |
| 3,867,932 A | 2/1975 | Huene |
| 3,875,652 A | 4/1975 | Arnold |
| 3,898,992 A | 8/1975 | Balamuth |
| 3,918,442 A | 11/1975 | Nikolaev |
| 3,968,800 A | 7/1976 | Vilasi |
| 4,064,566 A | 12/1977 | Fletcher |
| 4,089,071 A | 5/1978 | Kainberz |
| 4,156,574 A | 5/1979 | Boben |
| 4,164,794 A * | 8/1979 | Spector ............... A61C 8/0012 427/195 |
| 4,171,544 A | 10/1979 | Hench |
| 4,183,102 A | 1/1980 | Guiset |
| 4,199,864 A | 4/1980 | Ashman |
| 4,200,939 A | 5/1980 | Oser |
| 4,210,148 A | 7/1980 | Stivala |
| 4,213,816 A | 7/1980 | Morris |
| 4,234,425 A | 11/1980 | Leo |
| 4,235,233 A | 11/1980 | Mouwen |
| 4,235,238 A | 11/1980 | Ogiu |
| 4,257,411 A | 3/1981 | Cho |
| 4,265,231 A | 5/1981 | Scheller, Jr. |
| 4,281,649 A | 8/1981 | Derweduwen |
| 4,309,488 A | 1/1982 | Heide |
| 4,320,762 A | 3/1982 | Bentov |

(56) References Cited

U.S. PATENT DOCUMENTS

| | | |
|---|---|---|
| 4,351,069 A | 9/1982 | Ballintyn |
| 4,364,381 A | 12/1982 | Sher |
| 4,365,356 A | 12/1982 | Broemer |
| 4,388,921 A | 6/1983 | Sutter |
| 4,395,798 A | 8/1983 | McVey |
| 4,409,974 A | 10/1983 | Freedland |
| 4,414,166 A | 11/1983 | Charlson |
| 4,437,191 A | 3/1984 | Van der Zat |
| 4,437,362 A | 3/1984 | Hurst |
| 4,444,180 A | 4/1984 | Schneider |
| 4,448,194 A | 5/1984 | DiGiovanni |
| 4,456,005 A | 6/1984 | Lichty |
| 4,461,281 A | 7/1984 | Carson |
| 4,493,317 A | 1/1985 | Klaue |
| 4,495,664 A | 1/1985 | Blanquaert |
| 4,501,031 A | 2/1985 | McDaniel |
| 4,504,268 A | 3/1985 | Herlitze |
| 4,506,681 A | 3/1985 | Mundell |
| 4,514,125 A | 4/1985 | Stol |
| 4,526,173 A | 7/1985 | Sheehan |
| 4,535,772 A | 8/1985 | Sheehan |
| 4,547,327 A | 10/1985 | Bruins |
| 4,556,350 A | 12/1985 | Bernhardt |
| 4,566,138 A | 1/1986 | Lewis |
| 4,589,868 A | 5/1986 | Dretler |
| 4,590,928 A | 5/1986 | Hunt |
| 4,597,379 A | 7/1986 | Kihn |
| 4,599,085 A | 7/1986 | Riess |
| 4,601,893 A | 7/1986 | Cardinal |
| 4,606,335 A | 8/1986 | Wedeen |
| 4,621,640 A | 11/1986 | Mulhollan |
| 4,630,609 A | 12/1986 | Chin |
| 4,632,101 A | 12/1986 | Freedland |
| 4,645,503 A | 2/1987 | Lin |
| 4,657,460 A | 4/1987 | Bien |
| 4,659,268 A | 4/1987 | Del Mundo |
| 4,662,063 A | 5/1987 | Collins |
| 4,662,068 A | 5/1987 | Polonsky |
| 4,662,887 A | 5/1987 | Turner |
| 4,669,473 A | 6/1987 | Richards |
| 4,685,458 A | 8/1987 | Lackrone |
| 4,691,741 A | 9/1987 | Affa et al. |
| 4,705,040 A | 11/1987 | Mueller |
| 4,706,670 A | 11/1987 | Andersen |
| 4,708,139 A | 11/1987 | Dunbar, IV |
| 4,713,077 A | 12/1987 | Small |
| 4,716,901 A | 1/1988 | Jackson |
| 4,718,909 A | 1/1988 | Brown |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble |
| 4,739,751 A | 4/1988 | Sapega |
| 4,741,330 A | 5/1988 | Hayhurst |
| 4,749,585 A | 6/1988 | Greco |
| 4,750,492 A | 6/1988 | Jacobs |
| 4,768,507 A | 6/1988 | Fischell |
| 4,772,286 A | 9/1988 | Goble |
| 4,776,328 A | 10/1988 | Frey |
| 4,776,738 A | 10/1988 | Winston |
| 4,776,851 A | 10/1988 | Bruchman |
| 4,781,182 A | 11/1988 | Purnell |
| 4,790,303 A | 12/1988 | Steffee |
| 4,792,336 A | 12/1988 | Hiavacek |
| 4,817,591 A | 4/1989 | Klause |
| 4,822,224 A | 4/1989 | Carl |
| 4,823,794 A | 4/1989 | Pierce |
| 4,832,025 A | 5/1989 | COates |
| 4,832,026 A | 5/1989 | Jones |
| 4,834,752 A | 5/1989 | Van Kampen |
| 4,841,960 A | 6/1989 | Garner |
| 4,843,112 A | 6/1989 | Gerhart |
| 4,846,812 A | 7/1989 | Walker |
| 4,862,882 A | 9/1989 | Venturi |
| 4,869,242 A | 9/1989 | Galluzzo |
| 4,870,957 A | 10/1989 | Goble |
| 4,883,048 A | 11/1989 | Purnell |
| 4,890,612 A | 1/1990 | Kensey |
| 4,895,148 A | 1/1990 | Bays |
| 4,898,156 A | 2/1990 | Gatturna |
| 4,899,729 A | 2/1990 | Gill |
| 4,899,744 A | 2/1990 | Fujitsuka |
| 4,901,721 A | 2/1990 | Hakki |
| 4,921,479 A | 5/1990 | Grayzel |
| 4,922,897 A | 5/1990 | Sapega |
| 4,924,866 A | 5/1990 | Yoon |
| 4,932,960 A | 6/1990 | Green |
| 4,935,026 A | 6/1990 | McFadden |
| 4,935,028 A | 6/1990 | Drews |
| 4,945,625 A | 8/1990 | Winston |
| 4,954,126 A | 9/1990 | Wallsten |
| 4,957,498 A | 9/1990 | Caspari |
| 4,961,741 A | 10/1990 | Hayhurst |
| 4,963,151 A | 10/1990 | Kucheyne |
| 4,966,583 A | 10/1990 | Debbas |
| 4,968,315 A | 11/1990 | Gatturna |
| 4,969,888 A | 11/1990 | Scholten |
| 4,969,892 A | 11/1990 | Burton |
| 4,990,161 A | 2/1991 | Kampner |
| 4,994,071 A | 2/1991 | MacGrego |
| 4,997,445 A | 3/1991 | Hodorek |
| 4,998,539 A | 3/1991 | Delsanti |
| 5,002,550 A | 3/1991 | Li |
| 5,002,563 A | 3/1991 | Pyka |
| 5,009,652 A | 4/1991 | Morgan |
| 5,009,663 A | 4/1991 | Broome |
| 5,009,664 A | 4/1991 | Sievers |
| 5,013,316 A | 5/1991 | Goble |
| 5,019,090 A | 5/1991 | Pinchuk |
| 5,021,059 A | 6/1991 | Kensey |
| 5,035,713 A | 7/1991 | Friis |
| 5,037,404 A | 8/1991 | Gold |
| 5,037,422 A | 8/1991 | Hayhurst |
| 5,041,093 A | 8/1991 | Chu |
| 5,041,114 A | 8/1991 | Chapman |
| 5,041,129 A | 8/1991 | Hayhurst |
| 5,046,513 A | 9/1991 | Gatturna |
| 5,047,055 A | 9/1991 | Bao |
| 5,051,049 A | 9/1991 | Wills |
| 5,053,046 A | 10/1991 | Janese |
| 5,053,047 A | 10/1991 | Yoon |
| 5,059,193 A | 10/1991 | Kuslich |
| 5,059,206 A | 10/1991 | Winters |
| 5,061,274 A | 10/1991 | Kensey |
| 5,061,286 A | 10/1991 | Lyle |
| 5,069,674 A | 12/1991 | Fearnot |
| 5,078,731 A | 1/1992 | Hayhurst |
| 5,078,744 A | 1/1992 | Chvapil |
| 5,078,745 A | 1/1992 | Rhenter |
| 5,084,050 A | 1/1992 | Draenert |
| 5,084,051 A | 1/1992 | Tormala |
| 5,085,660 A | 2/1992 | Lin |
| 5,085,661 A | 2/1992 | Moss |
| 5,098,433 A | 3/1992 | Freedland |
| 5,098,434 A | 3/1992 | Serbousek |
| 5,098,436 A | 3/1992 | Ferrante |
| 5,100,405 A | 3/1992 | McLaren |
| 5,100,417 A | 3/1992 | Cerier |
| 5,102,417 A | 4/1992 | Palmaz |
| 5,102,421 A | 4/1992 | Anspach, Jr. |
| 5,108,399 A | 4/1992 | Eitenmuller |
| 5,120,175 A | 6/1992 | Arbegast |
| 5,123,520 A | 6/1992 | Schmid |
| 5,123,914 A | 6/1992 | Cope |
| 5,123,941 A | 6/1992 | Lauren |
| 5,133,732 A | 7/1992 | Wiktor |
| RE34,021 E | 8/1992 | Mueller |
| 5,141,520 A | 8/1992 | Goble |
| 5,147,362 A | 9/1992 | Goble |
| 5,154,720 A | 10/1992 | Trott |
| 5,156,613 A | 10/1992 | Sawyer |
| 5,156,616 A | 10/1992 | Meadows |
| 5,158,566 A | 10/1992 | Pianetti |
| 5,158,934 A | 10/1992 | Ammann |

(56) References Cited

U.S. PATENT DOCUMENTS

| | | |
|---|---|---|
| 5,163,960 A | 11/1992 | Bonutti |
| 5,171,251 A | 12/1992 | Bregen |
| 5,176,682 A | 1/1993 | Chow |
| 5,179,964 A | 1/1993 | Cook |
| 5,180,388 A | 1/1993 | DiCarlo |
| 5,183,464 A | 2/1993 | Dubrul |
| 5,192,287 A | 3/1993 | Fournier |
| 5,192,326 A | 3/1993 | Bao |
| 5,197,166 A | 3/1993 | Meier |
| 5,197,971 A | 3/1993 | Bonutti |
| 5,203,784 A | 4/1993 | Ross |
| 5,203,787 A | 4/1993 | Noblitt |
| 5,208,950 A | 5/1993 | Meritt |
| 5,209,776 A | 5/1993 | Bass |
| 5,217,493 A | 6/1993 | Raad |
| 5,219,359 A | 6/1993 | McQuilkin |
| 5,226,899 A | 7/1993 | Lee |
| 5,234,006 A | 8/1993 | Eaton |
| 5,236,438 A | 8/1993 | Wilk |
| 5,242,902 A | 9/1993 | Murphy |
| 5,248,313 A | 9/1993 | Greene |
| 5,254,113 A | 10/1993 | Wilk |
| 5,258,007 A | 11/1993 | Spetzler |
| 5,258,015 A | 11/1993 | Li |
| 5,258,016 A | 11/1993 | DiPoto |
| 5,266,325 A | 11/1993 | Kuzma |
| 5,269,783 A | 12/1993 | Sander |
| 5,269,785 A | 12/1993 | BOnutti |
| 5,269,809 A | 12/1993 | Hayhurst |
| 5,281,235 A | 1/1994 | Haber |
| 5,282,832 A | 2/1994 | Toso |
| 5,290,281 A | 3/1994 | Tschakaloff |
| 5,304,119 A | 4/1994 | Balaban |
| 5,306,280 A | 4/1994 | Bregen |
| 5,315,741 A | 5/1994 | Dubberke |
| 5,318,588 A | 6/1994 | Horzewski |
| 5,320,611 A | 6/1994 | Bonutti |
| 5,324,308 A | 6/1994 | Pierce |
| 5,328,480 A | 7/1994 | Melker |
| 5,329,846 A | 7/1994 | Bonutti |
| 5,329,924 A | 7/1994 | Bonutti |
| 5,330,468 A | 7/1994 | Burkhart |
| 5,330,476 A | 7/1994 | Hiot |
| 5,330,486 A | 7/1994 | Wilk |
| 5,336,231 A | 8/1994 | Adair |
| 5,339,799 A | 8/1994 | Kami |
| 5,349,956 A | 9/1994 | Bonutti |
| 5,352,229 A | 10/1994 | Goble |
| 5,354,298 A | 10/1994 | Lee |
| 5,354,302 A | 10/1994 | Ko |
| 5,366,480 A | 11/1994 | Corriveaau |
| 5,370,646 A | 12/1994 | Reese |
| 5,370,660 A | 12/1994 | Weinstein |
| 5,372,146 A | 12/1994 | Branch |
| 5,374,235 A | 12/1994 | Ahrens |
| 5,376,126 A | 12/1994 | Lin |
| 5,382,254 A | 1/1995 | McGarry |
| 5,383,883 A | 1/1995 | Wilk |
| 5,383,905 A | 1/1995 | Golds |
| 5,391,173 A | 2/1995 | Wilk |
| 5,395,308 A | 3/1995 | Fox |
| 5,400,805 A | 3/1995 | Warren |
| 5,403,312 A | 4/1995 | Yates |
| 5,403,348 A | 4/1995 | Bonutti |
| 5,405,359 A | 4/1995 | Pierce |
| 5,411,523 A | 5/1995 | Goble |
| 5,413,585 A | 5/1995 | Pagedas |
| 5,417,691 A | 5/1995 | Hayhurst |
| 5,417,701 A | 5/1995 | Holmes |
| 5,417,712 A | 5/1995 | Whittaker |
| 5,423,796 A | 6/1995 | Shikhman |
| 5,431,670 A | 7/1995 | Holmes |
| 5,439,470 A | 8/1995 | Li |
| 5,441,538 A | 8/1995 | Bonutti |
| 5,443,512 A | 8/1995 | Parr |
| 5,449,372 A | 9/1995 | Schmaltz |
| 5,449,382 A | 9/1995 | Dayton |
| 5,451,235 A | 9/1995 | Lock |
| 5,456,722 A | 10/1995 | McLeod |
| 5,458,653 A | 10/1995 | Davison |
| 5,462,561 A | 10/1995 | Voda |
| 5,464,424 A | 11/1995 | O'Donnell |
| 5,464,426 A | 11/1995 | Bonutti |
| 5,464,427 A | 11/1995 | Curtis |
| 5,472,444 A | 12/1995 | Huebner |
| 5,474,554 A | 12/1995 | Ku |
| 5,478,353 A | 12/1995 | Yoon |
| 5,479,351 A | 12/1995 | Meade |
| 5,480,403 A | 1/1996 | Lee |
| 5,486,197 A | 1/1996 | Le |
| 5,487,844 A | 1/1996 | Fujita |
| 5,488,958 A | 2/1996 | Topel |
| 5,496,292 A | 3/1996 | Burnham |
| 5,496,335 A | 3/1996 | Thomason |
| 5,496,348 A | 3/1996 | Bonutti |
| 5,501,700 A | 3/1996 | Hirata |
| 5,504,977 A | 4/1996 | Weppner |
| 5,505,735 A | 4/1996 | Li |
| 5,507,754 A | 4/1996 | Green |
| 5,522,844 A | 6/1996 | Johnson |
| 5,522,845 A | 6/1996 | Wenstrom, Jr. |
| 5,522,846 A | 6/1996 | Bonutti |
| 5,527,341 A | 6/1996 | Gogolewski |
| 5,527,342 A | 6/1996 | Pietrzak |
| 5,527,343 A | 6/1996 | Bonutti |
| 5,529,075 A | 6/1996 | Clark |
| 5,531,759 A | 7/1996 | Kensey |
| 5,534,012 A | 7/1996 | Bonutti |
| 5,534,028 A | 7/1996 | Bao |
| 5,540,718 A | 7/1996 | Barlett |
| 5,542,423 A | 8/1996 | Bonutti |
| 5,545,178 A | 8/1996 | Kensey |
| 5,545,180 A | 8/1996 | Le |
| 5,545,206 A | 8/1996 | Carson |
| 5,549,630 A | 8/1996 | Bonutti |
| 5,549,631 A | 8/1996 | Bonutti |
| 5,556,402 A | 9/1996 | Xu |
| 5,569,252 A | 10/1996 | Justin |
| 5,569,305 A | 10/1996 | Bonutti |
| 5,573,517 A | 11/1996 | Bonutti |
| 5,573,538 A | 11/1996 | Laboureau |
| 5,573,542 A | 11/1996 | Steveens |
| 5,584,835 A | 12/1996 | Greenfield |
| 5,584,860 A | 12/1996 | Goble |
| 5,584,862 A | 12/1996 | Bonutti |
| 5,591,206 A | 1/1997 | Moufarrege |
| 5,593,422 A | 1/1997 | Muijs Van De Moer |
| 5,593,425 A | 1/1997 | Bonutti |
| 5,593,625 A | 1/1997 | Riebel |
| 5,601,557 A | 2/1997 | Hayhurst |
| 5,601,558 A | 2/1997 | Torrie |
| 5,601,595 A | 2/1997 | Schwartz |
| 5,607,427 A | 3/1997 | Tschakaloff |
| 5,609,595 A | 3/1997 | Pennig |
| 5,618,314 A | 4/1997 | Harwin |
| 5,620,461 A | 4/1997 | Muijs Van De Moer |
| 5,626,612 A | 5/1997 | Barlett |
| 5,626,614 A | 5/1997 | Hart |
| 5,626,718 A | 5/1997 | Phillippe |
| 5,628,751 A | 5/1997 | Sander |
| 5,630,824 A | 5/1997 | Hart |
| 5,634,926 A | 6/1997 | Jobe |
| 5,643,274 A | 7/1997 | Sander |
| 5,643,293 A | 7/1997 | Kogasaka |
| 5,643,295 A | 7/1997 | Yoon |
| 5,643,321 A | 7/1997 | McDevitt |
| 5,645,553 A | 7/1997 | Kolesa |
| 5,645,597 A | 7/1997 | Krapiva |
| 5,645,599 A | 7/1997 | Samani |
| 5,649,955 A | 7/1997 | Hashimoto |
| 5,649,963 A | 7/1997 | McDevitt |
| 5,651,377 A | 7/1997 | O'Donnell |
| 5,658,313 A | 8/1997 | Thal |
| 5,660,225 A | 8/1997 | Saffran |

(56) References Cited

U.S. PATENT DOCUMENTS

| | | |
|---|---|---|
| 5,662,658 A | 9/1997 | Wenstrom, Jr. |
| 5,665,089 A | 9/1997 | Dall |
| 5,665,109 A | 9/1997 | Yoon |
| 5,667,513 A | 9/1997 | Torrie |
| 5,669,917 A | 9/1997 | Sauer |
| 5,674,240 A | 10/1997 | Bonutti |
| 5,681,310 A | 10/1997 | Yuan |
| 5,681,333 A | 10/1997 | Burkhart |
| 5,681,351 A | 10/1997 | Jamiolkowski |
| 5,681,352 A | 10/1997 | Clancy |
| 5,685,820 A | 11/1997 | Riek |
| 5,688,283 A | 11/1997 | Knapp |
| 5,690,654 A | 11/1997 | Ovil |
| 5,690,655 A | 11/1997 | Hart |
| 5,690,676 A | 11/1997 | DiPoto |
| 5,693,055 A | 12/1997 | Zahiri |
| 5,697,950 A | 12/1997 | Fucci |
| 5,702,397 A | 12/1997 | Gonle |
| 5,702,462 A | 12/1997 | Oberlander |
| 5,707,395 A | 1/1998 | Li |
| 5,713,903 A | 2/1998 | Sander |
| 5,713,921 A | 2/1998 | Bonutti |
| 5,718,717 A | 2/1998 | Bonutti |
| 5,720,747 A | 2/1998 | Burke |
| 5,720,753 A | 2/1998 | Sander |
| 5,725,541 A | 3/1998 | Anspach, III |
| 5,725,556 A | 3/1998 | Moser |
| 5,725,582 A | 3/1998 | Bevan |
| 5,730,747 A | 3/1998 | Ek |
| 5,733,306 A | 3/1998 | Bonutti |
| 5,735,875 A | 4/1998 | Bonutti |
| 5,735,877 A | 4/1998 | Pagedas |
| 5,735,899 A | 4/1998 | Schwartz |
| 5,741,282 A | 4/1998 | Anspach, III |
| 5,752,952 A | 5/1998 | Adamson |
| 5,752,974 A | 5/1998 | Rhee |
| 5,755,809 A | 5/1998 | Cohen |
| 5,762,458 A | 6/1998 | Wang |
| 5,766,221 A | 6/1998 | Benderev |
| 5,769,894 A | 6/1998 | Ferragamo |
| 5,772,672 A | 6/1998 | Toy |
| 5,776,151 A | 7/1998 | Chan |
| 5,779,706 A | 7/1998 | Tschakaloff |
| 5,782,862 A | 7/1998 | BOnutti |
| 5,785,713 A | 7/1998 | Jobe |
| 5,792,096 A | 8/1998 | Rentmeester |
| 5,797,931 A | 8/1998 | Bito |
| 5,800,537 A | 9/1998 | Bell |
| 5,807,403 A | 9/1998 | Beyar |
| 5,810,849 A | 9/1998 | Kontos |
| 5,810,853 A | 9/1998 | Yoon |
| 5,810,884 A | 9/1998 | Kim |
| 5,814,072 A | 9/1998 | BOnutti |
| 5,814,073 A | 9/1998 | Bonutti |
| 5,823,994 A | 10/1998 | Sharkey |
| 5,824,009 A | 10/1998 | Fukuda |
| 5,830,125 A | 11/1998 | Scribner |
| 5,836,897 A | 11/1998 | Sakural |
| 5,839,899 A | 11/1998 | Robinson |
| 5,843,178 A | 12/1998 | Vanney |
| 5,845,645 A | 12/1998 | Bonutti |
| 5,851,185 A | 12/1998 | Berns |
| 5,865,834 A | 2/1999 | McGuire |
| 5,866,634 A | 2/1999 | Tokushige |
| 5,868,749 A | 2/1999 | Reed |
| 5,874,235 A | 2/1999 | Chan et al. |
| 5,879,372 A | 3/1999 | Barlett |
| 5,891,166 A | 4/1999 | Schervinsky |
| 5,891,168 A | 4/1999 | Thal |
| 5,893,880 A | 4/1999 | Egan |
| 5,897,574 A | 4/1999 | Bonutti |
| 5,899,911 A | 5/1999 | Carter |
| 5,899,921 A | 5/1999 | Caspari |
| 5,906,579 A | 5/1999 | Vander Salm |
| 5,906,625 A | 5/1999 | Bito |
| 5,908,429 A | 6/1999 | Yoon |
| 5,911,721 A | 6/1999 | Nicholson |
| 5,918,604 A | 7/1999 | Whelan |
| 5,919,193 A | 7/1999 | Slavitt |
| 5,919,194 A | 7/1999 | Anderson |
| 5,919,208 A | 7/1999 | Valenti |
| 5,919,215 A | 7/1999 | Wilklund |
| 5,921,986 A | 7/1999 | Bonutti |
| 5,925,064 A | 7/1999 | Meyers |
| 5,928,244 A | 7/1999 | Tovey |
| 5,928,267 A | 7/1999 | Bonutti |
| 5,931,838 A | 8/1999 | Vito |
| 5,931,869 A | 8/1999 | Boucher |
| 5,940,942 A | 8/1999 | Fong |
| 5,941,900 A | 8/1999 | Bonutti |
| 5,941,901 A | 8/1999 | Egan |
| 5,945,002 A | 9/1999 | BOnutti |
| 5,947,982 A | 9/1999 | Duran |
| 5,948,000 A | 9/1999 | Larsen |
| 5,948,001 A | 9/1999 | Larsen |
| 5,948,002 A | 9/1999 | Bonutti |
| 5,951,590 A | 9/1999 | Goldfarb |
| 5,957,953 A | 9/1999 | DiPoto |
| 5,961,499 A | 10/1999 | Bonutti |
| 5,961,521 A | 10/1999 | Roger |
| 5,961,554 A | 10/1999 | Janson |
| 5,964,765 A | 10/1999 | Fenton |
| 5,964,769 A | 10/1999 | Wagner |
| 5,968,046 A | 10/1999 | Castleman |
| 5,968,047 A | 10/1999 | Reed |
| 5,980,520 A | 11/1999 | Vancaillie |
| 5,980,559 A | 11/1999 | Bonutti |
| 5,984,929 A | 11/1999 | Bashiri |
| 5,989,282 A | 11/1999 | Bonutti |
| 5,993,458 A | 11/1999 | Vaitekunas |
| 5,993,477 A | 11/1999 | Vaitekunas |
| 6,007,567 A | 12/1999 | Bonutti |
| 6,007,580 A | 12/1999 | Lehto |
| 6,010,525 A | 1/2000 | Bonutti |
| 6,010,526 A | 1/2000 | Sandstrom |
| 6,017,321 A | 1/2000 | Boone |
| 6,033,429 A | 3/2000 | Magovern |
| 6,033,430 A | 3/2000 | Bonutti |
| 6,045,551 A | 4/2000 | Bonutti |
| 6,056,751 A | 5/2000 | Fenton |
| 6,056,772 A | 5/2000 | BOnutti |
| 6,056,773 A | 5/2000 | Bonutti |
| 6,059,797 A | 5/2000 | Mears |
| 6,059,817 A | 5/2000 | Bonutti |
| 6,059,827 A | 5/2000 | Fenton |
| 6,063,095 A | 5/2000 | Wang |
| 6,066,151 A | 5/2000 | Miyawaki |
| 6,066,160 A | 5/2000 | Colvin |
| 6,066,166 A | 5/2000 | Bischoff |
| 6,068,637 A | 5/2000 | Popov |
| 6,077,277 A | 6/2000 | Mollenauer |
| 6,077,292 A | 6/2000 | Bonutti |
| 6,080,161 A | 6/2000 | Eaves |
| 6,083,522 A | 7/2000 | Chu |
| 6,086,593 A | 7/2000 | Bonutti |
| 6,086,608 A | 7/2000 | Ek |
| 6,099,531 A | 8/2000 | Bonutti |
| 6,099,537 A | 8/2000 | Sugai |
| 6,099,550 A | 8/2000 | Yoon |
| 6,099,552 A | 8/2000 | Adams |
| 6,102,850 A | 8/2000 | Wang |
| 6,106,545 A | 8/2000 | Egan |
| 6,117,160 A | 9/2000 | Bonutti |
| 6,120,536 A | 9/2000 | Ding |
| 6,125,574 A | 10/2000 | Ganaja |
| 6,126,677 A | 10/2000 | Ganaja |
| 6,139,320 A | 10/2000 | Hahn |
| RE36,974 E | 11/2000 | Bonutti |
| 6,149,669 A | 11/2000 | Li |
| 6,152,949 A | 11/2000 | Bonutti |
| 6,155,756 A | 12/2000 | Mericle |
| 6,159,224 A | 12/2000 | Yoon |
| 6,159,234 A | 12/2000 | Bonutti |
| 6,171,307 B1 | 1/2001 | Orlich |

(56) References Cited

U.S. PATENT DOCUMENTS

| | | |
|---|---|---|
| 6,174,324 B1 | 1/2001 | Egan |
| 6,179,840 B1 | 1/2001 | Bowman |
| 6,179,850 B1 | 1/2001 | Goradia |
| 6,187,008 B1 | 2/2001 | Hamman |
| 6,190,400 B1 | 2/2001 | Van De Moer |
| 6,190,401 B1 | 2/2001 | Green |
| 6,200,322 B1 | 3/2001 | Branch |
| 6,203,565 B1 | 3/2001 | Bonutti |
| 6,217,591 B1 | 4/2001 | Egan |
| 6,224,593 B1 | 5/2001 | Ryan |
| 6,224,630 B1 | 5/2001 | Bao |
| 6,228,086 B1 | 5/2001 | Wahl |
| 6,231,592 B1 | 5/2001 | Bonutti |
| 6,238,395 B1 | 5/2001 | Bonutti |
| 6,238,396 B1 | 5/2001 | Bonutti |
| 6,258,091 B1 | 7/2001 | Sevrain |
| 6,264,675 B1 | 7/2001 | Brotz |
| 6,267,761 B1 | 7/2001 | Ryan |
| 6,273,717 B1 | 8/2001 | Halm |
| 6,280,474 B1 | 8/2001 | Cassidy |
| 6,286,746 B1 | 9/2001 | Egan |
| 6,287,325 B1 | 9/2001 | Bonutti |
| 6,293,961 B2 | 9/2001 | Schwartz |
| 6,306,159 B1 | 10/2001 | Schwartz |
| 6,309,405 B1 | 10/2001 | Bonutti |
| 6,312,448 B1 | 11/2001 | Bonutti |
| 6,338,730 B1 | 1/2002 | Bonutti |
| 6,340,365 B2 | 1/2002 | Dittrich |
| 6,348,056 B1 | 2/2002 | Batkes |
| 6,358,271 B1 | 3/2002 | Egan |
| 6,364,897 B1 | 4/2002 | Bonutti |
| 6,368,325 B1 | 4/2002 | McKinley |
| 6,368,343 B1 | 4/2002 | Bonutti |
| 6,371,957 B1 | 4/2002 | Amrein |
| 6,409,742 B1 | 6/2002 | Fulton |
| 6,409,743 B1 | 6/2002 | Fenton |
| 6,419,704 B1 | 7/2002 | Ferree |
| 6,423,088 B1 | 7/2002 | Fenton |
| 6,425,919 B1 | 7/2002 | Lambrect |
| 6,428,562 B2 | 8/2002 | Bonutti |
| 6,432,115 B1 | 8/2002 | Mollenauer |
| 6,447,516 B1 | 9/2002 | Bonutti |
| 6,450,985 B1 | 9/2002 | Schoelling |
| 6,461,360 B1 | 10/2002 | Adams |
| 6,468,293 B2 | 10/2002 | Bonutti |
| 6,475,230 B1 | 11/2002 | Bonutti |
| 6,488,196 B1 | 12/2002 | Fenton |
| 6,500,195 B2 | 12/2002 | Bonutti |
| 6,503,259 B2 | 1/2003 | Huxel |
| 6,530,933 B1 | 3/2003 | Yeung |
| 6,535,764 B2 | 3/2003 | Imran |
| 6,544,267 B1 | 4/2003 | Cole |
| 6,545,390 B1 | 4/2003 | Hahn |
| 6,547,792 B1 | 4/2003 | Tsuji |
| 6,551,304 B1 | 4/2003 | Whalen |
| 6,554,852 B1 | 4/2003 | Oberlander |
| 6,527,774 B2 | 5/2003 | Lieberman |
| 6,558,390 B2 | 5/2003 | Cragg |
| 6,568,313 B2 | 5/2003 | Fukui |
| 6,569,187 B1 | 5/2003 | Bonutti |
| 6,572,635 B1 | 6/2003 | Bonutti |
| D477,776 S | 7/2003 | Pontaoe |
| 6,557,426 B2 | 7/2003 | Reinemann |
| 6,585,750 B2 | 7/2003 | Bonutti |
| 6,592,609 B1 | 7/2003 | Bonutti |
| 6,594,517 B1 | 7/2003 | Nevo |
| 6,585,764 B2 | 8/2003 | Wright |
| 6,605,090 B1 * | 8/2003 | Trieu .............. A61B 17/8042 606/281 |
| 6,610,080 B2 | 8/2003 | Morgan |
| 6,618,910 B1 | 9/2003 | Pontaoe |
| 6,623,486 B1 | 9/2003 | Weaver |
| 6,623,487 B1 | 9/2003 | Goshert |
| 6,626,944 B1 | 9/2003 | Taylor |
| 6,632,245 B2 | 10/2003 | Kim |
| 6,635,073 B2 | 10/2003 | Bonutti |
| 6,638,279 B2 | 10/2003 | Bonutti |
| 6,641,592 B1 | 11/2003 | Sauer |
| 6,645,227 B2 | 11/2003 | Fallin |
| 6,666,877 B2 | 12/2003 | Morgan |
| 6,669,705 B2 | 12/2003 | Westhaver |
| 6,679,888 B2 | 1/2004 | Green |
| 6,685,750 B1 | 2/2004 | Plos |
| 6,699,240 B2 | 3/2004 | Fracischelli |
| 6,702,821 B2 | 3/2004 | BOnutti |
| 6,705,179 B1 | 3/2004 | Mohtasham |
| 6,709,457 B1 | 3/2004 | Otte |
| 6,719,765 B2 | 4/2004 | Bonutti |
| 6,719,797 B1 | 4/2004 | Ferree |
| 6,722,552 B2 | 4/2004 | Fenton |
| 6,733,531 B1 | 5/2004 | Trieu |
| 6,764,514 B1 | 7/2004 | Lieberman |
| 6,770,078 B2 | 8/2004 | Bonutti |
| 6,780,198 B1 | 8/2004 | Gregoire |
| 6,786,989 B2 | 9/2004 | Torriani |
| 6,796,003 B1 | 9/2004 | Marvel |
| 6,818,010 B2 | 11/2004 | Eichhorn |
| 6,823,871 B2 | 11/2004 | Schmieding |
| 6,860,885 B2 | 3/2005 | Bonutti |
| 6,878,167 B2 | 4/2005 | Ferree |
| 6,893,434 B2 | 5/2005 | Fenton |
| 6,899,722 B2 | 5/2005 | Bonutti |
| 6,890,334 B2 | 7/2005 | Brace |
| 6,913,666 B1 | 7/2005 | Aeschlimann |
| 6,921,264 B2 | 7/2005 | Mayer |
| 6,923,824 B2 | 8/2005 | Morgan |
| 6,932,835 B2 | 8/2005 | Bonutti |
| 6,942,684 B2 | 9/2005 | Bonutti |
| 6,944,111 B2 | 9/2005 | Nakamura |
| 6,955,540 B2 | 10/2005 | Mayer |
| 6,955,683 B2 | 10/2005 | Bonutti |
| 6,958,077 B2 | 10/2005 | Suddaby |
| 6,981,983 B1 | 1/2006 | Rosenblatt |
| 6,997,940 B2 | 2/2006 | Bonutti |
| 7,001,411 B1 | 2/2006 | Dean |
| 7,004,959 B2 | 2/2006 | BOnutti |
| 7,008,226 B2 | 3/2006 | Mayer |
| 7,033,379 B2 | 4/2006 | Peterson |
| 7,048,755 B2 | 5/2006 | Bonutti |
| 7,066,960 B1 | 6/2006 | Dickman |
| 7,087,073 B2 | 8/2006 | BOnutti |
| 7,090,111 B2 | 8/2006 | Egan |
| 7,094,251 B2 | 8/2006 | Bonutti |
| 7,104,996 B2 | 9/2006 | Bonutti |
| 7,128,763 B1 | 10/2006 | Blatt |
| 7,018,380 B2 | 12/2006 | Cole |
| 7,147,652 B2 | 12/2006 | BOnutti |
| 7,160,405 B2 | 1/2007 | Aeschlimann |
| 7,179,259 B1 | 2/2007 | Gibbs |
| 7,192,448 B2 | 3/2007 | Ferree |
| 7,217,279 B2 | 5/2007 | Reese |
| 7,217,290 B2 | 5/2007 | Bonutti |
| 7,241,297 B2 | 7/2007 | Shaolian |
| 7,250,051 B2 | 7/2007 | Fracischelli |
| 7,252,685 B2 | 8/2007 | Bindseil |
| 7,273,497 B2 | 9/2007 | Ferree |
| 7,329,263 B2 | 2/2008 | BOnutti |
| 7,335,205 B2 | 2/2008 | Aeschlimann |
| 7,429,266 B2 | 9/2008 | Bonutti |
| 7,445,634 B2 | 11/2008 | Trieu |
| 7,481,825 B2 | 1/2009 | Bonutti |
| 7,481,831 B2 | 1/2009 | Bonutti |
| 7,510,895 B2 | 3/2009 | Rateman |
| 7,854,750 B2 | 12/2010 | Bonutti |
| 7,879,072 B2 | 2/2011 | Bonutti |
| 7,891,691 B2 | 2/2011 | Bearey |
| 7,967,820 B2 | 6/2011 | Bonutti |
| 8,128,669 B2 | 3/2012 | Bonutti |
| 8,140,982 B2 | 3/2012 | Hamilton |
| 8,147,514 B2 | 4/2012 | Bonutti |
| 8,162,977 B2 | 4/2012 | Bonutti |
| 2001/0002440 A1 | 5/2001 | Bonutti |
| 2001/0009250 A1 | 7/2001 | Herman |
| 2001/0041916 A1 | 11/2001 | Bonutti |

(56) References Cited

U.S. PATENT DOCUMENTS

| | | |
|---|---|---|
| 2002/0016593 A1 | 2/2002 | Hearn |
| 2002/0016633 A1 | 2/2002 | Lin |
| 2002/0026244 A1 | 2/2002 | Trieu |
| 2002/0029083 A1 | 3/2002 | Zucherman |
| 2002/0029084 A1 | 3/2002 | Paul |
| 2002/0045902 A1 | 4/2002 | Bonutti |
| 2002/0062153 A1 | 5/2002 | Paul |
| 2002/0103495 A1 | 8/2002 | Cole |
| 2002/0123750 A1 | 9/2002 | Eisermann |
| 2002/0183762 A1 | 12/2002 | Anderson |
| 2002/0188301 A1 | 12/2002 | Dallara |
| 2003/0039196 A1 | 2/2003 | Nakamura |
| 2003/0040758 A1 | 2/2003 | Wang |
| 2003/0065361 A1 | 4/2003 | Dreyfuss |
| 2003/0105474 A1 | 6/2003 | Bonutti |
| 2003/0118518 A1 | 6/2003 | Hahn |
| 2003/0158582 A1 | 8/2003 | BOnutti |
| 2003/0167072 A1 | 9/2003 | Oberlander |
| 2003/0181800 A1 | 9/2003 | Bonutti |
| 2003/0195530 A1 | 10/2003 | Thill |
| 2003/0195565 A1 | 10/2003 | Bonutti |
| 2003/0204204 A1 | 10/2003 | Bonutti |
| 2003/0216742 A1 | 11/2003 | Wetzler |
| 2003/0225438 A1 | 12/2003 | Bonutti |
| 2003/0229361 A1 | 12/2003 | Jackson |
| 2004/0010287 A1 | 1/2004 | Bonutti |
| 2004/0030341 A1* | 2/2004 | Aeschlimann ... A61B 17/00491 606/232 |
| 2004/0034357 A1 | 2/2004 | Beane |
| 2004/0097939 A1 | 5/2004 | Bonutti |
| 2004/0098050 A1 | 5/2004 | Foerster |
| 2004/0138703 A1 | 7/2004 | Alleyne |
| 2004/0143334 A1 | 7/2004 | Ferree |
| 2004/0167548 A1 | 8/2004 | Bonutti |
| 2004/0220616 A1 | 11/2004 | Bonutti |
| 2004/0225325 A1 | 11/2004 | Bonutti |
| 2004/0230223 A1 | 11/2004 | Bonutti |
| 2004/0236374 A1 | 11/2004 | Bonutti |
| 2005/0033366 A1 | 2/2005 | Cole |
| 2005/0038514 A1 | 2/2005 | Helm |
| 2005/0043796 A1 | 2/2005 | Grant |
| 2005/0071012 A1 | 3/2005 | Serhan |
| 2005/0090827 A1 | 4/2005 | Gedebou |
| 2005/0096699 A1 | 5/2005 | Wixey |
| 2005/0113928 A1 | 5/2005 | Cragg |
| 2005/0126680 A1 | 6/2005 | Aeschlimann |
| 2005/0143826 A1 | 6/2005 | Zucherman |
| 2005/0149024 A1 | 7/2005 | Ferrante |
| 2005/0149029 A1 | 7/2005 | Bonutti |
| 2005/0203521 A1 | 9/2005 | Bonutti |
| 2005/0216059 A1 | 9/2005 | Bonutti |
| 2005/0216087 A1 | 9/2005 | Zucherman |
| 2005/0222620 A1 | 10/2005 | Bonutti |
| 2005/0240190 A1 | 10/2005 | Gall |
| 2005/0240227 A1 | 10/2005 | Bonutti |
| 2005/0246021 A1 | 11/2005 | RIngeisen |
| 2005/0261684 A1 | 11/2005 | Shaolian |
| 2005/0267481 A1 | 12/2005 | Carl |
| 2005/0267534 A1 | 12/2005 | Bonutti |
| 2006/0009855 A1 | 1/2006 | Goble |
| 2006/0015101 A1 | 1/2006 | Warburton |
| 2006/0015108 A1 | 1/2006 | Bonutti |
| 2006/0024357 A1 | 2/2006 | Carpenter |
| 2006/0026244 A1 | 2/2006 | Watson |
| 2006/0200199 A1 | 2/2006 | Bonutti |
| 2006/0229623 A1 | 2/2006 | BOnutti |
| 2006/0064095 A1 | 3/2006 | Senn |
| 2006/0089646 A1 | 4/2006 | Bonutti |
| 2006/0122600 A1 | 6/2006 | Cole |
| 2006/0122704 A1 | 6/2006 | Vresilovic |
| 2006/0142799 A1 | 6/2006 | Bonutti |
| 2006/0167495 A1 | 7/2006 | Bonutti |
| 2006/0265009 A1 | 7/2006 | Bonutti |
| 2006/0265011 A1 | 7/2006 | Bonutti |
| 2006/0212073 A1 | 9/2006 | Bonutti |
| 2006/0217765 A1 | 9/2006 | Bonutti |
| 2006/0235470 A1 | 10/2006 | Bonutti |
| 2006/0241695 A1 | 10/2006 | Bonutti |
| 2006/0264950 A1 | 11/2006 | Nelson |
| 2007/0032825 A1 | 2/2007 | Bonutti |
| 2007/0088362 A1 | 4/2007 | Bonutti |
| 2007/0118129 A1 | 5/2007 | Fraser |
| 2007/0198555 A1 | 8/2007 | Friedman |
| 2007/0265561 A1 | 11/2007 | Yeung |
| 2007/0270833 A1 | 11/2007 | Bonutti |
| 2008/0021474 A1 | 1/2008 | Bonutti |
| 2008/0039845 A1 | 2/2008 | Bonutti |
| 2008/0039873 A1 | 2/2008 | Bonutti |
| 2008/0046090 A1 | 2/2008 | Paul |
| 2008/0097448 A1 | 4/2008 | Binder |
| 2008/0108897 A1 | 5/2008 | Bonutti |
| 2008/0108916 A1 | 5/2008 | Bonutti |
| 2008/0114399 A1 | 5/2008 | Bonutti |
| 2008/0132950 A1 | 6/2008 | Lange |
| 2008/0140116 A1 | 6/2008 | Bonutti |
| 2008/0140117 A1 | 6/2008 | BOnutti |
| 2008/0195145 A1 | 8/2008 | BOnutti |
| 2008/0269753 A1 | 10/2008 | Cannestra |
| 2008/0269808 A1 | 10/2008 | Gall |
| 2009/0024161 A1 | 1/2009 | Bonutti |
| 2009/0138014 A1 | 1/2009 | Bonutti |
| 2009/0093684 A1 | 4/2009 | Schorer |
| 2009/0194969 A1 | 8/2009 | Bearey |
| 2010/0211120 A1 | 8/2010 | Bonutti |
| 2011/0060375 A1 | 3/2011 | Bonutti |
| 2011/0295253 A1 | 12/2011 | Bonutti |
| 2012/0165841 A1 | 6/2012 | BOnutti |
| 2012/0191140 A1 | 7/2012 | BOnutti |
| 2012/0215233 A1 | 8/2012 | Bonutti |

FOREIGN PATENT DOCUMENTS

| | | |
|---|---|---|
| CA | 2698057 | 3/2009 |
| DE | 1903316 B2 | 10/1964 |
| DE | 1903016 | 8/1970 |
| DE | 3517204 | 11/1986 |
| DE | 3722538 | 1/1989 |
| DE | 9002884 U1 | 1/1991 |
| EP | 784454 | 5/1996 |
| EP | 773004 | 5/1997 |
| EP | 1614525 | 1/2006 |
| EP | 1988837 | 8/2007 |
| EP | 2134294 | 12/2009 |
| FR | 22717368 | 3/1994 |
| FR | 2728779 | 1/1995 |
| FR | 2736257 | 7/1995 |
| FR | 2750031 | 6/1996 |
| FR | 2771621 | 11/1997 |
| FR | 2785171 | 10/1998 |
| GB | 2093701 A | 9/1982 |
| GB | 2306110 A | 4/1997 |
| JP | 8140982 | 6/1996 |
| SU | 184396 | 7/1966 |
| WO | 199112779 | 9/1991 |
| WO | 1994008642 | 4/1994 |
| WO | 199531941 | 11/1995 |
| WO | 1996014802 | 5/1996 |
| WO | 1997012779 | 4/1997 |
| WO | 1997049347 | 12/1997 |
| WO | 1998011838 | 3/1998 |
| WO | 1998026720 | 6/1998 |
| WO | 2002053011 | 7/2002 |
| WO | 2007092869 | 8/2007 |
| WO | 2008116203 | 9/2008 |
| WO | 2009029908 | 3/2009 |
| WO | 2010099222 | 2/2010 |

OTHER PUBLICATIONS

Femoral Bone Plug Recession in Endoscope Anterior Cruciate Ligament Reconstruction, David E. Taylor, Arthroscopy: The Journal of Arthroscopic and Related Surgery, Aug. 1996.

Meniscus Replacement with Bone Anchors: A Surgical Technique,

(56) References Cited

OTHER PUBLICATIONS

Shelton, Arthroscopy: The Journal of Arcioscopic and Related Surgery, 1994.
Problem Solving Report Question No. 1014984.066, Ultrasonic Welding, (c) 1999.
Guide to Ultrasound Plastic Assembly, Dukane Corporation, Ultrasonic Division Publication, (c) 1995.
Branson, Polymers: Characteristics and Compatibility for Ultrasonic Assembly, Applied Technologies Group, Publication unknown.
Enabling Local Drug Delivery—Implant Device Combination Therapies, Surmodics, Inc., (c) 2003.
Stent Based Delivery of Sirolimus Reduces Neointimal Formation in a Porcine Coronary Model, Takeshi Suzuki, American Heart Association, Inc. (c) 2001.
Why Tie a Knot When You Can Use Y-Knot?, Innovasive Devices Inc., (c) 1998.
Ask Oxford projection, compact oxford english dicitionary: projection, Mar. 30, 2009.
Ask Oxford projection, compact oxford english dicitionary: slit, Mar. 30, 2009.
Textured Surface Technology, Branson Technolog, Branson Ultrasonics Copr., (c) 1992.
Arthrex, Protect your graft, Am J Sports Med, vol. 22, No. 4, Jul.-Aug. 1994.
Barrett et al, T-Fix endoscopic meniscal repair: technique and approach to different types of tears, Apr. 1995, Arthroscopy 2 vol. 11 No. 2 p. 245-51.
Cope, Suture Anchor for Visceral Drainage, AJR, vol. 148 p. 160-162, Jan. 1986.
Gabriel, Arthroscopic Fixation Devices, Wiley Enc. of Biomed Eng., 2006.
Innovasive, We've got you covered, Am J Sports Med, vol. 26, No. 1, Jan.-Feb. 1998.
510k—TranSet Fracture Fixation System, Feb. 24, 2004, k033717.
510k—Linvatec Biomaterials modification of Duet and impact Suture Anchor, Nov. 19, 2004, k042966.
510k, arthrex pushlock, Jun. 29, 2005, K051219.
Non-Final Office Action dated Jun. 29, 2016 relating to U.S. Appl. No. 14/867,621, 7 pgs.
Final Office Action dated Feb. 2, 2017 relating to U.S. Appl. No. 14/867,621, 9 pgs.
510k, mitek micro anchor, Nov. 6, 1996, K962511.
510k, Multitak Suture System, Jan. 10, 1997, K964324.
510k, Modified Mitek 3.5mm Absorbable Suture Anchor System, Jun. 9, 1997, K970896.
510K, Summary for Arthrex Inc.'s Bio-Interference Screw, Jul. 9, 1997, K971358.
510k, Surgicraft Bone Tie, Sep. 25, 1998, K982719.
Karlsson et al, Repair of Bankart lesions with a suture anchor in recurrent dislocation of the shoulder, Scand. j. of Med & Science in Sports, 1995, 5:170-174.
Madjar et al, Minimally Invasive Pervaginam Procedures, for the Treatment of Female Stress Incontinence . . . , Artificial Organs, 22 (10) 879-885, 1998.
Nowak et al, Comparative Study of Fixation Techniques in the Open Bankart Operation Using Either a Cannulated Screw or Suture-Anchors, Acta Orthopcedica Belgica, vol. 64—Feb. 1998.
Packer et al, Repair of Acute Scapho-Lunate Dissociation Facilitated by the "Tag"* Suture Anchor, Journal of Hand Surgery (British and European Volume, 1994) 19B: 5: 563-564.
Richmond, Modificatio of the Bankart reconstruction with a suture anchor, Am J Sports Med, vol. 19, No. 4, p. 343-346, 1991.
Shea et al, Technical Note: Arthroscopic Rotator Cuff Repair Using a Transhumeral Approach to Fixation, Arthroscopy: The Journal of Arthroscopic and Related Surgery, vol. 14, No. 1 Jan.-Feb. 1998: pp. 118-122.
Tfix, Acufex just tied the knot . . . , Am. J. Sports Med., vol. 22, No. 3, May-Jun. 1994.
Wong et al, Case Report: Proper Insertion Angle is Essential to Prevent Intra-Articular Protrusion of a Knotless Suture 21 Anchor in Shoulder Rotator Cuff Repair, Arthroscopy: The Journal of Arthroscopic and Related Surgery, vol. 26, No. 2 Feb. 2010: pp. 286-290.
Cobb et al, Late Correction of Malunited Intercondylar Humeral Fractures Intra-Articular Osteotomy and Tricortical Bone Grafting, J BoneJointSurg [Br] 1994; 76-B:622-6.
Fellinger, et al, Radial avulsion of the triangular fibrocartilage complex in acute wrist trauma: a new technique for arthroscopic repair, Jun. 1997, Arthroscopy vol. 13 No. 3 p. 370-4.
Hecker et al , Pull-out strength of suture anchors for rotator cuff and Bankart lesion repairs, Nov.-Dec. 1993 , The American Journal of Sports Medicine, vol. 21 No. 6 p. 874-9.
Hernigou et al, Proximal Tibial Osteotomy for Osteoarthritis with Varus Deformity A Ten to Thirteen-Year Follow-Up Study, J Bone Joint Surg, vol. 69-A, No. 3. Mar. 1987, p. 332-354.
Ibarra et al, Glenoid Replacement in Total Shoulder Arthroplasty, The Orthopedic Clinics of Northamerica: Total Shoulder Arthroplasty, vol. 29 No. 3, Jul. 1998 p. 403-413.
Mosca et al, Calcaneal Lengthening for Valgus Deformity of the Hindfoot: Results in Children Who Had Severe, Symptomatic flatfoot and Skewfoot, J Bone Joint Surg,, 1195—p. 499-512.
Murphycet al , Radial Opening Wedge Osteotomy in Madelung's Deformity, J. Hand Surg, vol. 21 A No. 6 Nov. 1996, p. 1035-44.
Biomet, Stanmore Modular Hip, J. Bone Joint Surg., vol. 76-B : No. Two, Mar. 1994.
Intl Prelim Rep on Patentability and Written Opinion for PCT/US10/25263 dated Aug. 30, 2011.
Petition for Inter Partes Review of U.S. Pat. No. 5,980,559, IPR 2013-00603, Filing Date Sep. 24, 2013.
Declaration of David Kaplan, Ph.D. Regarding U.S. Pat. No. 5,980,559, IPR 2013-00603, Sep. 24, 2013.
Petition for Inter Partes Review of U.S. Pat. No. 7,087,073, IPR 2013-00604, Filing Date Sep. 24, 2013.
Declaration of Wayne J. Sebastianelli, MD Regarding U.S. Pat. No. 7,087,073, Sep. 24, 2013, IPR 2013-00604.
Petition for Inter Partes Review of U.S. Pat. No. 6,500,195, IPR 2013-00624, Filing Date Oct. 2, 2013.
Declaration of Dr. Philip Hardy in Support of Petition for Inter Partes Review of U.S. Pat. No. 6,500,195, IPR 2013-00624, Sep. 25, 2013.
Petition for Inter Partes Review of U.S. Pat. No. 5,527,343, IPR 2013-00628, Filing Date Sep. 26, 2013,Sep. 25, 2013.
Declaration of Dr. Philip Hardy in Support of Petition for Inter Partes Review of U.S. Pat. No. 5,527,343, IPR 2013-00628, Sep. 25, 2013.
Corrected Petition for Inter Partes Review of U.S. Pat. No. 5,921,986, IPR 2013-00631, Filing Date Sep. 27, 2013.
Expert Declaration of Steve E. Jordan, MD, for Inter Partes Review of U.S. Pat. No. 5,921,986, IPR 2013-00631, Sep. 24, 2013.
Corrected Petition for Inter Partes Review of U.S. Pat. No. 8,147,514, IPR 2013-00632, Filing Date Sep. 27, 2013.
Declaration of Steve Jordan for U.S. Pat. No. 8,147,514, from IPR 2013-00632, dated Sep. 23, 2013 (exhibit 1009).
Corrected Petition for Inter Partes Review of U.S. Pat. No. 8,147,514, IPR 2013-00633, Filing Date Sep. 27, 2013.
Declaration of Steve Jordan for U.S. Pat. No. 8,147,514, from IPR 2013-00633, dated Sep. 23, 2013 (exhibit 1006).
Flory, Principles of Polymer Chemistry, 1953, selected pages (cited in IPR 2013-00603, exhibit 1012).
Grizzi, Hydrolytic degradation of devices based on poly(DL-lactic acid) size-dependence, Biomaterials, 1995, vol. 16, No. 4, p. 305-11 (cited in IPR 2013-00603, exhibit 1006).
Gopferich, Mechanisms of polymer degradation and erosion, Biomaterials, 1996, vol. 17, No. 2, p. 103-114 (cited in IPR 2013-00603, exhibit 1013).
Gao et el, Swelling of Hydroxypropyl Methylcellulose Matrix Tablets . . . , J. of Pharmaceutical Sciences, vol. 85, No. 7, Jul. 1996, p. 732-740 (cited in IPR 2013-00603, exhibit 1014).
Linvatec, Impact Suture Anchor brochure, 2004 (cited in IPR 2013-00628, exhibit 1010).
Seitz et al, Repair of the Tibiofibular Syndesmosis with a Flexible Implant, J. of Orthopaedic Trauma, vol. 5, No. 1, p. 78-82, 1991 (cited in IPR 2013-00631, exhibit 1007) (cited in 2013-00632).

(56) References Cited

OTHER PUBLICATIONS

Translation of FR2696338 with translator's certificate dated Sep. 17, 2013 (cited in IPR 2013-00631, 2013-00632).
Translation of DE9002844.9 with translator's certificate dated Sep. 26, 2013 (cited in IPR 2013-00631, 2013-00632).
Declaration of Steve Jordan for U.S. Pat. No. 5,921,986, from IPR 2013-00632, dated Sep. 24, 2013 (exhibit 1010).
Declaration of Steve Jordan for U.S. Pat. No. 5,921,986, from IPR 2013-00633, dated Sep. 24, 2013 (exhibit 1007).
Declaration of Dr. Steve E. Jordan for U.S. Pat. No. 8,147,514, from IPR 2013-00631, dated Sep. 23, 2013.
Final Office Action dated Jul. 8, 2010 relating to U.S. Appl. No. 11/416,618, 8 pgs.
Non-Final Office Action dated Oct. 13, 2009 relating to U.S. Appl. No. 11/416,618, 10 pgs.
Final Office Action dated Jun. 24, 2009 relating to U.S. Appl. No. 11/416,618, 14 pgs.
Non-Final Office Action dated Nov. 26, 2008 relating to U.S. Appl. No. 11/416,618, 15 pgs.
Final Office Action dated Jan. 2, 2015 relating to U.S. Appl. No. 13/149,038, 10 pgs.
Non-Final Office Action dated Jun. 19, 2014 relating to U.S. Appl. No. 13/149,038, 12 pgs.
Final Office Action dated Jul. 9, 2013 relating to U.S. Appl. No. 13/149,038, 13 pgs.
Non-Final Office Action dated Sep. 27, 2012 relating to U.S. Appl. No. 13/149,038, 9 pgs.

\* cited by examiner

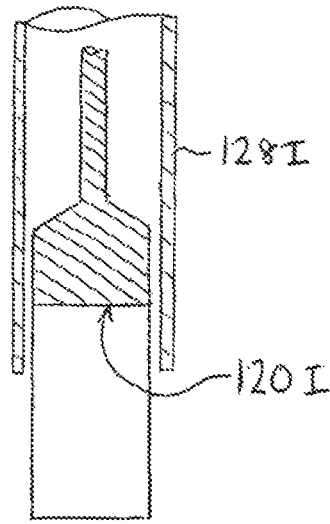
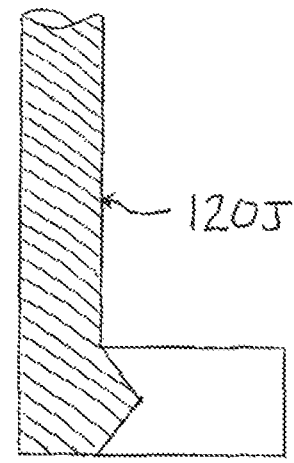
FIG. 3I  FIG. 3J
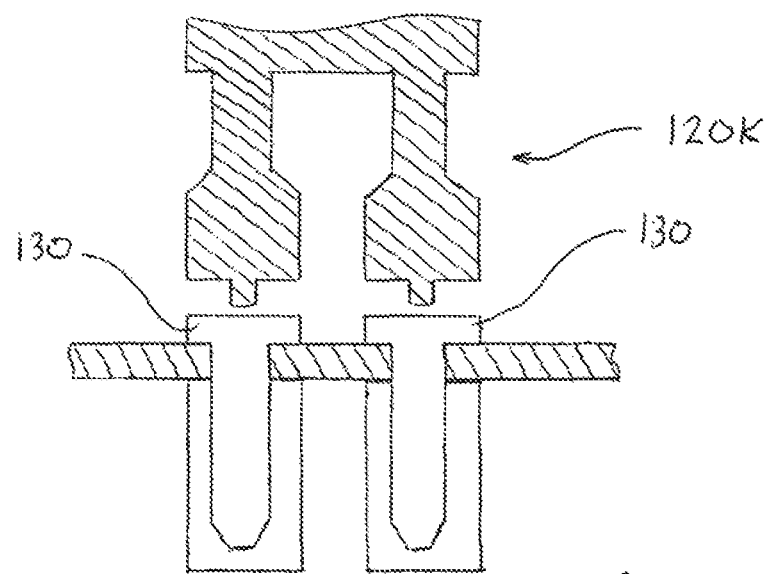
FIG. 3K

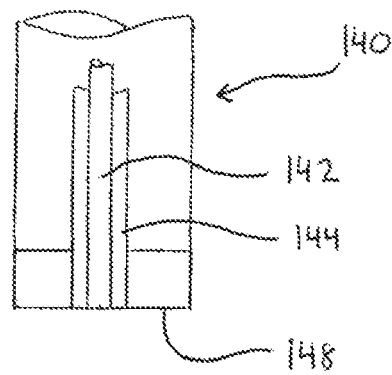
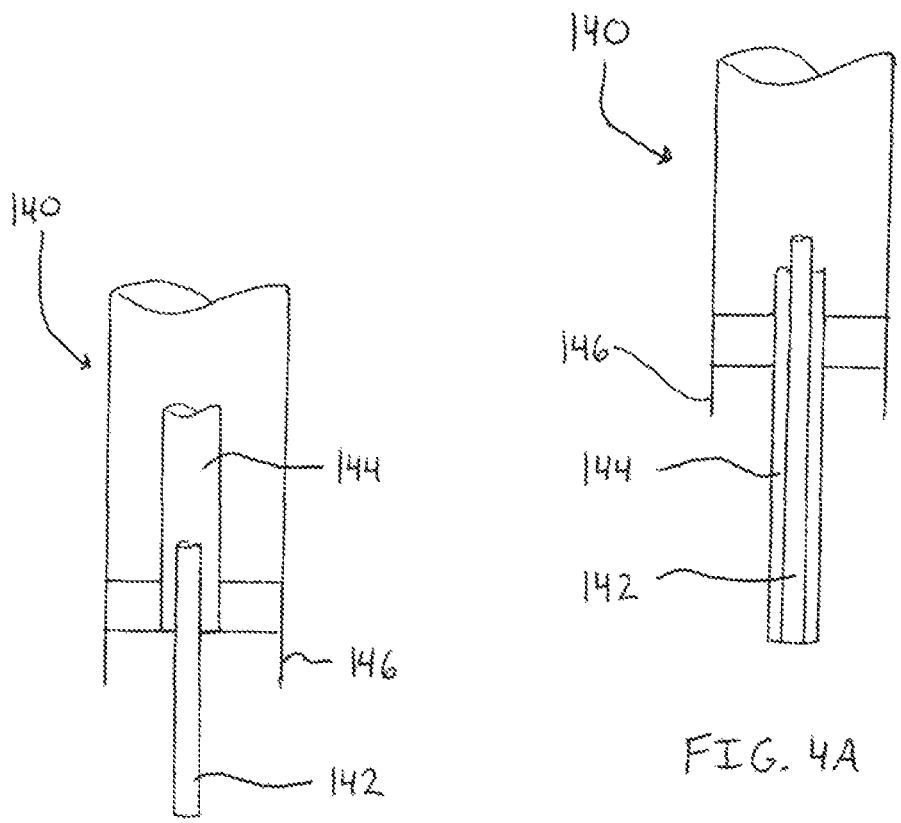

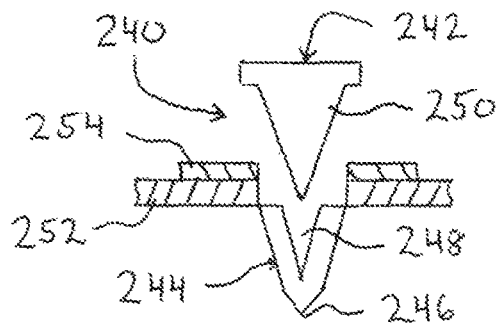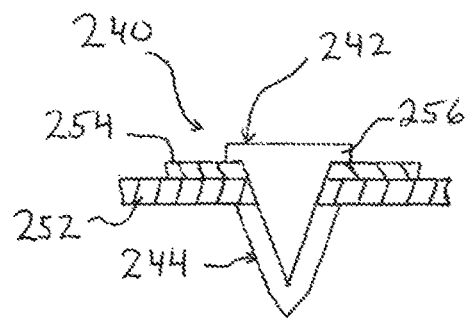
FIG. 16A    FIG. 16B
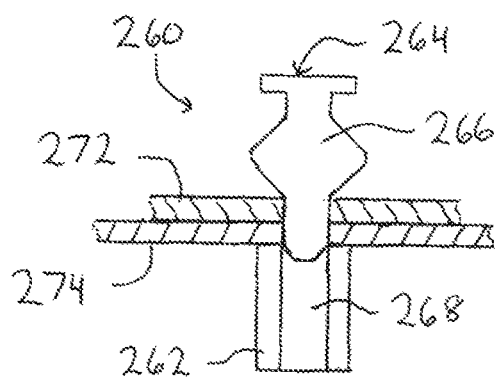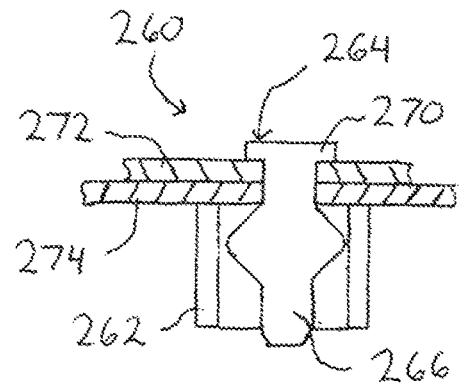
FIG. 17A    FIG. 17B

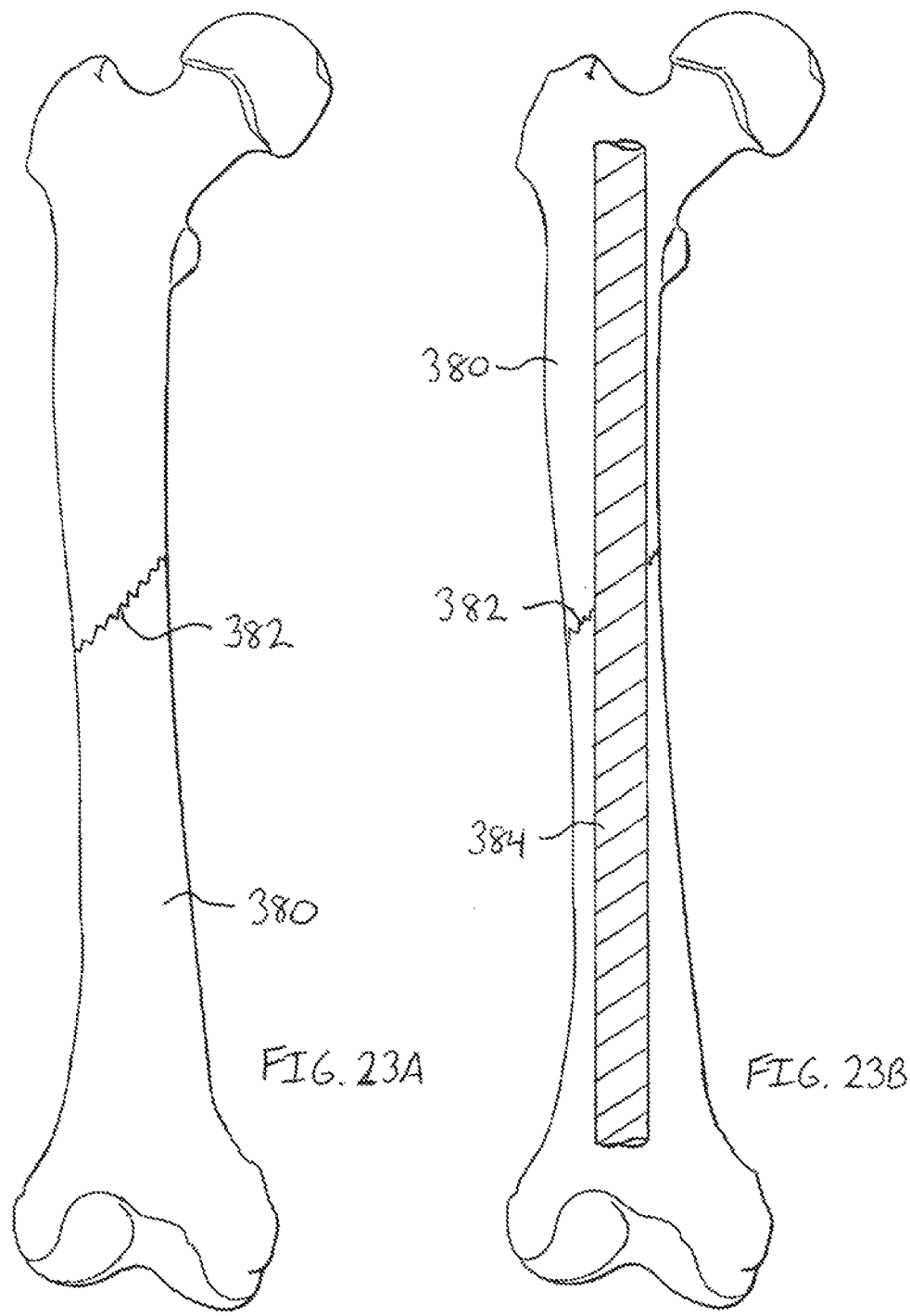

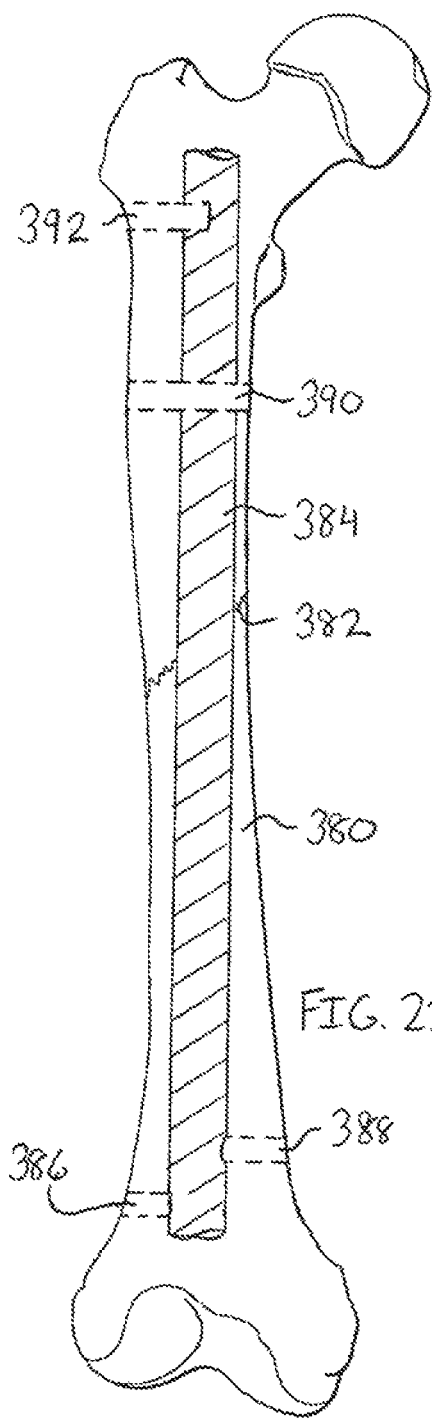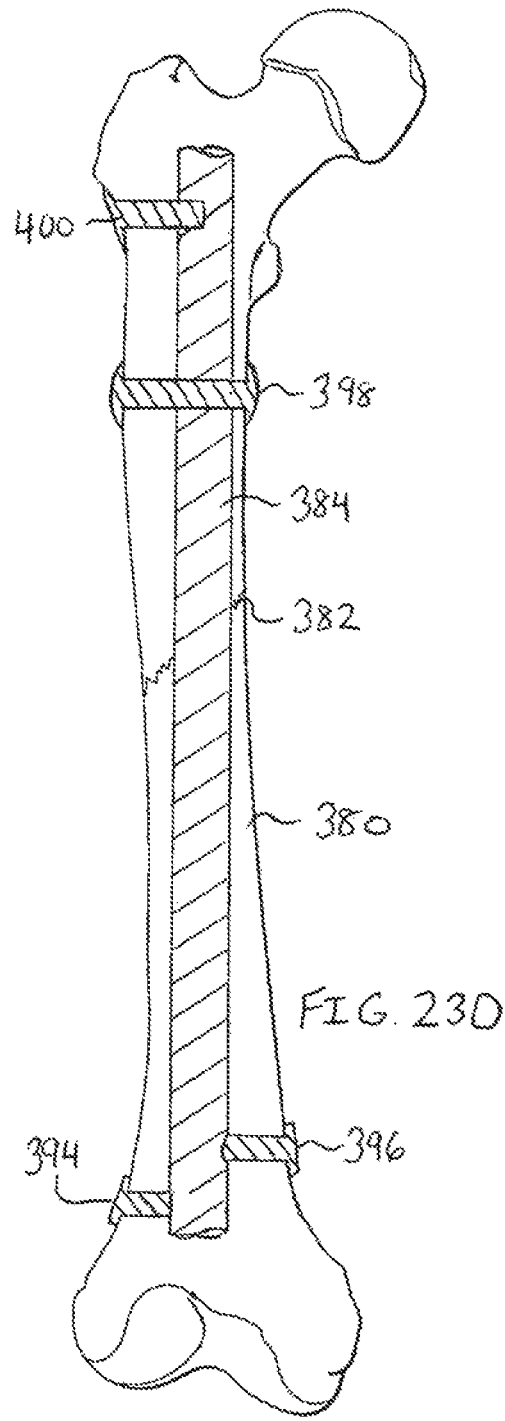
FIG. 23C
FIG. 23D

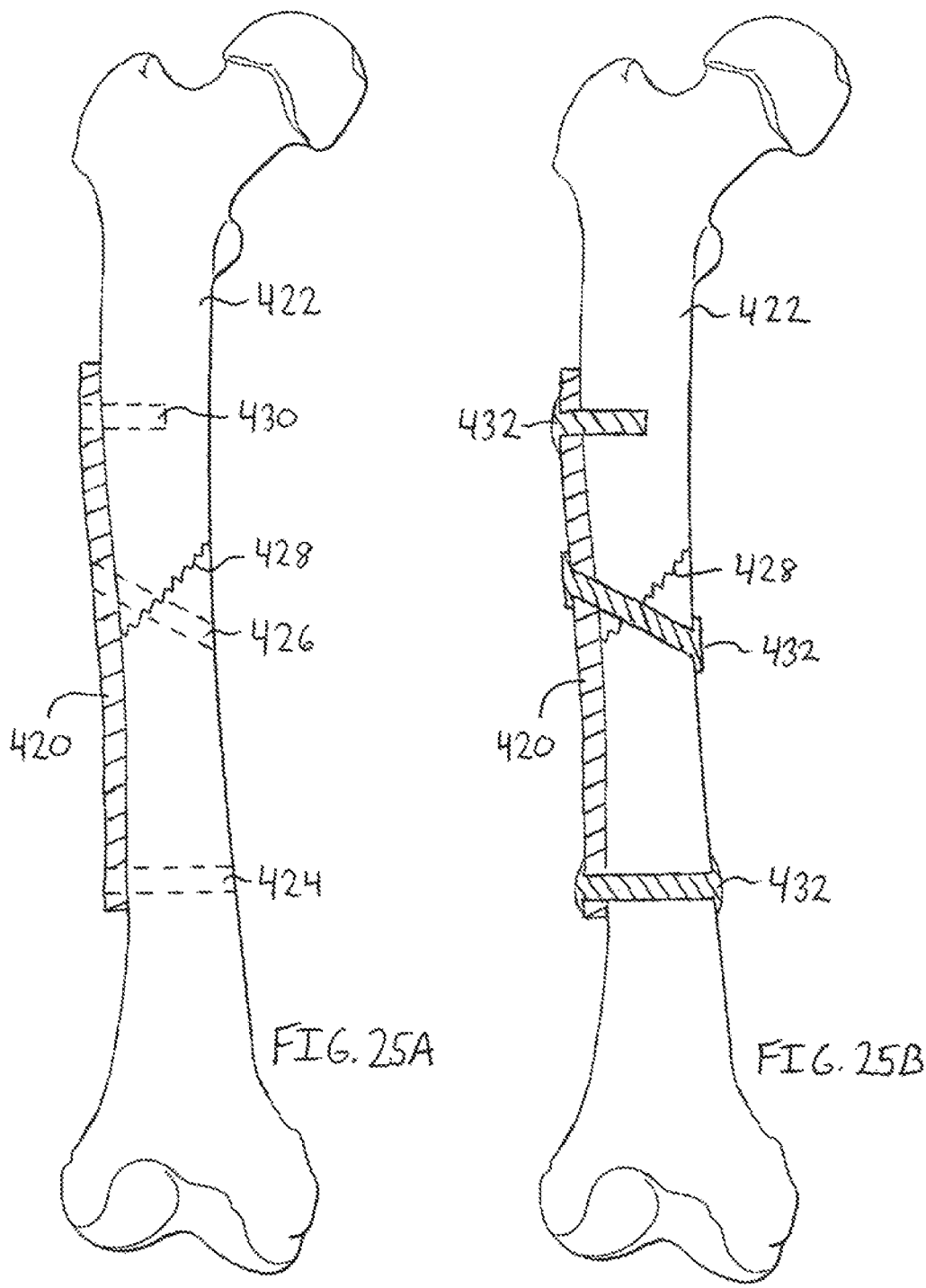

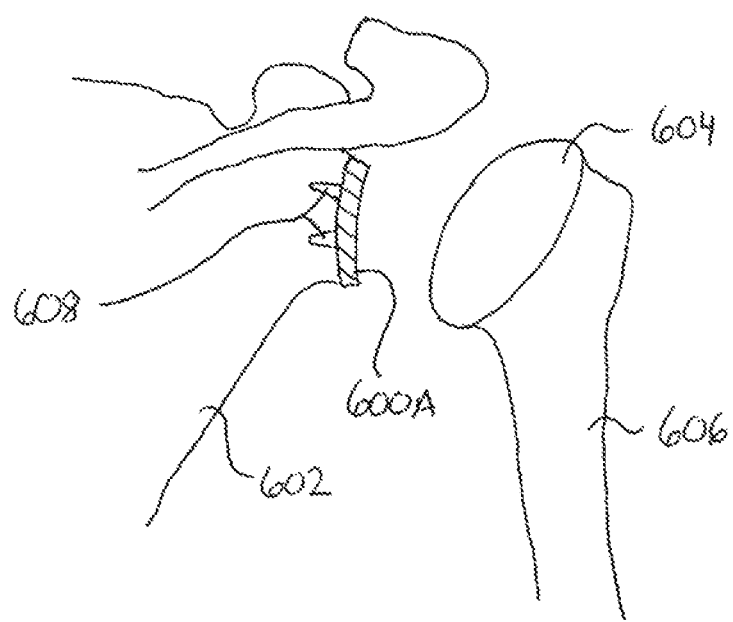
FIG. 38A
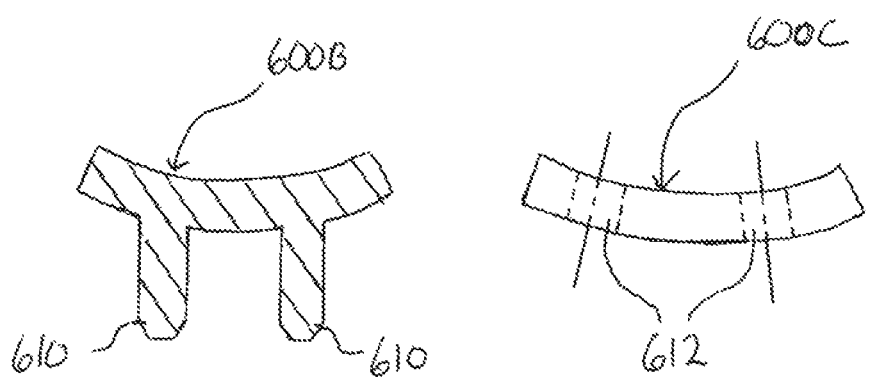
FIG. 38B
FIG. 38C

METHODS AND DEVICES FOR TRAUMA WELDING

CROSS REFERENCE TO RELATED APPLICATIONS

This patent application is a continuation application of U.S. patent application Ser. No. 14/867,621, filed Sep. 28, 2015, which is a continuation application of U.S. patent application Ser. No. 13/149,038, filed May 31, 2011, which is a continuation application of U.S. patent application Ser. No. 11/416,618, filed May 3, 2006, the entirety of each of which is incorporated by reference.

FIELD OF THE INVENTION

The invention relates to the welding of biocompatible material within the body, and more particularly, to the use of ultrasonic energy to bond thermoplastic material intracorporeally to stabilize tissue, such as a fractured bone.

BACKGROUND OF THE INVENTION

Fractured bones are a common injury seen in trauma centers. Sports activities, vehicle accidents, industrial-type incidents, and slip and fall cases are just a few examples of how bones may become fractured. Surgeons in trauma centers frequently encounter many different types of fractures with a variety of different bones. Each bone and each fracture type may require unique procedures and devices for repairing the bone. Currently, a one-solution-fixes-all device is not available to repair fractured bones. Instead, surgeons may use a combination of bone screws, bone plates, and intramedullary rods.

Bone plates may be positioned internal to the skin, i.e. positioned against the fractured bone, or may be positioned external to the skin with rods connecting the bone and plate. Conventional bone plates are particularly well-suited to promote healing of the fracture by compressing the fracture ends together and drawing the bone into close apposition with other fragments and the bone plate. However, one drawback with plates and screws is that with the dynamic loading placed on the plate, loosening of the screws and loss of stored compression can result.

To reduce the potential of loosening, locking screws and a locking bone plate may be used. U.S. Pat. No. 5,085,660 to Lin discloses a locking plate system. The system has multiple locking pins, each with one end formed as a screw to lock in the pending fixation bones or vertebral tubercles, with another end defining rectangular or similarly shaped locking post having a threaded locking end. Near the locking post end, there is formed a stopping protrusion. A plate defines multiple locking bores disposed at one side to be placed over the locking post end until the plate reaches the stopping protrusion on the locking pin. The plate defines multiple threaded screwing bores near the other side to receive locking pin screw. Multiple locking devices fix the side of the plate having locking bores to the locking post end of its locking pins. Multiple screwing pins each have one end formed as a pin to be used for penetrating the threaded screwing bore to lock into the bone or the vertebral tubercle. Another end which forms a head is for holding against the threaded screwing bore of the plate. Threads are provided near the head for the screwing pins to be screwed within the threaded screwing bore of the plate.

An example of an external bone plate system is disclosed in U.S. Pat. No. 6,171,307 to Orlich. Orlich teaches an apparatus and procedure for the external unilateral fracture fixation, fracture compression or enlargement of osseous tissue with a metal or equivalent material slotted forked stick to hold and position the threaded pins in its length, inserted in the bone with multiple fastening slidable screws and their bolts to attach the pins to the slotted forked stick, a solid slidable cube to hold and position the slotted forked stick, a supporting axial bar, and an axial threaded bar. A preferred embodiment includes at least three slotted forked sticks that hold and fix, with the use of compression screws and their bolts, threaded pins that penetrate the proximal and distal fragments of the bone through both corticals. Another preferred embodiment includes slotted forked sticks that adapt to the threaded pins, introduced in the bone, at any degree of inclination or orientation that these pins might have with respect to the bone.

In addition to internal or external bone plates, surgeons sometimes use intramedullary rods to repair long bone fractures, such as fractures of the femur, radius, ulna, humerus, fibula, and tibia. The rod or nail is inserted into the medullary canal of the bone and affixed therein by screws or bolts. After complete healing of the bone at the fracture site, the rod may be removed through a hole drilled in the end of the bone. One problem associated with the use of today's intramedullary rods is that it is often difficult to treat fractures at the end of the long bone. Fastener members, such as bolts, are positioned through the cortical bone and into threaded openings in the rod. However, the number and positioning of the bolt/screw openings are limited at the tip of the rod because of the decreased surface area of the rod and the reduced strength at the tip of the rod. Therefore, fractured bone sections at the distal end of a femur, for example, may not be properly fastened to the intramedullary rod.

U.S. Pat. No. 7,018,380 to Cole discloses a femoral intramedullary rod system. The rod system is capable of treating a variety of femoral bone fractures using a uniform intramedullary rod design. The system generally comprises an intramedullary rod defining an opening having an upper surface and a transverse member including a bone engaging portion and a connection portion defining a thru-hole with the nail sized to pass therethrough. A pin is selectively coupled to the transverse member to rigidly assemble the transverse member to the nail when the nail is passed through the thru-hole and the pin is received within the opening. In an alternative design, an epiphyseal stabilizer is joined to the nail by a locking member.

Also, U.S. Pat. No. 6,228,086 to Wahl et al. discloses a modular intramedullary nail. The intramedullary nail apparatus comprises a nail having a proximal portion, a middle portion and a distal portion. The proximal portion has a longitudinal slot adapted to receive at least one fixing element and the distal portion has at least one transverse bore. The proximal portion has a longitudinal axial bore. The apparatus further includes a set of inserts, each of which is adapted to be inserted in the longitudinal bore. Each insert has at least one guiding bore, the orientation and position of which is different for each of the inserts.

While devices and methods currently exist for repairing a fractured bone, there is need for an improved fractured fixation system. The welding system of the present invention may be used with a variety of fracture types and a variety of different bones. Also, with the inventive system, time and complexity of bone repair surgery is reduced. Furthermore, often times conventional bone plates and rods implanted in the emergency room are implanted with the intent of removing the plates and rods when more thorough bone reconstructive surgery can be performed. The trauma welding system of the present invention allows surgeons to quickly and thoroughly remove temporarily implanted plates, rods, and fasteners from fractured bones.

SUMMARY OF THE INVENTION

The trauma welding system of the present invention provides for the stabilization of tissue and implants during trauma surgery. The system includes devices and methods for intracorporeal bonding of thermoplastic material. An energy source welds the thermoplastics to polymers, metals, ceramics, composites, and tissue. The energy source may be resistive heating, radiofrequency, ultrasound (vibratory), microwave, laser, electromagnetic, electro shockwave therapy, plasma energy (hot or cold), and other suitable sources.

The trauma welding system utilizes any material weldable within the human body. This material requires the characteristic of becoming soft and tacky with the application of energy. The energy and the technique used to weld the material within the body avoid tissue necrosis. Such material may include polymers and some ceramics, composites, and metals. The present invention contemplates the use of any of these materials; however, based on testing, polymeric material, such as PEEK is a preferred weldable material. PEEK is advantageous because of its desirable characteristics of being softened, reheated, molded and remolded with ultrasonic energy.

In accordance with one aspect of the present invention, there is provided a method for stabilizing a fractured bone. The method includes the steps of positioning an elongate rod in the medullary canal of the fractured bone and forming a passageway through the cortex of the bone. The passageway extends from the exterior surface of the bone to the medullary canal of the bone. The method also includes creating a bonding region on the elongate rod where the bonding region is generally aligned with the passageway of the cortex, positioning a fastener in the passageway of the cortex and on the bonding region of the elongate rod, and thermally bonding the fastener to the bonding region of the elongate rod while the fastener is positioned in the passageway of the cortex.

In accordance with another aspect of the present invention, a second method for stabilizing a fractured bone is provided. The method includes positioning an elongate plate on the exterior surface of the fractured bone, forming a passageway extending through the elongate plate and into the bone, positioning a fastener in the passageway, and thermally bonding the fastener to the bone while the fastener is positioned in the passageway.

In accordance with a further aspect of the present invention, there is provided a third method for stabilizing a fractured bone. The method includes the steps of positioning an elongate rod in the medullary canal of the fractured bone and positioning an elongate plate on the exterior surface of the bone such that the cortex of the bone is positioned between the elongate rod and plate. The method also includes forming a passageway through the elongate plate and the cortex of the bone. The passageway extends from the exterior surface of the elongate plate to the medullary canal of the bone. The method further includes creating a bonding region on the elongate rod where the bonding region is generally aligned with the passageway, positioning a fastener in the passageway and on the bonding region of the elongate rod, and thermally bonding the fastener to the bonding region of the elongate rod while the fastener is positioned in the passageway.

The elongate rod, elongate plate, and fastener may include thermoplastic material such as PEEK. Ultrasonic energy may be used to thermally bond the fasteners of the present to the bonding region of the elongate rod and/or elongate plate. The bonding region may be a roughened surface, an indentation, a channel (blind hole), or a thru-hole in the plate/rod.

When bonding the fastener to the plate/rod, the fastener may also be thermally welded to one or more cortex areas (cortical bone portions) of the bone whereby the fastener resists movement between the bone and plate/rod. Also, the fastener and implants such as bone plates and IM rods may be thermally contoured to conform to an adjacent surface or configuration.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIGS. 3A-3K show exemplary embodiments of a welding horn;

FIGS. 4A-4C illustrate a three-function welding horn;

FIGS. 16A and 16B show a wedge-shaped expandable thermoplastic fastener;

FIGS. 17A and 17B illustrate a bulge-shaped expandable fastener;

FIGS. 23A-23D show the repair of a fractured bone with a thermoplastic rod;

FIGS. 25A and 25B show the repair of a fractured bone with a thermoplastic plate;

FIGS. 38A-38C illustrate a thermoplastic glenoid repair component;

DETAILED DESCRIPTION OF THE INVENTION

Figure 1:
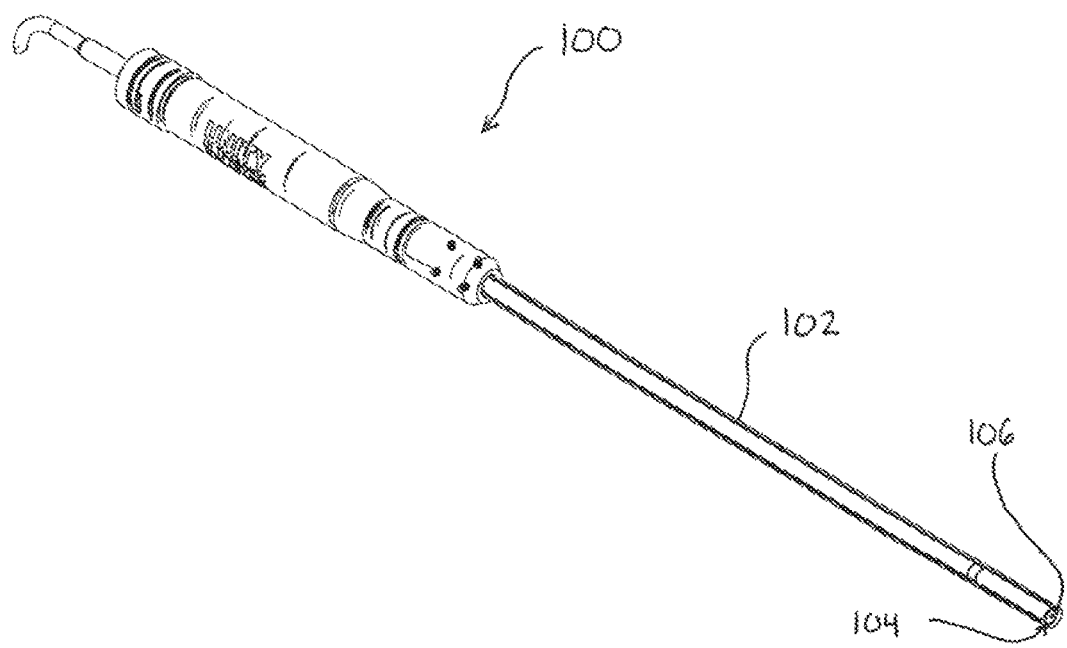
FIG. 1 is a perspective view of an exemplary ultrasound welding device.

The trauma welding system of the present invention provides for the stabilization of damaged tissue, such as fractured bones. The system includes devices and methods for intracorporeal bonding of thermoplastic material. An energy source welds the material in place. The energy source may be resistive heating, radiofrequency, ultrasound (vibratory), microwave, laser, electromagnetic, electro shockwave therapy, plasma energy (hot or cold), and other suitable sources. Other energy sources, surgical procedures, and medical instruments which may be used with the present invention are disclosed in U.S. Provisional Patent Applications Nos. 60/765,857 filed Feb. 7, 2006 and 60/784,186 filed Mar. 21, 2006. The contents of these documents are incorporated by reference herein in their entirety.

The trauma welding system of the present invention contemplates the use of any material weldable within the human body. This material requires the characteristic of becoming gel-like, tacky, and soft with the application of energy. The energy and the technique used to weld the material within the body avoid damage to surrounding body tissue. Such material may include polymers, ceramics, composites, and metals. The present invention contemplates the use of any of these materials; however, polymeric material is used to describe many of the following embodiments.

The polymers used in the present invention, such as PEEK, have randomly arranged molecules allowing vibrational energy to pass through the material with little attenuation. As such, the material requires relatively little ultrasonic energy to make the material soften and become tacky. This small amount of energy or heat needed to bond PEEK avoids tissue necrosis. The transition period is longer in duration and therefore, when applying energy, the material gradually softens, passing from a rigid state through a transition state to a rubbery state and then to a flowable gel-like state. The amorphous features of these materials make them ultrasonically weldable with lower temperature and better welding points. To bond these materials, the true melting point does not need to be reached or exceeded, so there is less risk to surrounding body tissue. PEEK is also useful with the welding system of the present invention because it has a modulus of elasticity very close to bone. Also, some grades of PEEK have a hydrophilic component which permits hydrophilic interlocking when placed in the body.

The temperature, time, pressure, and other parameters may be closely monitored and controlled to achieve an effective weld. Also, because the material does not substantially melt (only the welding region softens and becomes tacky) the holding strength of the thermoplastic during and after welding is not jeopardized. That is, a fastener made of a thermoplastic which melts, like those in the prior art, can not maintain a compressive force against a component or implant during the welding process. This is because the material of the fastener becomes liquefied, and a fastener in liquid form can not maintain a compressive or tension force. The present invention contemplates implants made of PEEK which bond by softening or making tacky the polymer material at the bonding region. The remaining PEEK material does not flow and therefore retains its ability to maintain a compression or tension force.

There are several factors that effect welding of thermoplastic materials. One is hydroscopicity, the tendency of a material to absorb moisture. If too much fluid gets between the welded parts it can decrease the bond or create a foam which prevents proper bonding of the materials. Therefore, the welding of thermoplastics may be performed under vacuum/suction, or a hermetic seal may be placed around the thermoplastic during the welding process. Also, the welding may be performed using a cannula which prevents fluid from entering the welding area. Furthermore, pressure, such as air pressure or compression force, may be applied during welding to prevent entry of moisture or liquid.

In addition to or in place of reducing moisture from the welding area, certain agents can be used to aid in the bonding process. Such agents may include filler material, glass filler, glass fiber, talc, and carbon. The agents may be placed at the bond site as a temporary welding enhancement means or may be a permanent agent to enhance the bonding. For example, the agent may be placed within the bonding region of PEEK. The agent may be left in place to bond or could be removed. It is contemplated that any amount of agent may be used to enhance the bond strength of the thermoplastics. In an exemplary embodiment, the amount of agent may be about 10 to 20 percent.

Moisture may further be eliminated or prevented from entering the thermoplastic material through the use of desiccants. Desiccants may be added prior to or during the welding process. Also, the thermoplastic material may be stored using desiccant material to prevent change in thermal properties. It is contemplated that this moisture reducing means may be applied to any polymeric material.

Another factor effecting the welding of thermoplastic material is pigments, especially white and black coloring. In many materials used in medical applications, white pigment is added to the polymer to make it appear sterile. Some pigments negatively affect the welding characteristics of the material. In the present invention, pigment-free thermoplastics, such as PEEK, are thermally welded for proper bonding of the material.

Mold release agents also affect the welding properties of thermoplastics. Polymeric components are usually formed in a mold to create a desired configuration. The component is easily removed from the mold because a release agent is placed between the mold and polymer. These agents, lubricants, plasticizers, and flame retardants negatively affect the bonding ability of the polymer. In the present invention, PEEK and other thermoplastics are free of these substances.

In addition to avoiding release agents, pigments, and moisture, the bonding of thermoplastic materials may be further enhanced by adding minute metallic material to the polymer. The metallic material may be metal flakes or metal dust. Examples of such metal include iron particles, chromium, cobalt, or other suitable metals. The metal may be embedded within the polymeric material to enhance the thermal properties. Alternatively, or in addition, the metal may be applied to the bonding surfaces of the polymeric material. Energy applied to the polymer would heat both the polymeric and metallic material providing a faster and more uniform weld. It is contemplated that glass fillers, carbon fillers, talc, or combination thereof may also be used in addition to or in lieu of the metallic material.

Other factors affecting the welding of thermoplastics include size, thickness, surface geometry, material properties of the thermoplastic, and the type of host tissue involved in the weld, i.e. soft, hard, dry, wet, or moist tissue. These and other factors are explained in more detail with reference to FIG. 5.

Furthermore, how the thermoplastic is welded is an important characteristic of obtaining a robust thermal bond. The type of energy used is one way to control the welding process. As previously mentioned, various energy sources may be used to weld polymers. In an exemplary embodiment and as used primarily throughout the invention, ultrasound energy is used to create vibrations within the polymeric material thereby exciting and heating the molecules to transition to a tacky state. Two or more different types of energy may also be used. For example, ultrasound may be used to weld a polymeric component to another component, while resistive heating may be used to contour the surface or change the geometry of the materials. The surface of the component may be smoothed out or sculpted using resistive heating.

The amount of power or watts used affects the weld. Therefore, the watts may be controlled by the operator depending on the component to be welded. A switch or dial may be placed in connection with the energy source to vary the amount of current supplied to the instrument. In an exemplary embodiment, the ultrasound power may be varied, for example, between 80 and 100 watts. The amount of time the energy is applied affects the weld as well. The time may be varied from milliseconds to hundredths of seconds to actual seconds depending on the desired weld. Controlling the time controls the amount and the degree of thermoplastic material which softens and becomes tacky. In an exemplary embodiment, energy may be applied from 0.1 seconds to 3 seconds, such as approximately 0.3 seconds. In case of RF and ultrasonic energy, the wavelength of the energy may be varied to affect the softening or melting of the thermoplastic. It is also contemplated that the amount of time that energy is applied may be controlled not only by the operator but also via radiofrequency, optical, radiowave, etc. A computer or other microprocessor may send signals to the energy emitter to turn the energy on and off. The energy may be pulsed (time, power, frequency, pressure, etc. may be pulsed) to enhance bonding and avoid tissue necrosis. That is, the energy may be emitted, then relaxed, then emitted, etc.

Controlling the pressure applied to the thermoplastic material also affects the welding process. During welding, a handpiece, an anvil, a horn, end effector, or combinations thereof may be used to apply controlled force against the polymer. After welding while the polymer is cooling, the force may continue to be applied to ensure proper bonding of the materials. The handpiece, anvil, horn, and end effector may be made of aluminum, titanium, or other suitable material. Also, the pressure may be varied, increased or decreased, during the welding process. In an exemplary embodiment, the pressure may be applied by the operator or may be applied with a spring. A sensor, spring, and/or piezoelectric device may be used to monitor and control the amount of pressure applied. In another exemplary embodiment, the welding horn may apply ultrasound energy and pressure to a polymeric implant being attached to bone. The bone may act as the anvil eliminating the need for an anvil instrument. Also, a hard implant or another polymeric material may function as the anvil.

Furthermore, the placement of the energy source on the thermoplastic affects the weld. The energy may be applied to one side of the polymer, through the center of the polymer, to two or more sides of the polymer, or to generally the outer surface of the polymer.

Controlling collapse is another factor in achieving an effective thermoplastic weld. A measurement of the change of the material being welded may be made to determine when bonding is complete. Also, by using a linear variable displacement transducer (LVDT), the control system can monitor the weld more precisely. Because a LVDT translates position to voltage, the weld profile can be dynamically controlled. For example, the initial energy delivered can be a higher wattage, then when the material starts to collapse the amplitude of the wave can be decreased. By being able to monitor the position of the collapse, different weld profiles can be programmed into the system. In addition, to control how far the material collapses on the anchor during a weld, a combination of weld current and time preset in the generator control system could be used. This can also be coupled with a defined force applied during the weld. Furthermore, collapse may be controlled or monitored through the use of a mechanical stop on the fixation device itself or on the welding instrumentation. The mechanical stop would prevent collapse after a predetermined point. It is also contemplated that the collapse could be monitored by other methods such as optics, laser, or even a hall-effect sensor.

All of the above-mentioned welding parameters may be monitored and controlled by a computer. Feedback may be provided by the computer to vary, start, and stop the various parameters of welding. The feedback and control of the computer may be programmed based on the type of polymer being welded and the type of material the polymer is being welded to. For example, for PEEK to PEEK welds, the computer applies a set of parameters (time, power, pressure, frequency, wavelength, etc.) to achieve an effective weld. For other polymers or for dissimilar material, the computer parameters may be changed.

Any known energy emitting instrument may be used with the surgical welding system of the present invention. The instrument may produce energy such as resistive heating, radiofrequency, ultrasound (vibratory), microwave, laser, electromagnetic, electro shockwave therapy, plasma energy (hot or cold), and other suitable energy. FIG. 1 illustrates an exemplary welding instrument of the present invention. The instrument 100 is an ultrasonic handpiece with a sheath 102 to cover and protect the end effector 104 and hold a fastener. The sheath 102 has a small counter bore at its tip to cover a portion of the cap. There is also a bushing at a nodal point of the ultrasonic signal to prevent the end effector 104 from contacting the sheath 102. The tip of the end effector 104 has a small post 106 sticking out of the welding face which presses into a bore in the cap of the fastener. This can help align the fastener post into the anchor bore and keep the cap tight against the end effector face. After welding, the end effector 104 easily pulls off.

The post 106 on the end effector 104 may be threaded or have a Morse taper to mate with the cap. Alternatively, the end effector 104 has a bore that the top of the cap mates into. The mating of the components could also be by threads or a Morse taper along with a straight post. Furthermore, the post could be roughened on the outside surface for better adhesion.

Figure 2A:
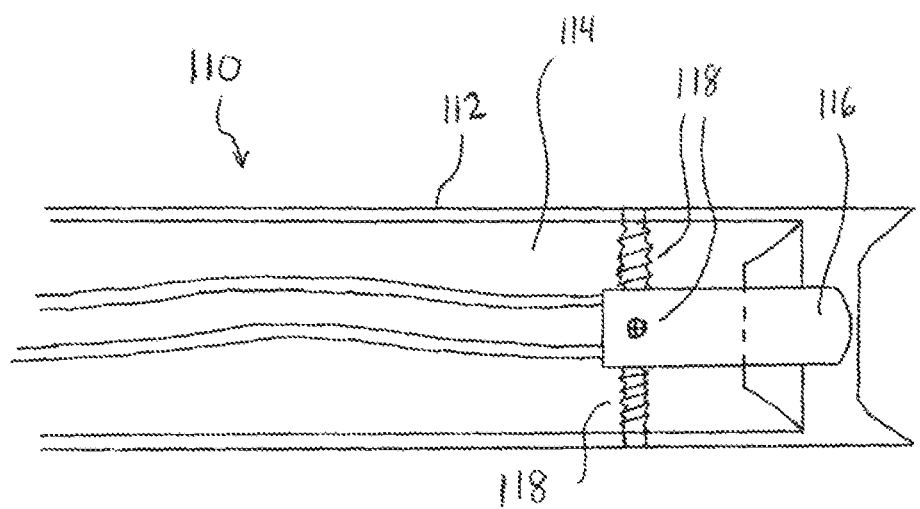
FIGS. 2A and 2B illustrate exemplary cartridge heaters of the present invention.
Figure 2B:
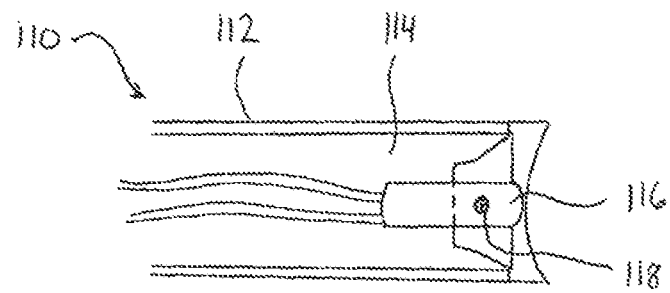

Another exemplary instrument is illustrated in FIGS. 2A and 2B. A small cartridge heater 110 may be used to deliver thermal energy. The heater 110 may be a SUNROD ⅛ inch cartridge heater. To prevent heat build up of the outside shaft 112, an air barrier 114 may be formed between the welding horn 116 and the shaft 112. In FIG. 2A, four set screws 118 are used to create the air barrier, while in FIG. 2B, a single set screw 118 is used.

Figure 3A:
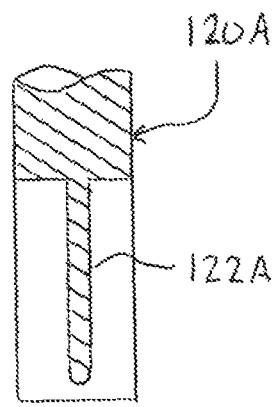
Figure 3B:
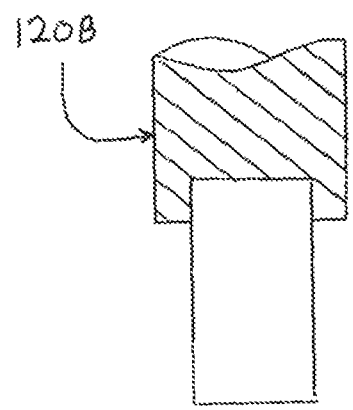
Figure 3C:
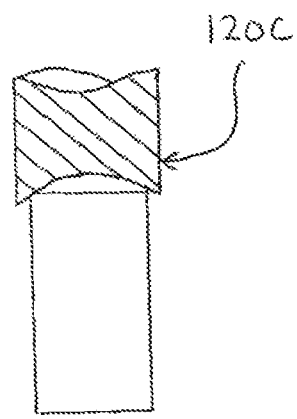
Figure 3D:
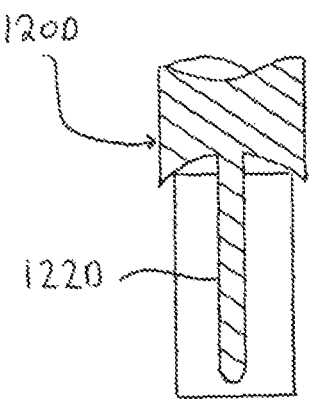
Figure 3E:
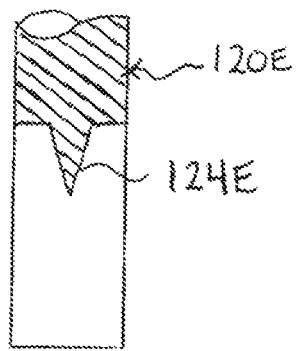
Figure 3F:
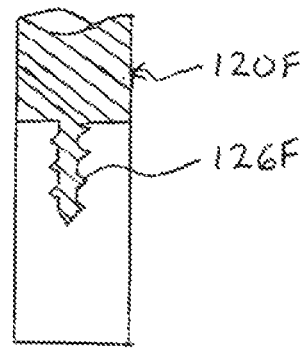
Figure 3G:
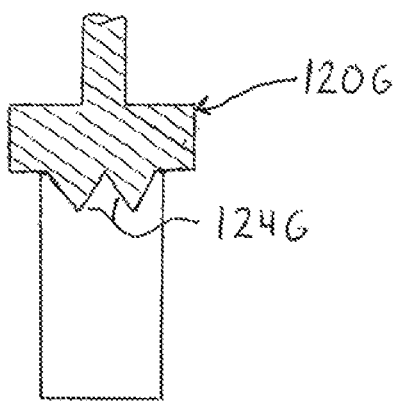
Figure 3H:
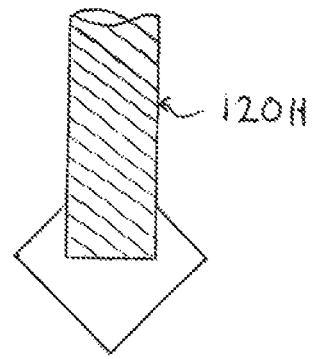

Referring to FIGS. 3A-3K, energy emitting instruments include various horn or end effector configurations. In FIG. 3A, the horn 120A emits energy to the top surface of the implant as well as the central core via an elongate extension 122A. The horn 120B of FIG. 3B is recessed to hold the thermoplastic implant during welding. In FIG. 3C, the horn 120C is concave to provide a rounded surface to the implant after welding. The horn 120D of FIG. 3D is concave and includes a central extension 122D to deliver energy throughout the implant. In FIG. 3E, the horn 120E includes a spike 124E which is disposable within an implant. The horn 120F of FIG. 3F includes a threaded pin 126F which is received by a bore in the implant. In FIG. 3G, the horn 120G includes dual spikes 124G. The distal portion of the horn 120H of FIG. 3H is dimensioned to fit within the thermoplastic implant. In FIG. 3I, a sleeve 128I is disposed about the horn 120I and implant. The side-weld horn 120J is shown in FIG. 3J. In FIG. 3K, a dual horn welder 120K is used to simultaneously weld two fasteners 130.

In FIGS. 4A-4C, a welding instrument 140 is shown which includes three different horn or end effector configurations in one design. The instrument 140 includes a bonding-surface horn, a welding horn, and a contouring horn. FIG. 4A shows the instrument 140 in the bonding-surface horn configuration. The center shaft 142 is extended distally from the instrument 140, and the outer shaft 144 which slides over the center shaft 142 is also extended distally. In FIG. 4B the outer shaft 144 has been retracted into the welding instrument, leaving only the center shaft 142 extended. In this position, the instrument 140 is in the welding horn configuration. Finally, FIG. 4C shows both the center and outer shafts 142 and 144 retracted into the instrument. The sheath 146 which surrounds the instrument 140 has also been retracted. In this position, the instrument 140 is in the contouring horn configuration. The distal surface 148 of the contouring horn may be used to reshape a thermoplastic implant, such as the head of a fastener.

In use, the instrument of FIGS. 4A-4C may be reconfigured quickly by the operator during a welding operation. In the bonding-surface configuration, the instrument is positioned such that the distal portion of the extended center and outer shafts come in contact with a thermoplastic component or implant. Energy, such as ultrasonic energy, is emitted from the center and outer shafts to create a roughened surface on the implant, to create an indentation or blind hole in the implant, or to create a through hole in the implant. The type of fixation desired and the intended fastener to be used will determine how deep the bonding-surface horn should be moved into the implant. With the bonding surface formed, the outer shaft is retracted into the instrument. The distal portion of a fastener is placed in or on the bonding surface of the implant, and the end effector is placed on the fastener with the center shaft extending into a bore in the fastener. Using the desired welding parameters, the operator emits ultrasonic energy from the end effector to bond the fastener to the implant. Once welded, the fastener may be contoured or reshaped or resized with the contouring-horn of the instrument by retracting the center shaft and optionally retracting the sheath around the instrument.

Figure 5:
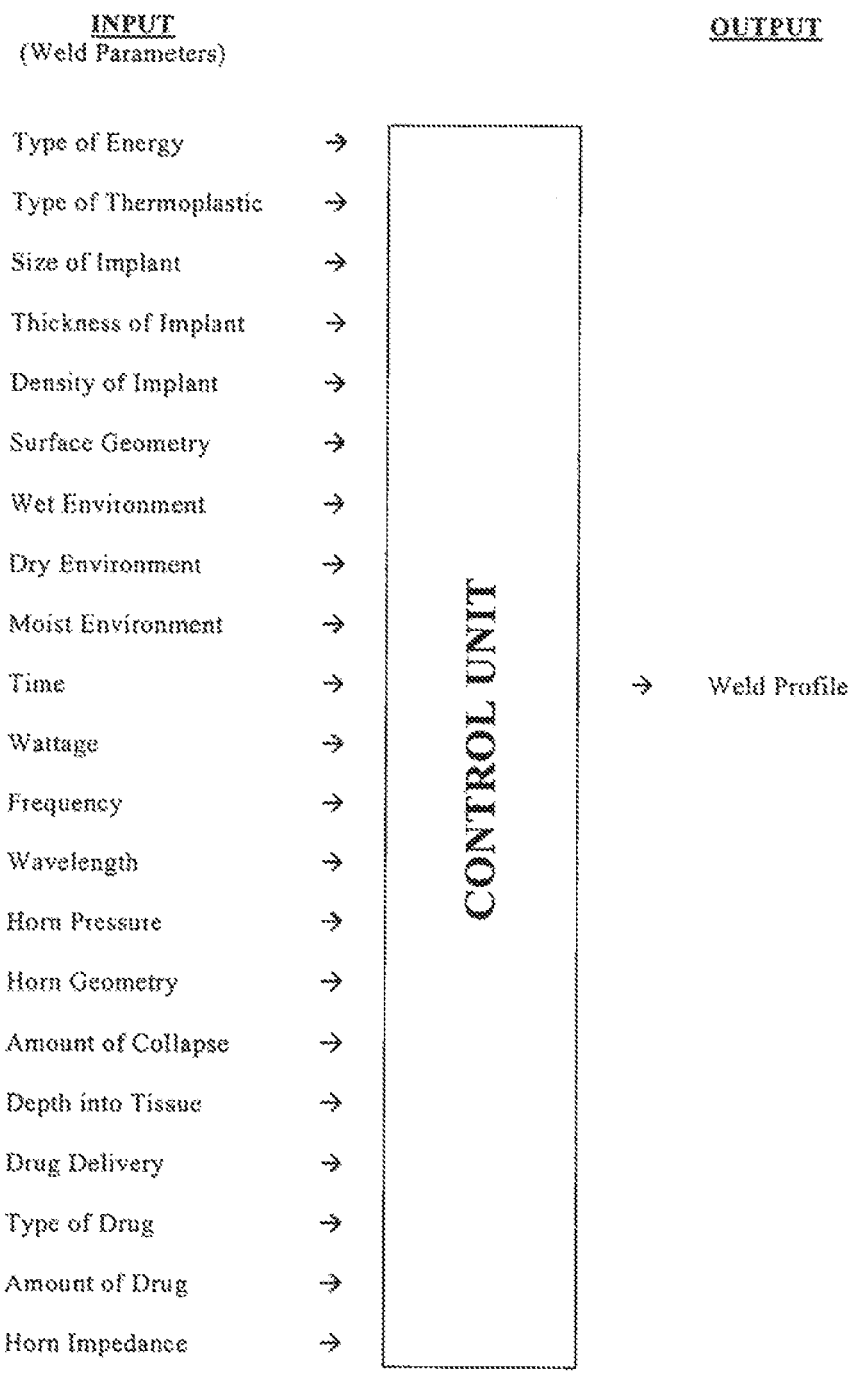
FIG. 5 shows the input parameters of a welding control unit.

As previously mentioned, monitoring and controlling the welding parameters ensures proper bonding of thermoplastics. FIG. 5 illustrates the various parameters that may be monitored and controlled for the trauma welding system of the present invention. The parameters include, but are not limited to, the type of energy to emit, type of thermoplastic material, the size and configuration of the implant, the thickness of the implant, implant surface geometry, the aqueous environment, weld time, weld power, frequency and wavelength of the energy, amount of pressure applied to the implant during and after welding, the geometry of the weld horn, the impedance of the welding horn, the density of the implant, the amount of collapse of the thermoplastic material, the depth into tissue the implant is to be inserted, and the type and amount of any therapeutic agent that may be delivered.

Figure 6:
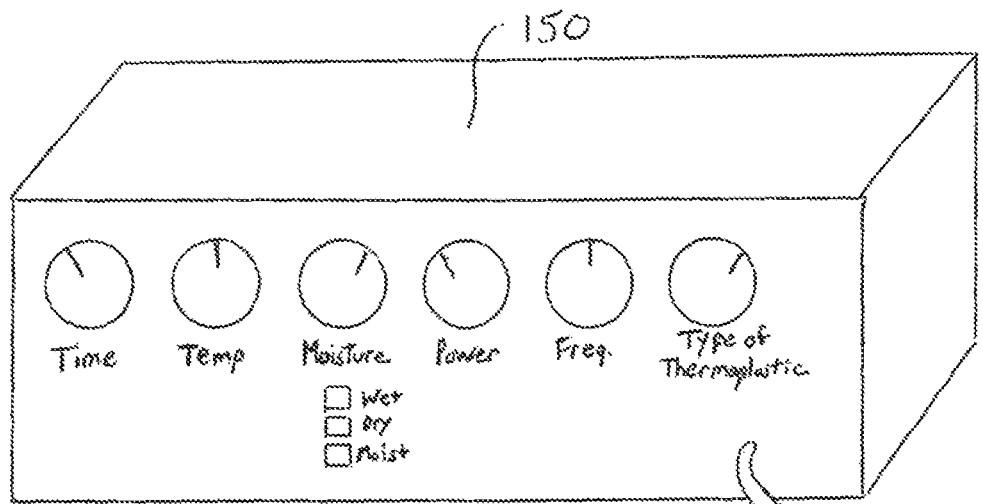
FIG. 6 illustrates a manual welding control box.
Figure 7:
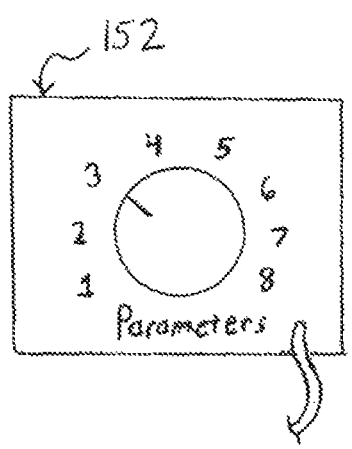
FIG. 7 shows a control box having pre-set welding parameters.

FIG. 6 shows a manual welding control box 150. A surgeon determines the optimum welding parameters and enters them into the control box 150 prior to welding. In FIG. 7, an automatic control box 152 includes pre-set weld parameters. For example, preset 1 may be for implant A which has a known material, size, etc. to be welded in a dry environment. Preset 2 may be for implant A in a moist environment. Preset 3 may be for implant A in a wet environment. Preset 4 may be for implant B using energy source X. Preset 5 may be for implant C using energy source Y. Preset 6 may be implant D using energy source Z. It is contemplated that any combination of weld parameters may be pre-set into the control box.

Figure 8:
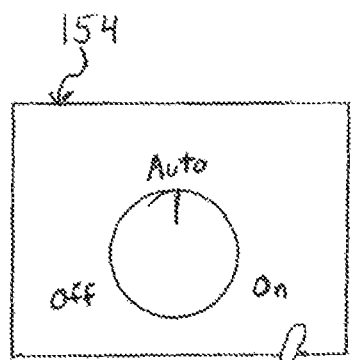
FIG. 8 illustrates an automatic welding control unit.

The control box 154 of FIG. 8 is automatic. A sensor on the end effector 156 determines the weld parameters when the horn is placed adjacent the thermoplastic material. The sensor 156 picks up material type, humidity of the environment, and any other parameter, then sends the data to the control box. The control box 154 automatically selects the energy source, time, wattage, and any other parameters.

The exemplary energy control units previously described may be used to select and vary any of the welding parameters. For example, the power or wattage of the welding horn may be varied over time. During a first period of welding, a large amount of energy may be delivered to overcome heat sink. In the second period, the energy may be reduced. In a subsequent period, the energy may be maintained at an appropriate level to thermal weld an implant.

To ensure a properly executed weld, the welding instrument of the present invention provides a positive feedback system. One way to provide user feedback is by measuring and controlling the impedance (resistance) of the end effector or weld horn. This feedback system is based on the fact that the load placed on the end effector affects the impedance of the system. That is, the pressure put on the end effector by the object to be welded changes the resistance of the end effector. To determine the handpiece or end effector impedance, the drive voltage and current through the end effector may be monitored during the weld. By using Ohm's Law V=IR, the impedance, R, may be calculated from the voltage, V, and current, I.

Figure 9:
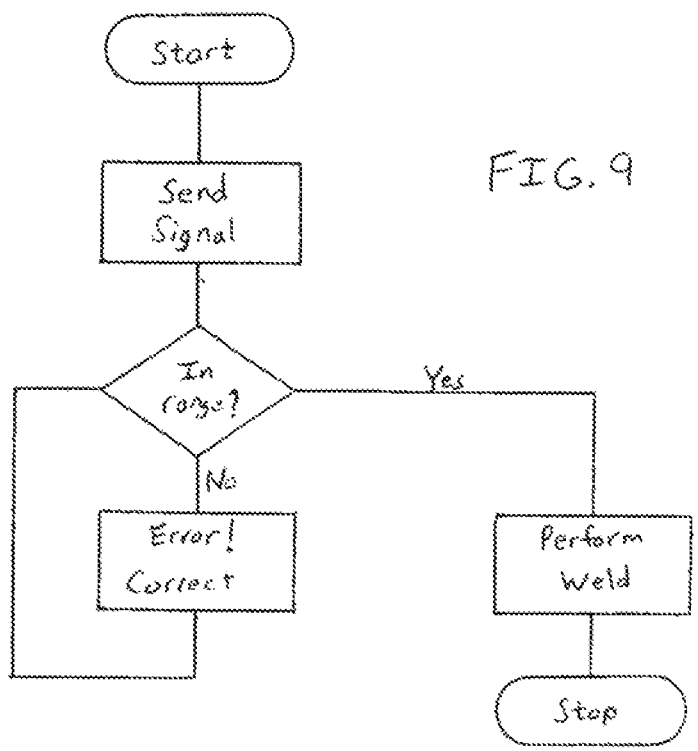
FIG. 9 is a flowchart showing the steps for adjusting the welding device.

FIG. 9 illustrates one method of ensuring a consistent weld. By first transmitting a low power ultrasonic signal through the end effector, the impedance of the handpiece can be measured with no pressure. This establishes a baseline impedance for the end effector. Then, the end effector may be subjected to known pressures, and the voltage and current may be measured to calculate the impedance for each pressure. Therefore, when a surgeon or other operator applies pressure from the end effector to a thermoplastic implant to be welded, the actual amount of pressure is fed back to the operator because the pressure corresponds to a known impedance. The surgeon may increase or decrease the pressure on the end effector until the desired pressure is achieved. With the correct pressure applied, the surgeon may activate the handpiece and emit ultrasonic energy in accordance with the calculated weld profile.

In another exemplary embodiment for providing positive feedback, the pressure and impedance of the end effector may be monitored throughout the weld profile. In the previously described method, the proper pressure based on impedance was achieved by the surgeon using a low power signal, and then the ultrasonic energy was emitted from welding. In this method, the pressure and impedance is measured during the weld. When pressure on the end effector is applied and the weld is started, for example by a hand control or footswitch, the current may be measured and the impedance calculated by a microprocessor. When the impedance is too high or too low or outside an acceptable range indicating an incorrect applied pressure, the microprocessor may send an audible or visual signal to the surgeon. Alternatively, or in addition to the signal, the microprocessor can stop energy emission until the correct pressure and impedance is achieved, then the welding may be resumed either automatically by the microprocessor or manually by the surgeon.

Figure 10:
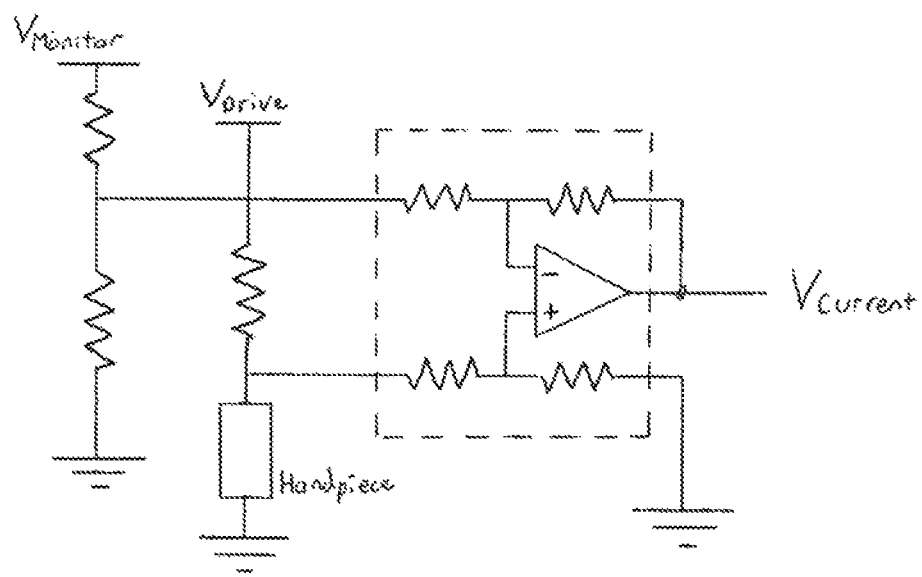
FIG. 10 is a diagram showing an electrical circuit for checking the welding device.

Referring FIG. 10, because the drive signal is sinusoidal, $V_{monitor}$ and $V_{current}$ must be sampled at a rate that is at least twice the frequency of the ultrasonic waveform. For example, if the waveform is a 41 kHz sinusoid, then samples may be taken at 328 kHz, or one sample every 3 µs. In this example, solving for the impedance, the handpiece would be 500Ω.

Also, by monitoring handpiece impedance, changes to the weld environment, such as moisture, ambient temperature, aqueous conditions, etc., may be automatically compensated for by adjusting the drive waveform of the ultrasonic energy. For example, if for a certain material it is determined that 80 W of power is required for a 400 ms period to achieve a consistent weld, then the waveform can be adjusted do ensure that this amount of energy is constantly delivered. Power is calculated using P=IV, but because the signal from the waveform is sinusoidal, the root mean square (RMS) voltage as $V=(1/\sqrt{2})A$ must be used.

As the impedance, R, of the handpiece changes, the total power delivered also changes. By increasing or decreasing the drive voltage to compensate for the change in the impedance, a constant power can be delivered.

In another exemplary method, seat collapse may be monitored by SONAR. Seat collapse is the distance a thermoplastic fastener or implant shrinks in height when ultrasonic energy is applied. Generally, thermoplastic fasteners may shrink about 20 percent in height and increase 30 percent in width when welded. For fasteners having two pieces, such as a cap and an anchor, the attenuation of the reflected ultrasonic waves changes as the two piece fastener becomes one piece. This change in attenuation may be monitored to alert the surgeon or operator when the weld is complete. Furthermore, an ultrasonic transducer could be used in conjunction with the end effector to detect the change in acoustic impedance/attenuation of the weld site. This signal may be monitored by a microprocessor/controller or data signal processor (DSP) and data may be automatically interpreted to indicate whether the weld was successful.

Another way of providing feedback of an effective weld is to monitor the Eddy currents created by the movement of the end effector. As the end effector vibrates, the linear motion creates a change in the magnetic field. By monitoring the travel of the end effector, the amount of collapse can be determined.

It is also contemplated that the material being welded may be translucent or transparent, and a visual indicator within the material could indicate when the weld is complete. For example, a pigment, dye, or other substance may be impregnated into the thermoplastic which when subjected to ultrasonic energy the pigment or dye would be released indicating that the weld is complete. Alternatively, the material of the thermoplastic may have the characteristic of changing color as heat, vibrations, or ultrasonic energy is applied for a predetermined time and a predetermined frequency and wattage.

The previously described methods for providing positive feedback to the weld operator included the use of measurements and/or computers. Another positive feedback system is provided which relies on physical force. When two objects are fastened to each other, it is common for the technician or mechanic to pull or tug on the assembly to ensure the parts are securely fastened. This common technique may apply to the thermoplastic welding system of the present invention. Once a fastener or other implant is ultrasonically welded, the surgeon can apply a quick tug on the assembly to verify the weld was completed as intended.

Figure 11A:
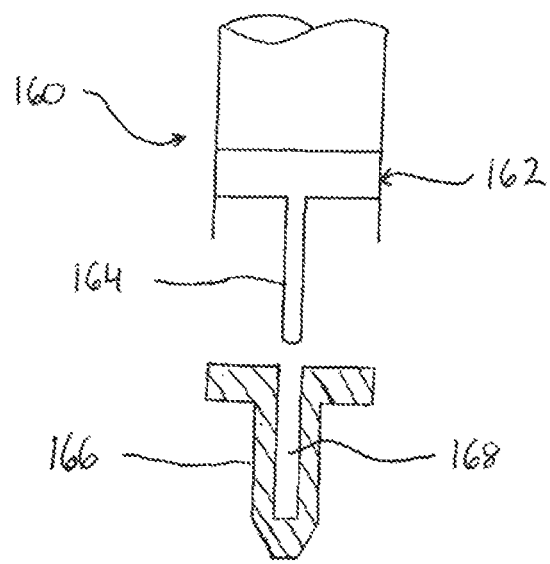
FIGS. 11A and 11B illustrate a physical positive feedback device.
Figure 11B:
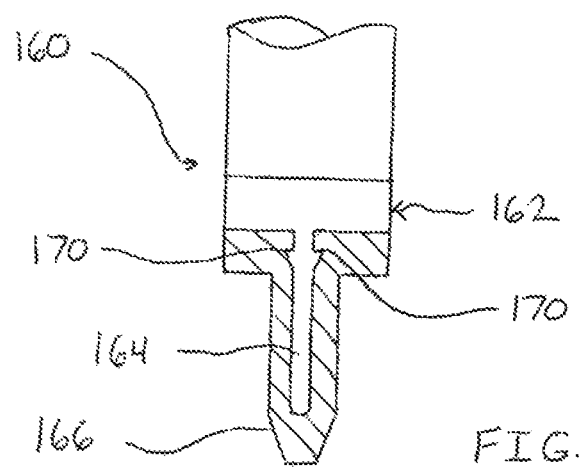

FIGS. 11A and 11B illustrate a feedback instrument 160 for performing such a physical positive feedback check. An end effector 162 includes a post 164 which emits ultrasonic energy. A thermoplastic fastener 166 is placed on the end effector 162 with the post 164 in a bore 168 of the fastener 166. After emitting ultrasonic energy and welding the fastener to an implant or tissue, the surgeon actuates a biasing prong or prongs 170 from the post 164 of the end effector while the post 164 is still in the fastener 166. In a stored configuration, the prongs 170 are positioned within the post 164. In a deployed configuration, the prongs 170 extend radially from the post 164 by the activation of a handle, switch, or button. The extended prongs 170 dig slightly into the material of the fastener 166 so that the surgeon may now pull or tug on the instrument 160 proximally to verify that the fastener 166 is securely welded in place. Additionally, the prongs and/or post may include a strain gauge or other force measuring device to measure and display to the surgeon how many pounds of pull strength is being put on the fastener.

Figure 12A:
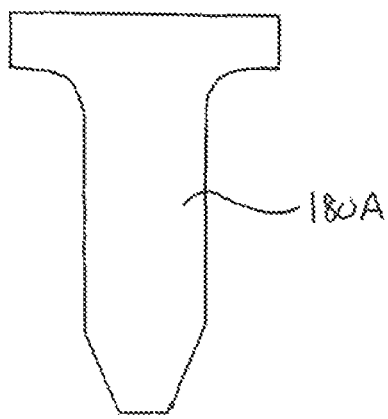
FIGS. 12A-12F show various embodiments of thermoplastic fasteners.
Figure 12B:
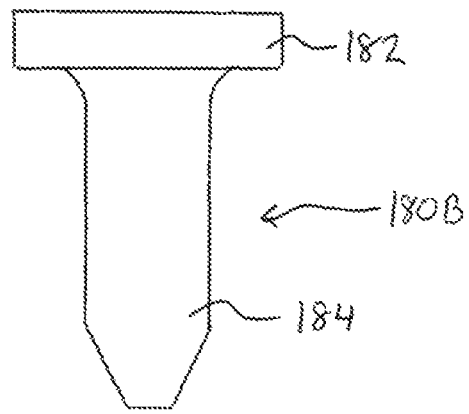
Figure 12C:
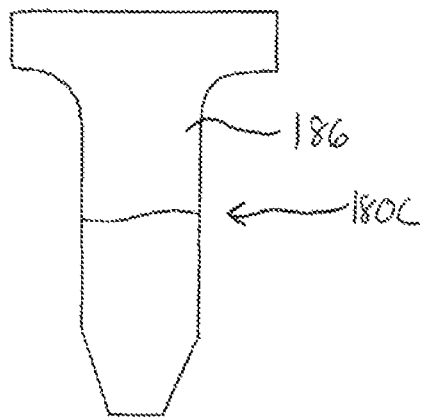
Figure 12D:
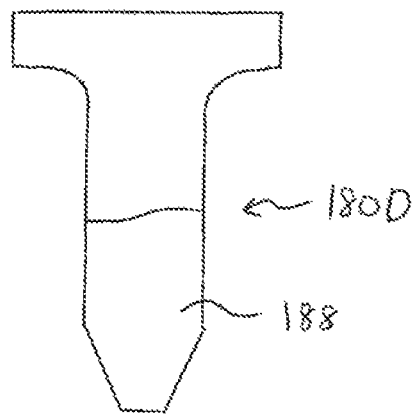
Figure 12E:
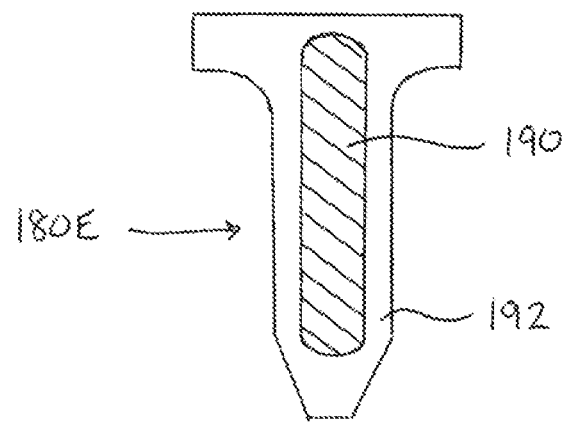
Figure 12F:
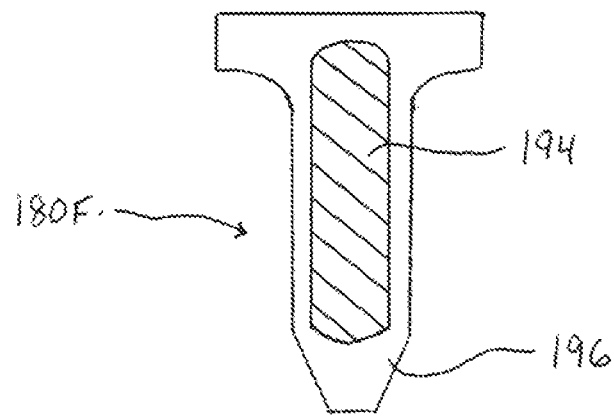

Some exemplary fasteners of the present invention are illustrated in FIGS. 12A-12F. The fastener 180A of FIG. 12A is made entirely of a thermoplastic material such as PEEK. In FIG. 12B, the fastener 180B includes one type of thermoplastic material in the lid 182 and a different type of thermoplastic material in the post 184. Each material may have different welding properties. FIG. 12C shows a fastener 180C with only a proximal portion 186 made of PEEK, while FIG. 12D illustrates a fastener 180D with only a distal portion 188 made of PEEK. In FIG. 12E, the fastener 180E includes a rigid metallic core 190 which is enclosed by a thermoplastic 192. The fastener 180F of FIG. 12F has a polymeric core 194 surrounded by PEEK 196. Although not illustrated in these examples, the fasteners may include a central bore for receiving the post of the end effector.

Figure 13A:
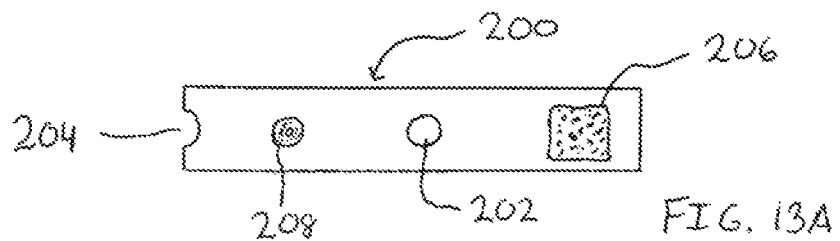
FIGS. 13A and 13B illustrate bonding regions of implants.
Figure 13B:
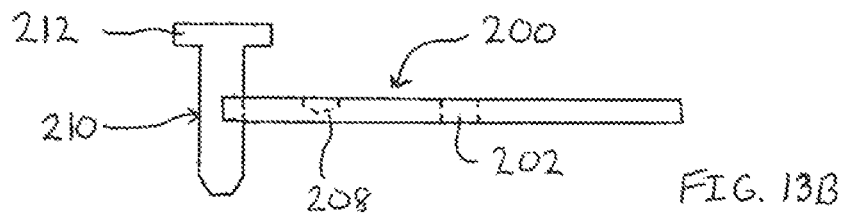

FIGS. 13A and 13B show a bone plate or rod 200 for use with the trauma welding system of the present invention. Plate or rod 200 may be free of holes or may include pre-drilled thru-holes 202 or edge-holes 204 for positioning fasteners therethrough. The holes may be formed by the manufacturer at the factory or by the surgeon in the operating room. The plate or rod 200 may include a roughened surface 206 in some areas or over the entire surface. The roughened areas 206 provide a bonding region for fasteners or other thermoplastic implants. Additionally, the plate 200 may include blind holes 208 for securing a fastener therein. The blind hole 208 is an indentation in the surface of the plate 200 which extends only partially into the plate 200. The thru-hole, roughened area, and blind hole are bonding regions. In FIG. 13B, a thermoplastic fastener 210 is positioned in an edge-hole 204 of the plate 200. The distal end of the fastener 210 may be seated in another implant or tissue, such as bone. Because the plate includes the edge-hole, the fastener may be first at least partially implanted, then the edge-hole of the plate may be positioned around the fastener. Once properly aligned, the plate 200 and fastener 210 may be welded together and the proximal end or head 212 of the fastener 210 may be contoured as desired.

Figure 14A:
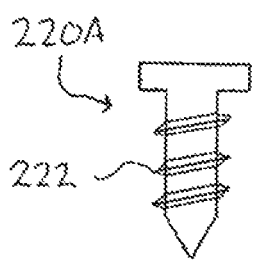
FIGS. 14A-14D show more embodiments of thermoplastic fasteners.
Figure 14B:
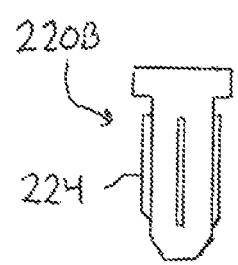
Figure 14C:
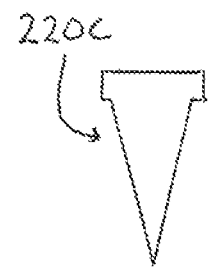
Figure 14D:
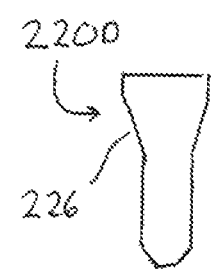

In addition to the fasteners described in FIGS. 12A-12F, other fastener configurations are illustrated FIGS. 14A-14D. In FIG. 14A, the fastener 220A includes a mechanical locking mechanism in addition to thermal bonding. The fastener 220A includes thermoplastic material and includes helical threads 222 disposed on the outer surface thereof. In FIG. 14B, the fastener 220B includes longitudinally extending edges 224. These edges 224 may function as energy directors to focus the ultrasonic energy along the edges providing a secure bond to tissue or an implant. FIG. 14C illustrates a wedge shaped or Morse taper fastener 220C. The fastener 220D of FIG. 14D includes an angled shoulder 226 which may be seated against an implant or tissue and thermally bonded in place.

Figure 15A:
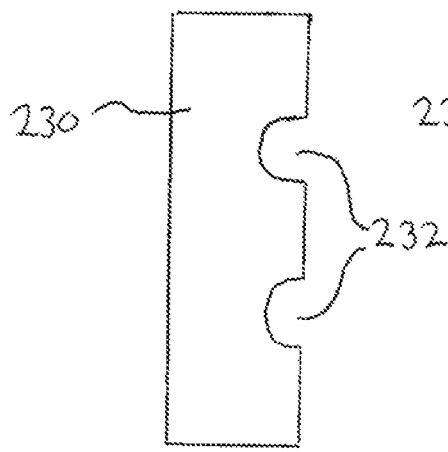
FIGS. 15A and 15B illustrate notched plates and rods for stabilizing bones.
Figure 15B:
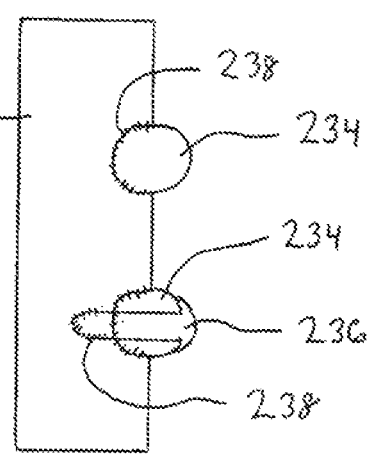

The combination of thermoplastic material and ultrasonic energy of the present invention is advantageous for modifying and preparing implants while the implants are in the body. In FIG. 15A, a plate 230 may be positioned against bone to stabilize a fractured bone or damaged vertebrae. With the plate in place, a notch or nest 232 may be cut using heat energy or other mechanical means such as a drill or saw. The notches 232 are dimensioned and configured to receive a rod 234 or fastener. Therefore, implanting and thermally bonding a rod in the notch 232 creates a desired geometric shape with the plate 230 and rod 234 extending generally perpendicular to each other. In this configuration, the assembly may be used to stabilize the spinal column or may function as a combination internal-external fracture bone stabilizer. In the latter case, a first plate may be positioned against the fractured bone, while an exterior plate may be bonded to one or more rods extending from the notches of the first plate. The first plate provides internal fixation, and the exterior plate provides external fixation. The rods bonded between the two plates function as pins passing through the skin and other soft tissue. To further secure a rod within the notch of the plate, a fastener 236 may be inserted as shown in FIG. 15B. The plate 230, rod 234, and fastener 236 are thermally welded at several bonding regions 238.

The thermoplastic fasteners of the present invention may also be expandable. FIGS. 16A and 16B illustrate one embodiment of a fastener 240 which includes a cap 242 and an expandable anchor 244. The anchor 244 is generally V-shaped or conical, convex shaped. The anchor 244 may include a tissue-piercing distal tip 246 to penetrate into and through tissue and implants, such as plates or rods. As seen in FIG. 16A, the anchor 244 includes a bore 248 that tapers down from the proximal end to the distal end. The bore 248 is dimensioned and configured to expand when receiving the post 250 of the cap 242. Therefore, the post 250 tapers from the proximal end or head down to the distal tip. The distal tip of the post 250 may also include a tissue-piercing end. In an exemplary method of use, the expandable anchor 244 is inserted through a layer of tissue 252. A plate or other implant 254 (or other tissue) is placed adjacent the tissue 252. The post 250 of the cap 242 is moved distally through the plate 254 and tissue 252 and into the bore 248 of the anchor 244 causing the anchor to expand outwardly or radially, as shown in FIG. 16B. With the head 256 of the cap 242 pressing the plate 254 against the tissue 252, the cap 242 is ultrasonically welded to the anchor 244. The anchor is prevented from being removed from the tissue because the expanded wall portions of the anchor contact the underside of the tissue.

FIGS. 17A and 17B illustrate another expandable fastener 260 embodiment. The principle of insertion and expansion are similar to the fastener of FIGS. 16A and 16B. However, in this embodiment, the anchor 262 is generally cylindrical in shape. The anchor 262 has a cylindrical bore therein. The cap 264 includes a post 266 which is generally cylindrical and has a widened portion disposed between a proximal portion and a distal portion. The diameter of the distal portion of the post 266 is configured for initial insertion in the bore 268 of the expandable anchor 262. The diameter of the widened portion is configured such that it expands the walls of the anchor 262 radially outward as the cap 264 is moved distally into the anchor 262. In a seated configuration, the cap 264 is ultrasonically welded to the anchor 262 and the head 270 of the cap 264 holds a plate or tissue 272 against lower tissue 274. The expanded walls of the anchor contact the lower tissue preventing the fastener from being pulled out.

Figure 18A:
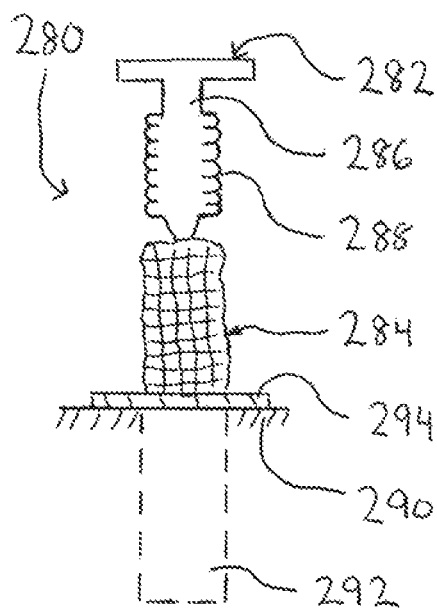
FIGS. 18A and 18B show a mesh expandable fastener.
Figure 18B:
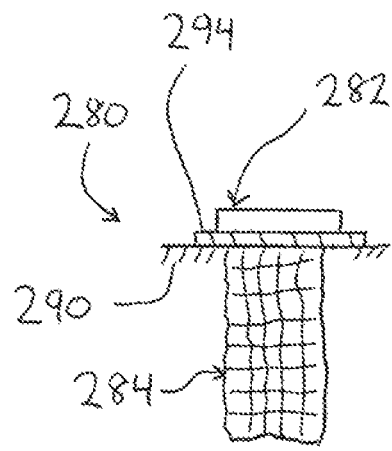

Referring to FIGS. 18A and 18B, the fastener 280 includes a cap 282 and an anchor 284 which is configured as a tubular mesh. The tubular mesh 284 has an unexpanded diameter and an expanded diameter. The post 286 of the cap 282 is dimensioned to fit within the lumen of the tubular mesh 284 to expand the mesh to its expanded diameter. The post 286 may include ridges or ring-like structures 288 disposed thereon to aid in the expansion of the tubular mesh anchor 284. In an exemplary method of use, the anchor 284, in its unexpanded diameter, is positioned in tissue 290. A hole 292 may be drilled into the tissue 290 for receiving the anchor 284 if desired. A bone plate or other implant 294 is placed adjacent the bone 290. The cap 282 is moved through the plate 294 and tissue 290 and into the lumen of the mesh 284.

The mesh achieves its expanded diameter in at least one of two ways. First, the insertion of the post (with ridges) into the mesh causes the mesh to expand thereby preventing the anchor from pulling out of the tissue. Alternatively, the post with or without ridges may be inserted into the lumen of the mesh while the mesh maintains its unexpanded diameter. Ultrasonic energy and pressure from the welding horn may be applied to the cap causing it to swell thereby locking the anchor into the tissue. It is also contemplated that a combination of expansion methods may be used. That is, the post with ridges may be inserted into the lumen of the mesh causing the anchor to expand. Then, ultrasonic energy may be applied to the fastener to further expand the mesh and bond the cap to the anchor.

Figure 19A:
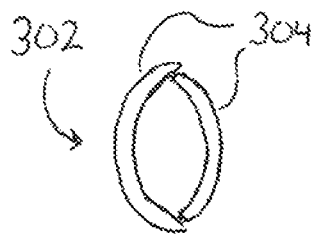
FIGS. 19A and 19B illustrate a tube-shaped expandable fastener.
Figure 19B:
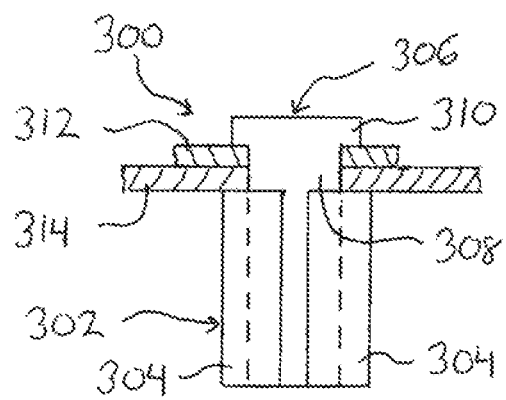

Another embodiment of an expandable fastener 300 is illustrated in FIGS. 19A and 19B. A top or bottom view of the anchor 302 is shown in FIG. 19A. The anchor 302 includes two or more arced members or longitudinal portions of a tube 304. When placed together as in FIG. 19A, the anchor 302 is in an unexpanded configuration. The cap 306 includes a post 308 and lid 310. To fasten a bone plate or other implant 312 to tissue 314, the anchor 302 in its unexpanded configuration is inserted into the tissue 314. The post 308, which may include a tissue-piercing point, is inserted through the plate and tissue. As the post 308 enters the anchor 302, the arced members 304 are moved outwardly or radially. This is possible because the inner bore diameter of the anchor 302 in its unexpanded configuration is smaller than the diameter of the post 308 of the cap 306. Once the cap 306 is pressed into the anchor 302, it is ultrasonically welded to the anchor 302. The anchor and fastener are prevented from being pulled out of the tissue because the proximal ends of the expanded arced members of the anchor contact the tissue. The lid of the cap holds the bone plate firmly against the tissue.

Figure 20A:
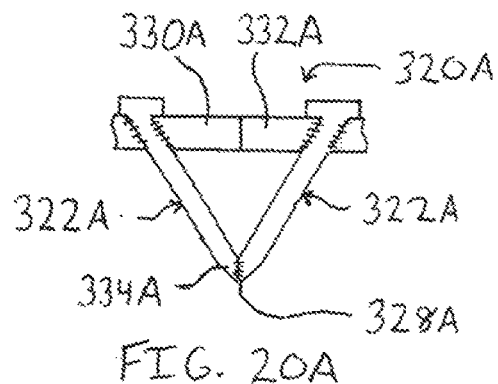
FIGS. 20A-20E show triangulation fasteners.

The trauma welding system of the present invention also provides fasteners configured as triangulation staples. Examples of these staples are illustrated in FIGS. 20A-20E. In FIG. 20A, the staple 320A includes first and second nails or braids 322A. The nails 322A include a long post and a head disposed on the proximal end of the post. The head may be slanted, angled, or pivotable to allow the head to seat flush against an implant or tissue. The distal end of the post includes a tissue-piercing tip 328A. The nails 322A may include a central bore configured for receiving an end effector. As shown, the fastener 320A includes two nails; however, it is contemplated that the triangulation staples of the present invention may include three or more nails. The staple 320A of FIG. 20A is shown holding two bone plates or other implants 330A and 332A against each other at their edges. The first nail 322A is inserted through the first plate 330A near the edge of the first plate. The first nail 322A is angled generally between 30 and 60 degrees with respect to vertical. A second nail 322A is inserted through the second plate 332A near the edge of the second plate. The second nail 322A is also angled such that the distal tips 328A of the first and second nails contact each other. Ultrasonic energy is applied to the nails 322A to bond the distal tips 328A together to form a bonding area 334A. The nails 322A may also be welded to the plates 330A and 332A where the nails passed through the plates. Additionally, the edges of the bone plates may be ultrasonically welded together. When implanted, the staple 320A securely holds the two plates 330A and 332A together and fastens the plates to tissue, such as bone.

Figure 20B:
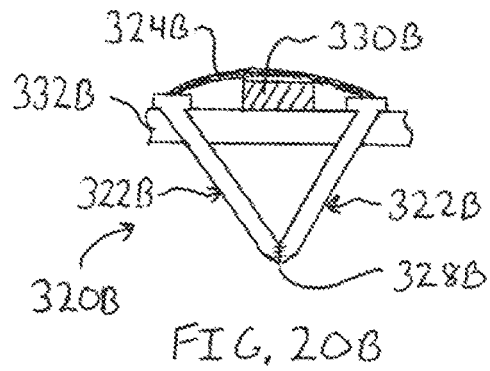

In FIG. 20B, the triangulation staple 320B includes two nails 322B with a suture or cable 324B connected with the heads of the nails. In an exemplary use of this staple configuration, an implant 330B is positioned adjacent another implant or tissue 332B. The first nail 322B of the staple is inserted into the tissue 332B on one side of the implant 330B. The second nail 322B is inserted into the tissue 332B on another side of the implant 330B. The cable 324B, spanning between the nails, contacts the implant 330B. As the nails 322B are driven further into the tissue 332B, the cable 324B tensions and presses the implant 330B against the tissue 332B. Also, with the nails firmly implanted in the tissue, the distal tips 328B of the nails 322B contact each other. Ultrasonic energy may be used to weld the distal tips 328B together to form a bonded region.

Figure 20C:
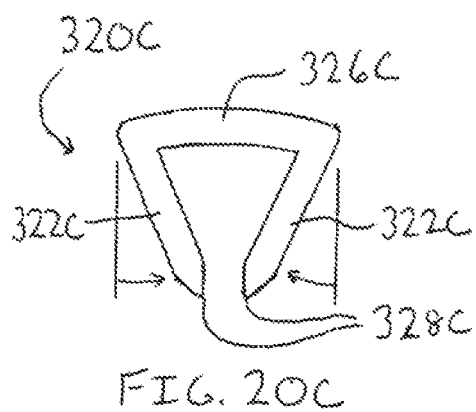

The triangulation staple 320C of FIG. 20C is a one-piece design. The first and second nails 322C are connected to each other by a cross member 326C attached at the proximal ends of the nails. The nails 322C may be rotatable or pivotable from their connection with the cross member 326C. The distal ends of the nails may include tissue-piercing tips 328C. In a pre-implantation configuration, the nails 322C extend generally perpendicular to the cross member 326C. In use, the staple 320C is inserted through tissue, an implant, or both. The staple is inserted with the nails 322C being generally perpendicular to the cross member. Once positioned, the nails 322C may be pivoted such that the distal tips of the nails contact each other. The rotation of the nails 322C may be performed by an instrument designed to angle the nails, for example by using the central bore therein. With the tips in contact, the nails 322C may be ultrasonically welded together to form a secure fixation of the implant and/or tissue.

Figure 20D:
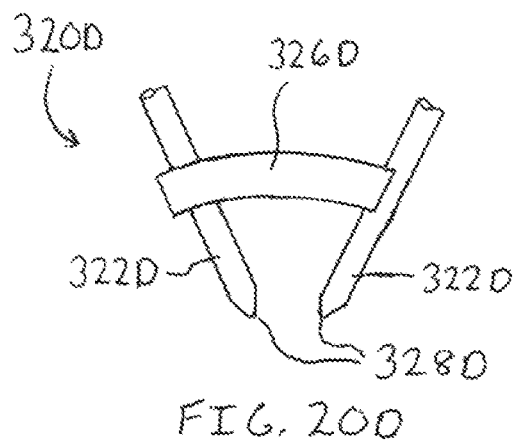
Figure 20E:
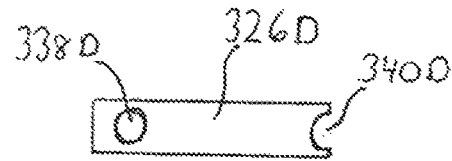

In FIGS. 20D and 20E the staple 320D includes a cross member 326D which has channels for allowing the nails 322D to slide therein. The channels have a central axis which intersect below the cross member 326D such that when the nails 322D are moved distally through the channels, the distal tips 328D of the nails connect each other, similar to the previously described embodiments. As seen in FIG. 21E, the cross member 326D includes one thru-channel 338D and one edge-channel 340D. This configuration allows the nails 322D to be inserted sequentially (not at the same time, if desired). In an exemplary method of use, the first nail 322D is partially positioned in the implant (or tissue) to be fastened. The first nail 322D is angled relative to vertical at an angle generally equal to angles of the channels of the cross member 326D. Then, the edge-hole 340D of the cross member 326D is positioned around the first nail 322D. The second nail 322D is inserted into the thru-hole 338D of the cross member 326D, and both nails 322D are fully inserted into the implant/tissue. The distal tips 328D of the nails 322D may be ultrasonically welded together, and the nails 322D may be ultrasonically welded to the cross member 326D.

Figure 21:
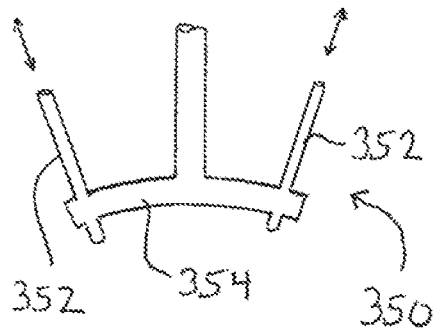
FIG. 21 is a welding horn for a triangulation fastener.

An exemplary staple welding horn 350 is shown in FIG. 21. The horn 350 includes two elongate horn shafts 352 disposed in channels in a horn base 354. The horn shafts 352 may be slideable within the channels. Both the horn shafts 352 and the horn base 354 may emit ultrasonic energy for welding the thermoplastic material, such as PEEK, of the above described staples. In use, the horn shafts 352 are retracted proximally. The horn 350 is placed over the staple such that the horn shafts 352 align with the central bore in the nails. It should be noted that the nails of the staples previously described may include longitudinally extending bores not only to receive the ultrasonic horn but also to receive an instrument for positioned the nails in implant and/or tissue. With the horn 350 properly aligned, the horn shafts 352 may be distally extended into the channels of the nails. Ultrasonic energy and a desired weld profile may be used to thermally bond the staple.

Figure 22A:
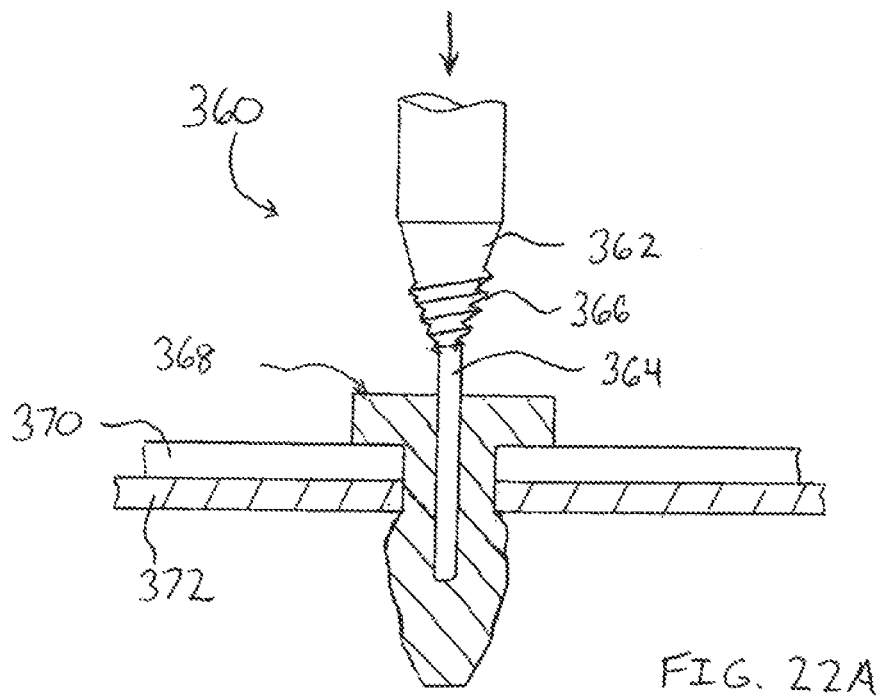
FIGS. 22A and 22B illustrate a thermoplastic implant removal device.
Figure 22B:
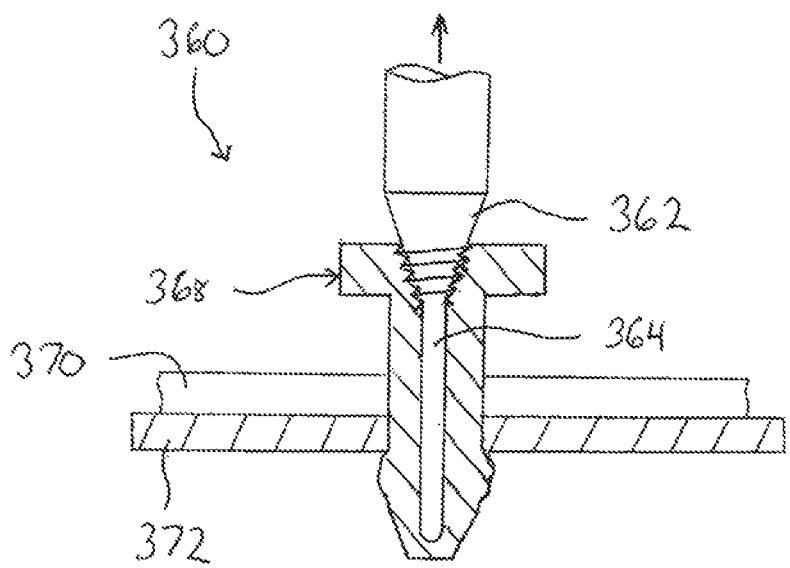

Referring now to FIGS. 22A and 22B, a thermoplastic removal instrument 360 is shown. The instrument 360 includes an ultrasonic welding horn shaft 362. The distal portion of the shaft 362 is generally conical and tapers inward toward the distal tip. An elongate pin 364 extends from the distal tip. The distal portion of the shaft 362 includes helical threads 366 disposed on the outer surface thereof. It is contemplated that besides having helical threads, the distal portion of the shaft may include any engagement means such as barbs, prongs, or other similar configurations. To remove a thermoplastic component, the elongate pin 364 of the instrument 360 is inserted into a channel of the component. The channel may already exist in the component or may need to be created with a drill and bit. With the pin 364 in the channel, the instrument 360 is moved further distally until the distal portion of the shaft 362 contacts the component. The distal portion is then threaded into the component with the helical threads 366. Ultrasonic energy is emitted from the pin 364 to soften the thermoplastic material of the component. As the material is softened, the instrument 360 is pulled proximally, and the distal portion of the shaft 362 begins to pull the component out. The softened thermoplastic material adjacent the pin 364 is inherently reshaped as the component is pulled from the implant/tissue.

In FIGS. 22A and 22B, a PEEK fastener 368 is holding a bone plate 370 to bone 372. The fastener 368 may be removed from the bone 372 with the method just described. In FIG. 22A, with the fastener 368 in place, the distal portion of the fastener 368 is thick thereby locking the fastener 368 in the bone 372. In FIG. 22B, as the fastener 368 is pulled proximally, the distal portion thins or narrows as it is pulled from the bone 372 and plate 370. Because the fastener 368 is only softened and not liquefied, the removal instrument 360 is able to remove substantially all, if not entirely all, of the thermoplastic material from the bone 372.

FIGS. 23A-23D illustrate a method of stabilizing a fracture bone with the devices of the present invention. In FIG. 23A a femur 380 is shown with a fracture 382. An intramedullary rod 384 may be placed within the medullary canal of the femur 380, as seen in FIG. 23B. The rod 384 may be made of thermoplastic material, such as PEEK. The rod 384 is positioned in the bone such that it spans the fracture on each side. In FIG. 23C, a plurality of channels are created in the femur 380. The channels are dimensioned to receive a fastener of the present invention. A first channel 386 is created in cortical bone of the femur 380. The first channel 386 creates a passage from the exterior of the femur to the IM rod 384. A second channel 388 is created in the cortical bone and slightly into the IM rod 384. The second channel 388 forms an indentation or nest in the rod 384. A third channel 390 is formed entirely through the femur 380 and IM rod 384. The third channel 390 is a thru-hole which extends through the cortex (both cortical sides) of the femur 380. A fourth channel 392 is created in cortical bone and partially into the IM rod 384. The fourth channel 392 forms a blind-hole in the rod 384. The channels may be formed by any means known to surgeons, such as by a drill and bit, a guidewire, a reamer, or other similar instrument. It is contemplated that any number of channels and any combination of channel types may be created in the bone and IM rod.

In FIG. 23D fasteners are positioned in the channels and ultrasonically welded in place. Before a first fastener 394 is placed in the first channel 386, the surface of the IM rod 384 exposed by the channel requires preparation for bonding. The surface may be roughened in situ using any suitable instrument. Alternatively, the surface may be roughened by the manufacture or the surgeon before implantation in the bone. With the bonding surface prepared, the first fastener 394 in placed in the first channel 386 such that the distal end of the fastener 394 contacts the bonding surface of the rod 384. Ultrasonic energy is applied to the fastener to thermally bond the first fastener 394 with the IM rod and femur. A second fastener 396 is placed in the second channel 388 with the distal end of the second fastener 396 positioned in the indentation in the rod 384. The second fastener 396 may then be ultrasonically welded to the rod and femur. A third fastener 398 is placed in the thru-hole of the third channel 390. The leading end of the third fastener 398 is configured for insertion through the channel, while the trailing end of the fastener may include a cap or head. The third fastener 398 is ultrasonically welded to the IM rod and femur. The leading end of the third fastener 398 may be contoured or flattened to form a leading end head. A fourth fastener 400 is placed in the fourth channel 392 and within the blind hole in the rod. The fourth fastener 400 is thermally welded, and the cap or head is contoured to conform to the outer surface of the femur. It is contemplated that the three-horn instrument of FIGS. 4A-4C may be used to create the bonding regions, to weld the fasteners, and to contour the thermoplastic implants.

Figure 24A:
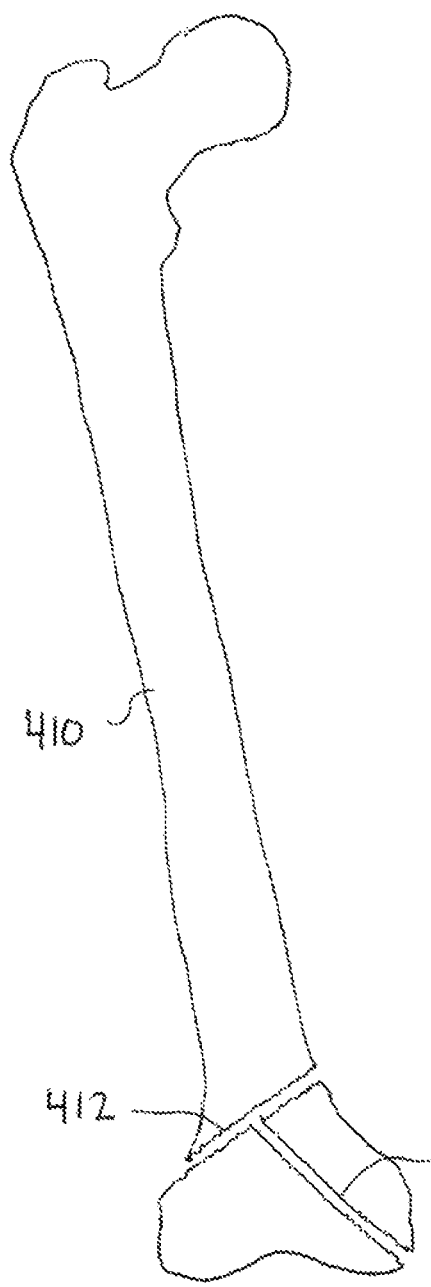
FIGS. 24A and 24B illustrate the repair of a fractured head of a bone.
Figure 24B:
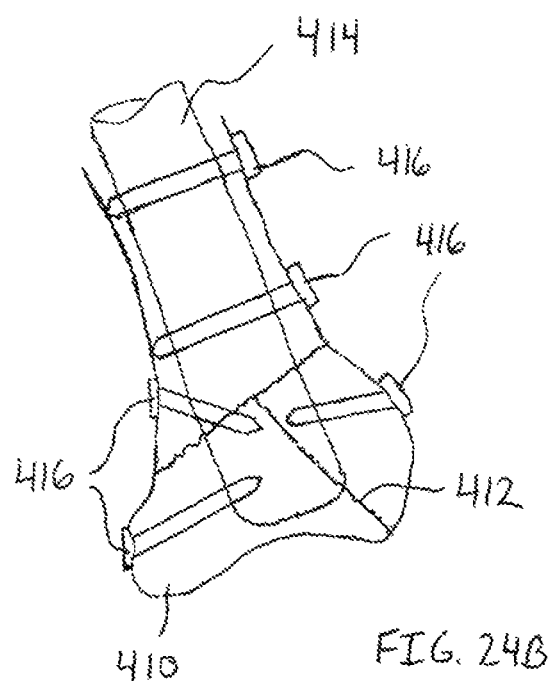

Referring now to FIGS. 24A and 24B, the devices and methods of the present invention are used to repair an end portion of a bone 410 having a plurality of fractures 412. Like the repair of the fractured femur of FIGS. 23A-23D, a PEEK intramedullary rod 414 is placed in the medullary canal of the bone 410. A plurality of channels is created through the end portion of the bone 410 and into the IM rod 414. Any channel type previously described may be used in this method. A plurality of thermoplastic fasteners 416 are placed in the channels and are ultrasonically welded to the rod 414. Multiple (three or more) fasteners 416 may be welded to the end portion of the IM rod 414 without reducing the strength of the rod. Since the fasteners and rod are made of PEEK, the thermally bonded fasteners within the rod enhance the strength of the rod. Therefore, many fasteners may be bonded with the rod without losing structural support from the channels created in the rod.

Another method and apparatus for repairing a fractured bone is illustrated in FIGS. 25A and 25B. Instead of an intramedullary rod being placed in the bone canal, a bone plate 420 is positioned against the fractured femur 422 on the exterior side of the bone. The bone plate 420 is made of thermoplastic material such as PEEK. A first channel 424 is created through the plate 420 and through the bone 422 to form a thru-hole. A second channel 426 is drilled through the bone plate 420, across the fracture 428, and through the bone 422. A third channel 430 is formed through the plate 420 and partially into the femur 422. Additional channels may be created as desired. In FIG. 25B, PEEK fasteners 432 are placed in the channels and ultrasonically welded to the femur 422 and bone plate 420. The fastener type and method of welding each fastener may be similar to previously described embodiments.

Figure 26A:
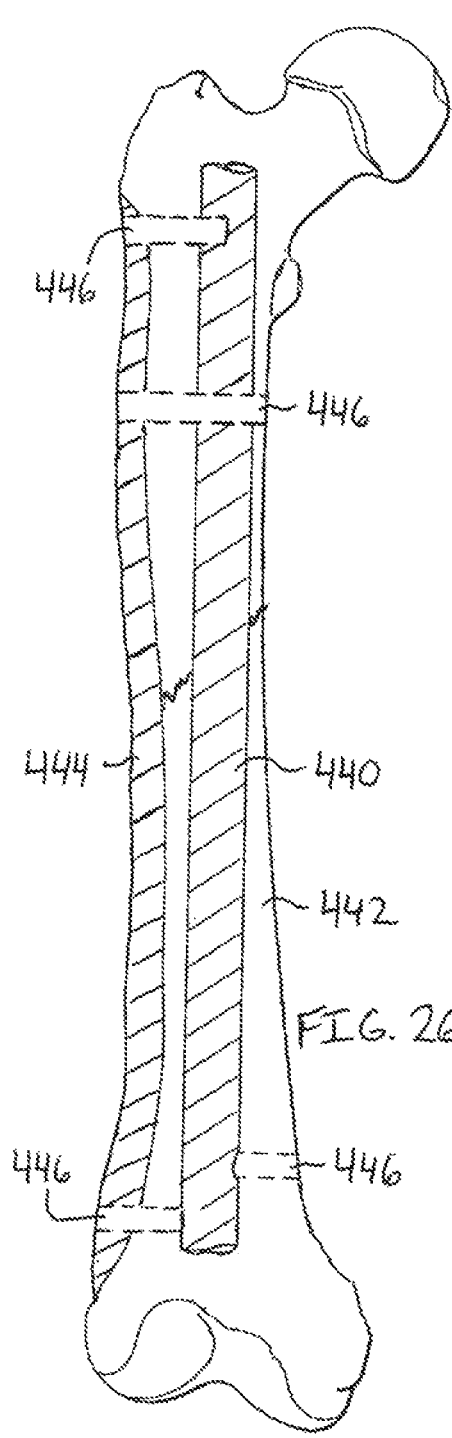
FIGS. 26A and 26B illustrate the repair of a fractured bone with a combination of a thermoplastic rod and plate.
Figure 26B:
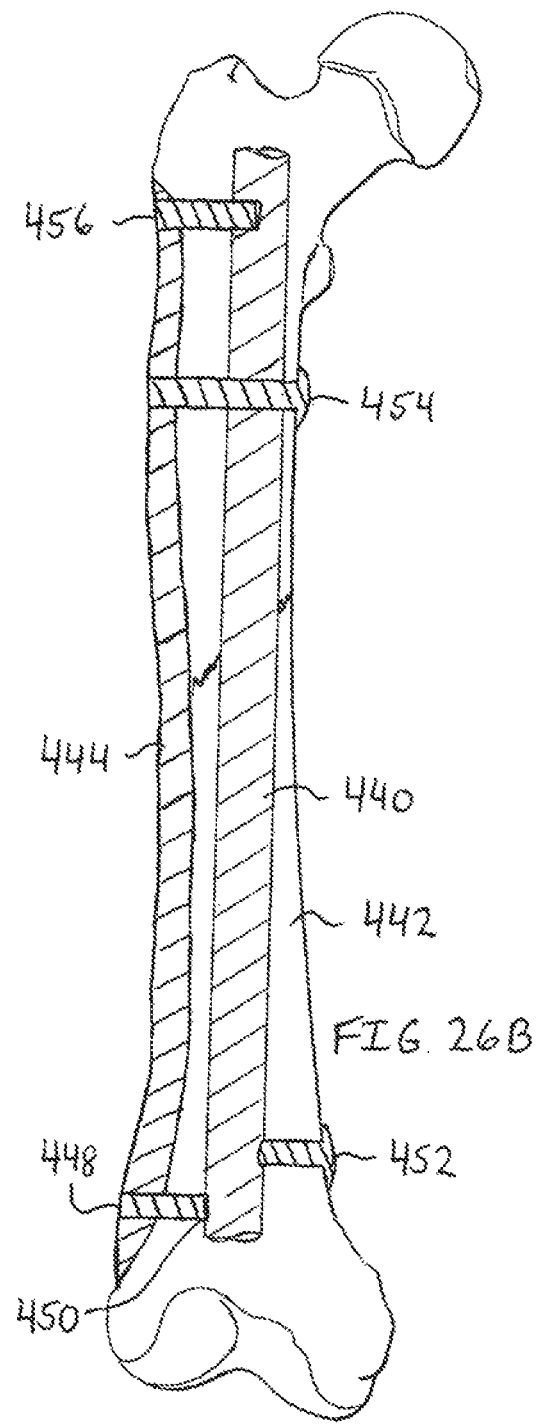

FIGS. 26A and 26B show a combination configuration for repairing a fractured bone. The combination includes an IM rod 440 positioned in the medullary canal of the bone 442 and a bone plate 444 positioned against the exterior surface of the bone 442. The rod and plate may be made of PEEK. In FIG. 26A, a plurality of channels 446 are created through the plate, bone, and/or rod. PEEK fasteners, shown in FIG. 26B, are positioned in the channels 446 and ultrasonically welded to the plate, bone, and rod. A first fastener 448 is welded to a bonding region 450 on the surface of the rod 440. A second fastener 452 is welded in an indentation in the rod 440. A third fastener 454 extends through the plate, bone, and rod. The third fastener 454 includes a mushroomed or contoured head on its distal end, and on the proximal end, no head is needed since the fastener bonds directly to the bone plate 444. A fourth fastener 456 is positioned in a blind hole in the rod 440. The fourth fastener 456 is also free of a proximal head or cap. As seen in FIG. 26B, the bone plate 444 is contoured to conform to the exterior surface of the femur 442. This may be performed with ultrasonic energy, resistive heating, or other suitable energy source.

Figure 27A:
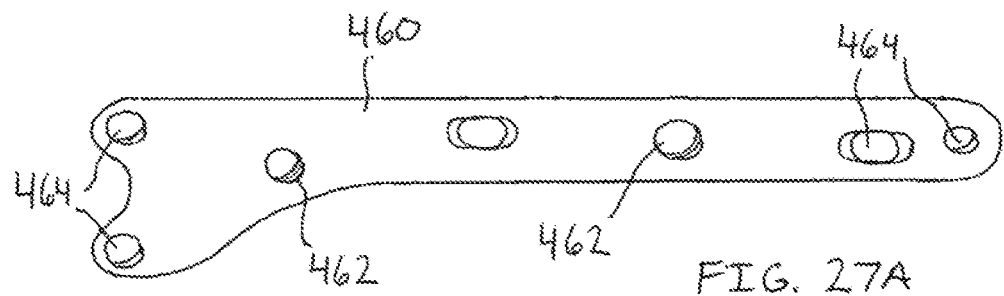
FIGS. 27A-27C show a bone plate of the present invention.
Figure 27B:
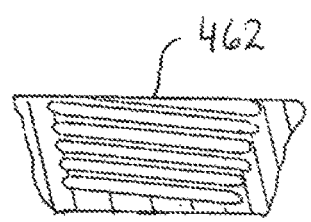
Figure 27C:
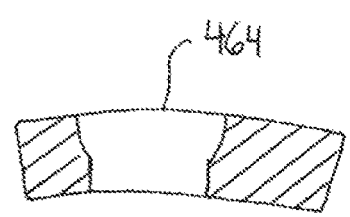

An exemplary bone plate 460 of the present invention is shown in FIGS. 27A-27C. Some previously described bone plates and IM rods included no pre-fabricated holes. Instead, the surgeon formed channels in the plates and rods to insert fasteners. In the embodiment of FIG. 27A, the bone plate 460 includes a plurality of openings. Some openings are threaded while others are free of treads. FIG. 27B is a cross sectional view of a threaded opening 462 of the plate 460. FIG. 27C is a cross sectional view of an unthreaded opening 464. The plate 460 is made of thermoplastic material such as PEEK.

Figures 28A, 28B, 28C, 28D:
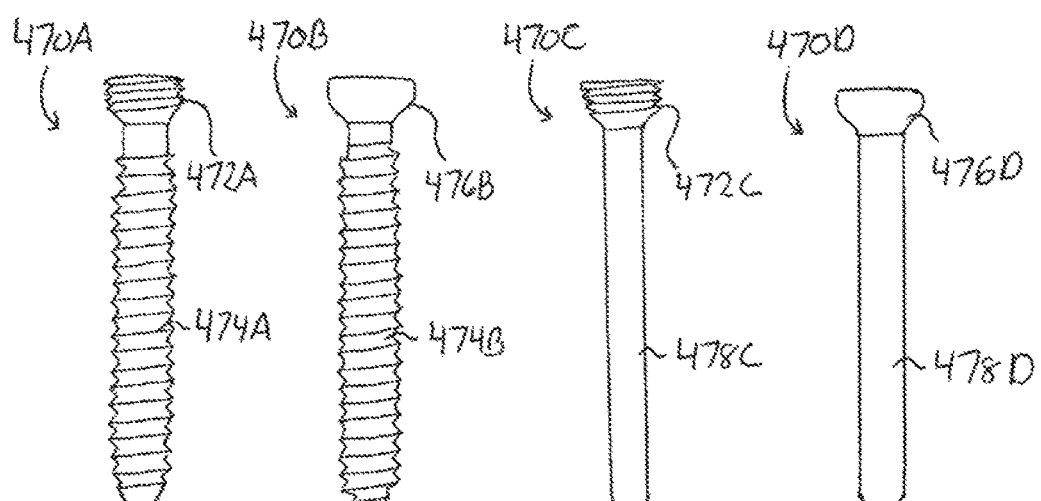
FIGS. 28A-28D illustrate exemplary fasteners for use with a bone plate or other implant.

Shown in FIGS. 28A-28D are exemplary fasteners for affixing the bone plate to a bone. The fasteners are made of PEEK and may include a central channel configured for receiving a welding horn. FIG. 28A shows a PEEK fastener 470A having a threaded head 472A and a threaded shaft 474A. The threaded head 472A is dimensioned to be threaded into one of the threaded openings 462 of the bone plate 460. The thread shaft 474A is configured for insertion in tissue. FIG. 28B shows a fastener 470B with a smooth, unthreaded head 476B and a threaded shaft 474B. The unthreaded head 476B is configured for insertion in one of the unthreaded openings 464 of the bone plate 460. FIG. 28C shows a fastener 470C having a threaded head 472C and smooth shaft 478C. FIG. 28D shows a fastener 470D with a smooth head 476D and smooth shaft 478D. In use, the bone plate is positioned on a fractured bone. Fasteners of FIGS. 28A-28D are positioned through the openings in the plate and into the bone. The fasteners are ultrasonically welded to the plate and bone. The smooth head or smooth shaft of a fastener is thermally bonded to the plate or tissue, while the threaded head or threaded shaft is mechanically secured and thermally bonded to the plate and/or tissue.

Figures 29, 30:
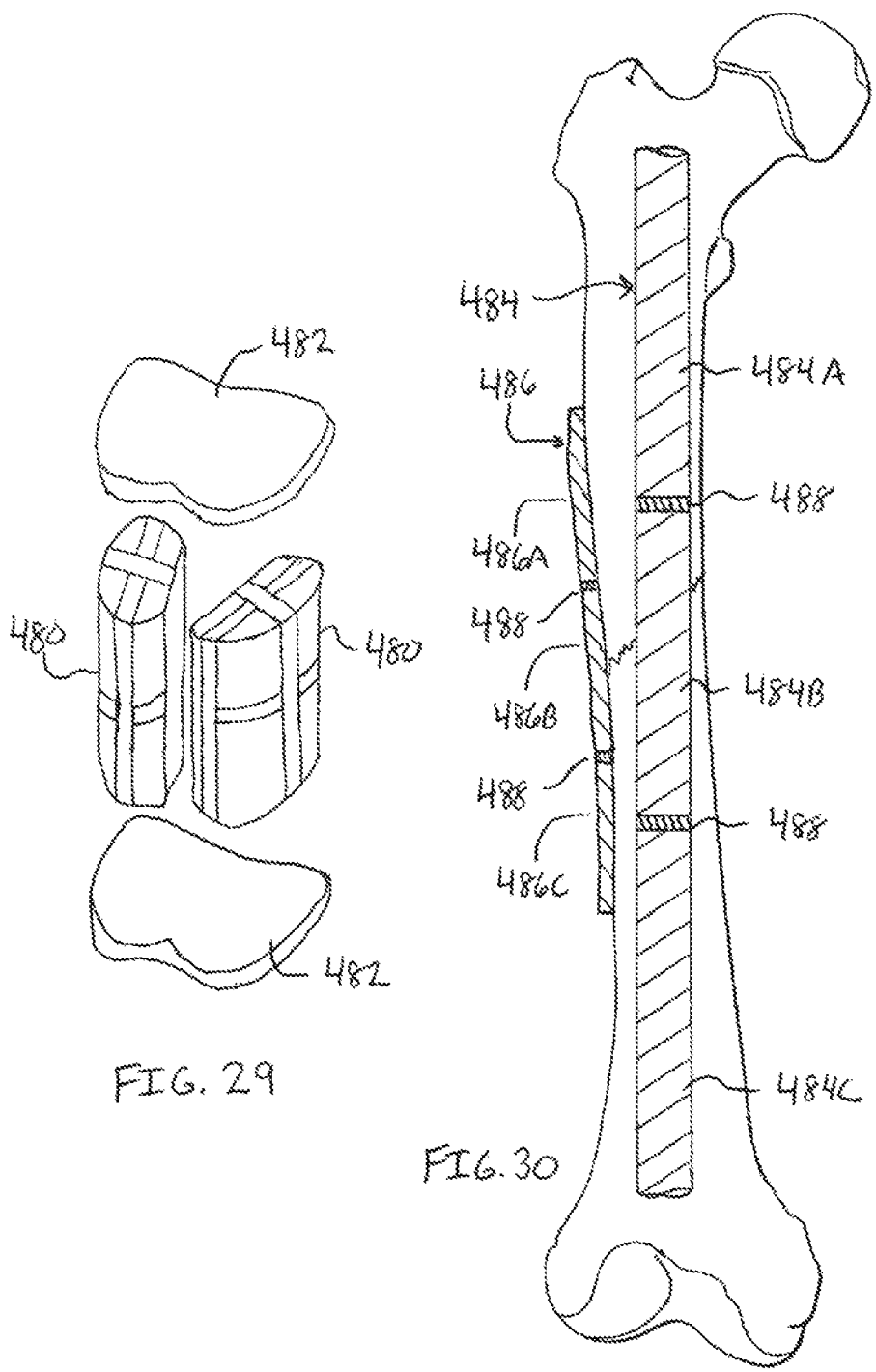
FIG. 29 shows modular assembly of a spinal implant.
FIG. 30 illustrates sequential welding of an intramedullary rod.

The trauma welding system also provides for the modular assembly of implants intracorporeally. In FIG. 29, spinal cages 480 include thermoplastic material which may be welded to vertebral body replacement components 482. The use of ultrasonic energy to weld the assembly together in the body prevents damage to surrounding tissue since the vibration energy creates just enough heat to soften and make tacky the thermoplastic material. FIG. 30 illustrates a modular IM rod 484 and a modular bone plate 486. The IM rod 484 includes a first portion 484A welded to a second portion 484B at a bonding region 488. The second portion 484B is welded to a third portion 484C at another bonding region 488. In this embodiment, the smaller portions of the rod may be implanted using minimally invasive techniques. Each portion may be welded to an adjacent portion intracorporeally. The bone plate 486, likewise, includes a plurality of modular portions 486A, 486B, 486C which may be thermally bonded together in the body. It is also contemplated that the small portions of the rod, plate, or other implant may be assembled by the surgeon in the operating room prior to implantation. This way, the implant manufacture can produce small portions of an implant allowing the surgeon to select the size and number of portions to assembly to create a custom tailored implant. It is contemplated that intracorporeally sequential welding applies to other types of implants as well, such as modular stents, modular acetabular component, modular spacers, and modular wedges.

Figure 31A:
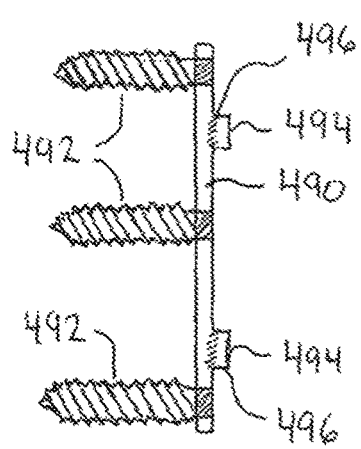
FIGS. 31A and 31B show the stabilization of the spine using thermoplastic implants.
Figure 31B:
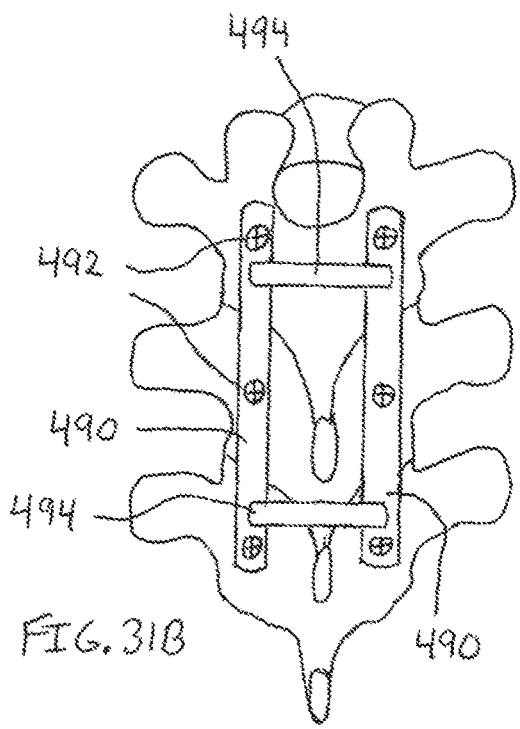

In a further embodiment of the present invention shown in FIGS. 31A and 31B, the trauma welding system may be used to stabilize joints of the spine such as intervertebral joints and facet joints. Stabilization of the spine is achieved by attaching rigid rods, plates, spacers, or wedges 490 between two or more vertebrae. Fasteners 492, such as pedicle screws, are inserted into the vertebrae, and plates/rods 490 are connected to the screws 492. The spinal rods, plates, fasteners, etc. may include thermoplastic material, such as PEEK. The implants may be biodegradable or biostable. In FIG. 31B, PEEK pedicle screws 492 are inserted into vertebral bodies using the methods described herein. PEEK stabilizing plates 490 span the pedicle screws 492 and are ultrasonically bonded with the screws. Stabilizing cross bars 494 are thermally welded to the stabilizing plates at bonding regions 496. It is contemplated that any combination of fasteners, rods, plates, and wedges may be ultrasonically welded to stabilize joints of the spine.

Figure 32:
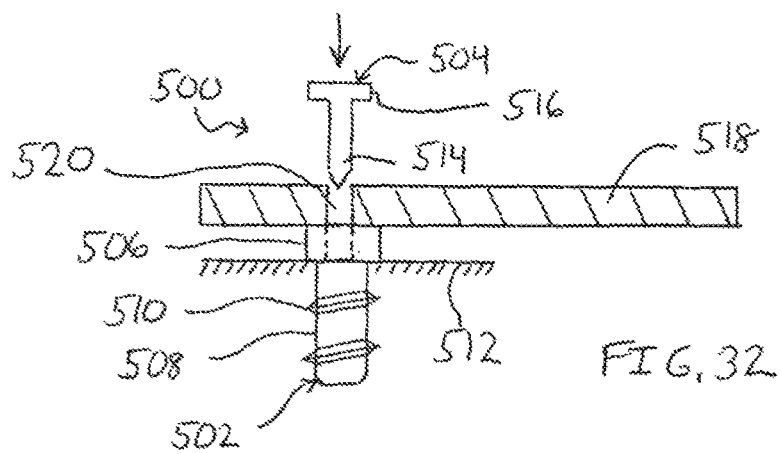
FIG. 32 illustrates an exemplary embodiment of a pedicle implant.

In FIG. 32, a spacing fastener 500 is shown. The fastener 500 includes an anchor 502 and a cap 504. The anchor 502 is generally a cylindrical shaft with a head 506 disposed on the proximal end of the shaft 508. The shaft 508 may include helical threads 510 for mechanical locking into tissue 512. The anchor 502 includes a bore extending along the central axis of the anchor. The fastener 500 further includes a cap 504 having a post 514 and a lid 516 attached to the proximal end of the post. The post 514 is dimensioned and configured for insertion into the bore of the anchor 502. Both the cap and anchor may be made of thermoplastic material such as PEEK. In an exemplary method of use, the anchor 502 is implanted in tissue 512 as shown in FIG. 32. The anchor 502 may be mechanically and/or thermally bonded in the tissue. A bone plate or rod 518 is placed over the head 506 of the anchor 502. A pre-drilled passageway 520 formed in the plate by the manufacturer is aligned with the bore of the anchor. Alternatively, a passageway 520 may be formed by the surgeon and aligned with the bore. The cap 504 is inserted through the passageway 520 of the plate 518 and into the bore of the anchor 502. The cap, plate, and anchor may be thermally bonded together with ultrasonic energy. In the implanted configuration, the head 506 of the anchor 502 acts as a spacer between the tissue 512 and plate 518. The spacing fastener 500 of FIG. 32 may be used as a pedicle screw separating a stabilizing plate from vertebral bodies.

In a further embodiment, the trauma welding system may be utilized to provide flexible stabilization of the spine, or any other joint or bone of the body. The soft tissue around and near a joint may become weakened over time, and the range of motion of the joint usually increases thereby allowing excessive tissue laxity. Also, instability of a joint may be caused by structural changes within the joint as a result of trauma, degeneration, aging, disease, or surgery. An unstable spinal joint may be rigidly stabilized as previously explained or may be dynamically stabilized to allow some range of motion of the spinal joints. Fasteners, screws, plates, rods, etc. made of PEEK may be implanted between two or more vertebrae. The plates and rods are configured and dimensioned to permit some flexing and/or bending. The amount of flexibility of these PEEK implants may be adjusted by the surgeon in the operating room using energy, such as ultrasound, resistive heating, etc. and by varying the weld parameters.

Figure 33:
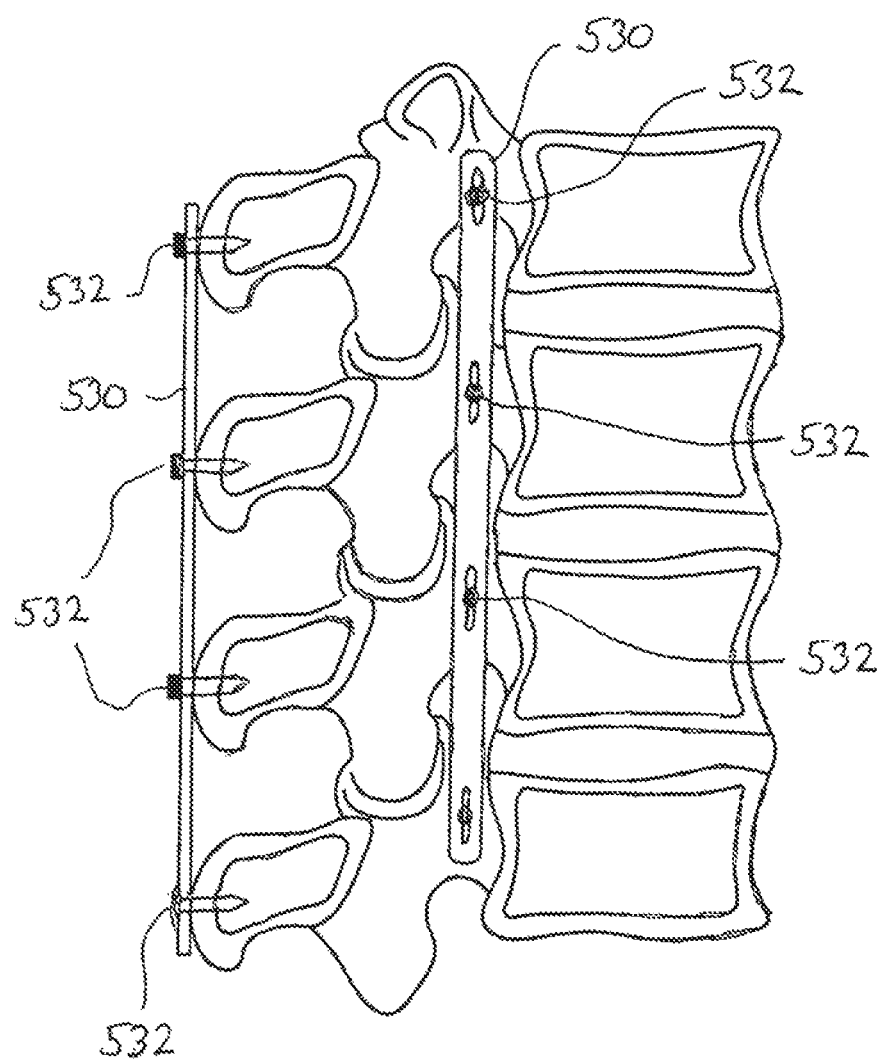
FIG. 33 shows stabilization of the spinal column with thermoplastic implants.

As seen in FIG. 33, a plate or rod 530 may be configured to lock with a fastener 532 in one direction, but would allow movement in another direction. For example, the plate 530 and fastener 532 permits superior and inferior motion of the spine but would prevent lateral motion. Also, the plate 530 and fastener 532 may permit motion in one plane and restrict motion in a different plane. The fasteners and plates of FIG. 33 may be made of PEEK and may be ultrasonically bonded to stabilize the spine.

Figure 34A:
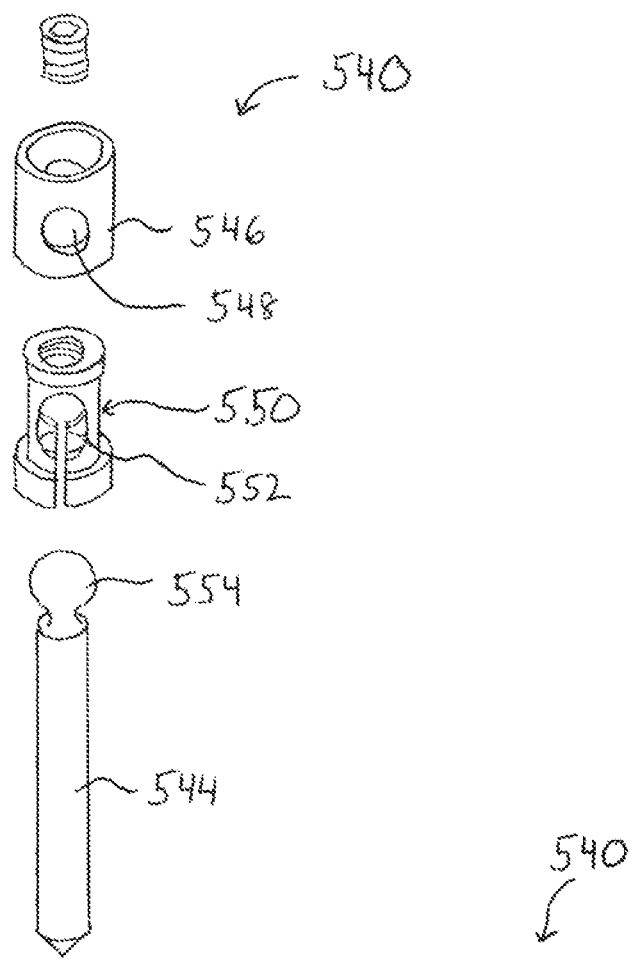
FIGS. 34A and 34B illustrate a pedicle fastener apparatus.
Figure 34B:
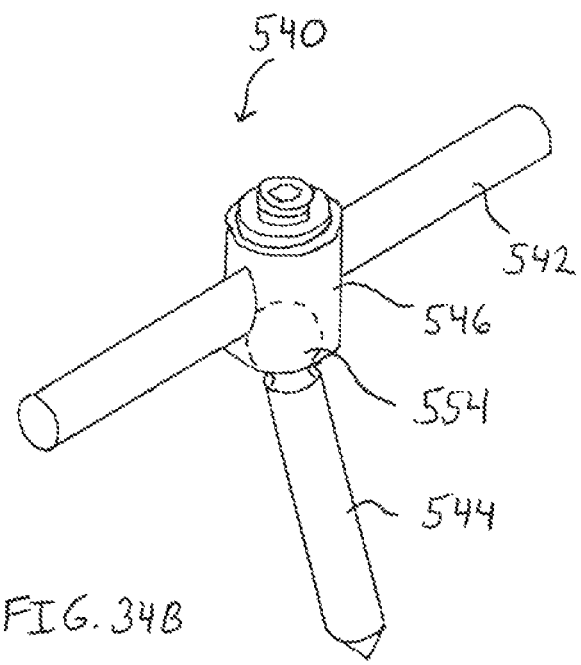

FIGS. 34A and 34B illustrate another embodiment to stabilize a joint such as a joint of the spine. The swivellable pedicle screw assembly 540 may be used to connect a longitudinal bar 542 to a pedicle screw 544 thereby forming a spine stabilization device. The assembly 540 includes a body 546 having an upper end, a lower end, a hole 548 which is open at least towards the bottom and has an axis, and a through hole positioned perpendicular to the axis. The assembly 540 also has a collet chuck 550 mounted coaxially on the inside of the body 546 in such a way that it can slide along the axis. The collet chuck 550 has a through hole 552 which is flush with the through hole of the body 546, and a chamber which faces at least downwards and is defined by tongues spring-mounted against the cylinder axis. When the collect chuck 550 is inserted in the body, the through holes 552 align to allow insertion of the longitudinal bar 542. The head 554 of a pedicle screw 544 can be clicked into the chamber from below by spring-action. The assembly 540 allows for the pedicle screw 544 to be inclined within a certain range. The assembly may be made of thermoplastic material such as PEEK. Ultrasonic energy may be used to thermally bond the head 554 of the pedicle screw 544 within the chamber of the collet chuck 550 and to bond the longitudinal bar 542 with the pedicle screw 544.

It is contemplated that a simple ball and socket assembly may be used to stabilize the spine as well. The ball is the head of the pedicle screw as described above. The socket includes a chamber for receiving the ball. The socket may include an attachment means, such as a thru-hole or a thermal bonding region, for receiving and affixing a plate or rod. The ball, socket and plate/rod may be ultrasonically welded together to form a spin stabilizing configuration.

Figure 35A:
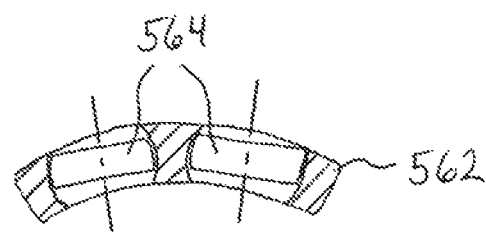
FIGS. 35A and 35B show a thermoplastic bone fixation assembly.
Figure 35B:
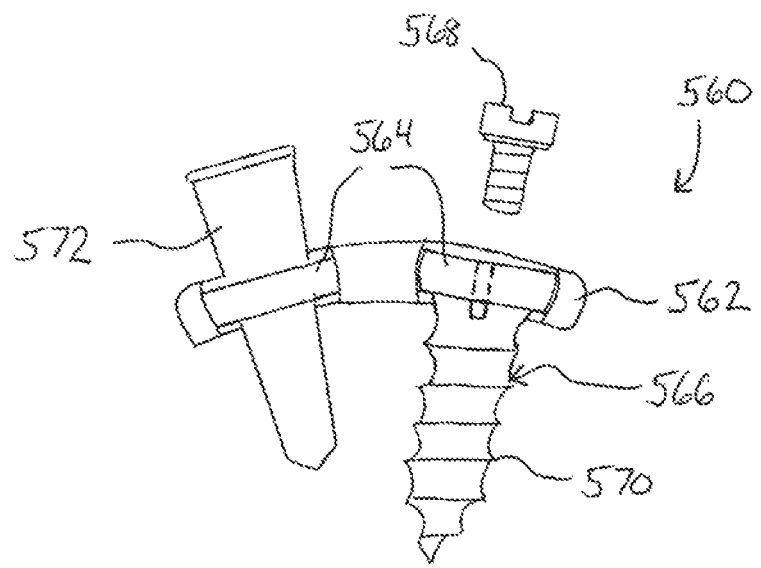

FIGS. 35A and 35B illustrate a bone fixation assembly 560 for securing a bone plate to bone. The assembly 560 includes the fixation device 562, a bushing 564, a fastening screw 566, and a locking screw 568. The bushing 564 is seated within a through hole in the fixation device 562 and can rotate within the through hole and has a sidewall with a bore. The sidewall has at least one slot for allowing outward expansion of the sidewall against the through hole to thereby lock the bushing 564 at a selected angle relative to the axis of the through hole. The fastening screw 566 has a threaded shaft 570 for insertion through the bore of the bushing 564 and threads into bone to secure the bushing 564 and fixation device 562 to bone. The head of the fastening screw 566 fits in the bushing and includes a radial wall and open end defining a recess. The radial side wall has at least one slit for allowing outward expansion of the radial wall thereby outwardly expanding the sidewall of the bushing 564. The locking screw 568 has a body that threads in the head of the fastening screw 566 to thereby outwardly expand the radial wall of the fastening screw 566. The assembly components may be made of PEEK. In an alternative embodiment, a fastening member 572, made of PEEK, replaces the fastening screw 566 and locking screw 568. In this embodiment, the fastening member 572 is inserted through the bore of the bushing 564 and into the bone. The fastening member 572 may be ultrasonically welded to the bushing 564 and the bushing 564 may be thermally bonded to the fixation device 562. The fastening member 572 is ultrasonically bonded to the bone using the welding methods described herein.

Figure 36A:
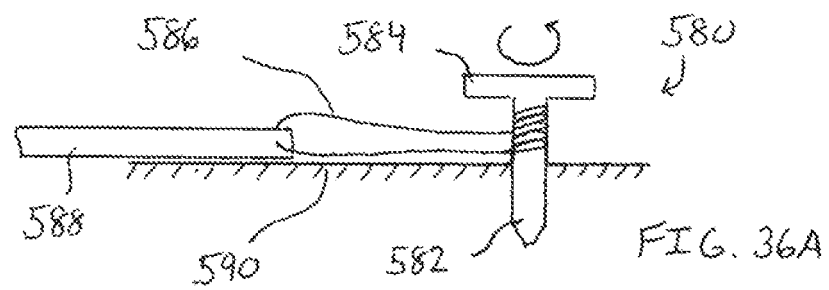
FIGS. 36A and 36B illustrate a thermoplastic suture tensioning device.
Figure 36B:
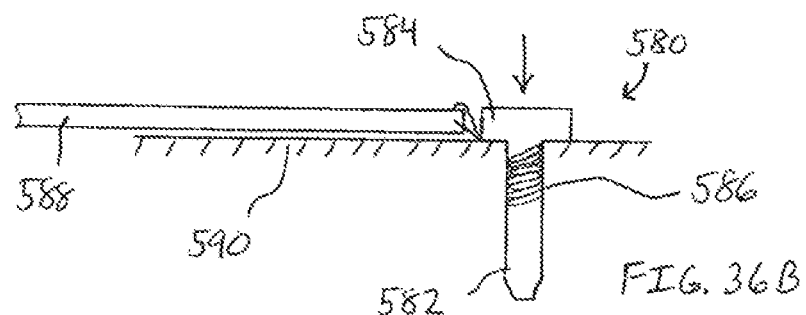

Referring now to FIGS. 36A and 36B, a cable tensioning fastener 580 is illustrated. The fastener 580 includes a post 582 and a cap 584 disposed on the proximal end of the post. The post 582 is configured for winding a suture or cable 586 thereon. The suture 586 may be attached to the post 582 by applying heat to PEEK material of the post, setting the suture into the softened PEEK, and allowing the PEEK to harden. Alternatively, a small channel may extend radially through the post. The suture 586 may be threaded through the channel. In a simple configuration, the suture 586 may be wrapped over itself on the post 582, like a spool of string. In an exemplary method of use as shown in FIGS. 36A and 36B, the suture or cable 586 is placed through or around tissue 588 such as a rotator cuff. The suture 586 is attached to the post 582 of the fastener 580 as previously described. The fastener 580 is then rotated to coil up the suture 586 on the post 582 and draw the rotator cuff 588 in close to the fastener 580. To secure the assembly, the fastener 580 is inserted into tissue such as bone 590. Ultrasonic energy is applied to the fastener 580 to bond the fastener to the tissue 590 and bond the suture 586 to the post 582 of the fastener 580. In this position, the rotator cuff is securely fastened to the bone.

Figure 37:
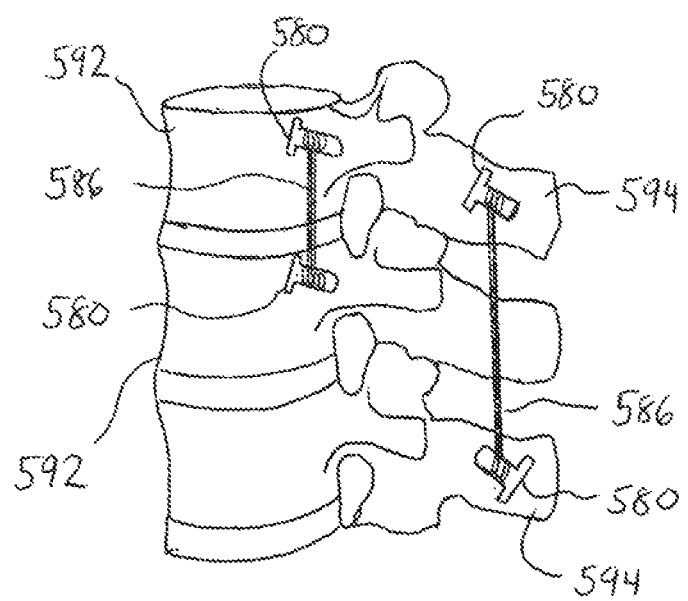
FIG. 37 shows the tensioning device of FIGS. 36A and 36B in use to stabilize the spine.

FIG. 37 illustrates another exemplary use of the cable tensioning fastener 580 of FIGS. 36A and 36B. A first tensioning fastener 580 is positioned in a vertebral body 592. A second fastener 580 is positioned in an adjacent vertebral body 592. A cable 586 spans between the posts of the first and second fasteners. One or both fasteners are rotated to tension the cable, and the fasteners are implanted in the vertebrae and ultrasonically welded in place. Third and fourth fasteners are implanted in spinous processes 594. A tensioned cable 586 is connected with the fasteners 580. The embodiment of FIG. 37 provides controlled stabilization of the spine by affixing flexible or non-flexible cables between vertebrae. Flexible cables provide dynamic stabilization, while non-flexible cables provide rigid stabilization.

The present invention also provides a glenoid replacement component 600A, shown in FIG. 38A. The inner side is configured for placement on the scapula 602, and the outer side is configured for articulation of the head 604 of the humerus 606. Thermoplastic fasteners 608 secure the component 600 to bone. In FIG. 38B, a glenoid replacement component 600B is shown having prongs 610 extending from the inner side. The prongs 610 may be inserted into pre-drilled holes in the scapula and ultrasonically welded therein. FIG. 38C illustrates another embodiment of a glenoid replacement component 600C. The component 600C includes two thru-holes 612 extending from the outer to the inner side of the component. PEEK fasteners may be used to secure the replacement component to bone. The caps or heads of the fasteners may be contoured and flattened so as to not interfere with the head of the humerus.

Figure 39:
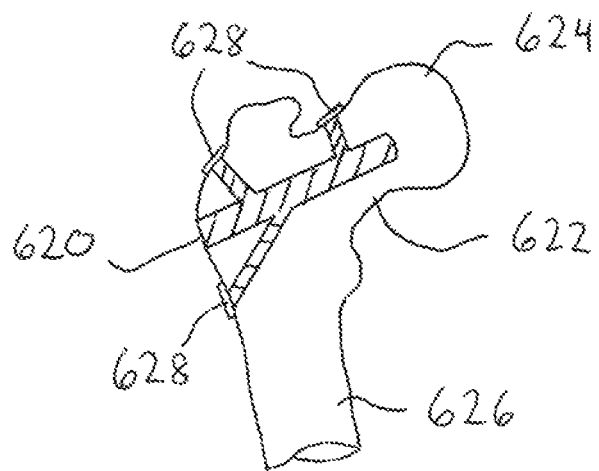
FIG. 39 shows a thermoplastic cross pin.
Figure 40:
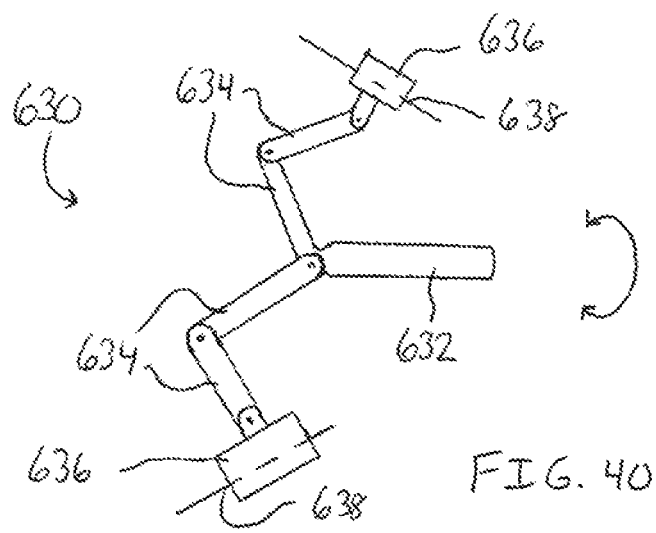
FIG. 40 illustrates a jig device for use with the cross pin of FIG. 39.

Referring now to FIG. 39, a thermoplastic cross pin 620 is illustrated. The pin 620 may be made of PEEK. The cross pin 620 is used to stabilize and strengthen the neck 622 and head 624 of the femur 626. To implant the pin, the pin 620 is positioned in a channel extending into the neck 622 and head 624. The pin 620 may be mechanically locked within the channel and/or may be thermally bonded within the channel. Thermoplastic fasteners 628 are placed through the cortical bone of the femur 626 and into contact with a bonding region on the pin 620. As previously described, the bonding region may be a roughened surface, an indentation, a blind-hole, or a thru-hole. The fasteners 628 are then ultrasonically welded to the pin 620 and bone to secure the pin 620 within the femur 626. FIG. 40 illustrates a cross pin jig 630 to be used during implantation of the pin 620. The jig 630 includes a shaft 632 and a series of pivoting arms 634 connected with the shaft 632. At the end of the pivoting arms 634 is an insertion guide 636. The guide 636 has a passageway 638 configured for guiding a fastener. The arms 634 pivot in one plane with respect to the shaft 632 such that the passageway 638 of the insertion guide 636 is always aligned with the shaft 632. In use, the shaft 632 of the jig 630 is inserted into the drilled channel extending into the neck and head of the femur. The insertion guides 636 are positioned adjacent the surface of the bone. A drill and bit is placed in the guide 636 and a hole is created through the cortical bone terminating in the channel. A plurality of holes may be formed in the bone to receive a plurality of fasteners. Once the holes have been drilled, the jig 630 is removed and the cross pin 620 is inserted into the channel. Fasteners are then placed through the holes and into contact with the cross pin 620. Ultrasonic welding bonds the fasteners, cross pin, and bone together. In an alternative embodiment, the shaft of the jig has a diameter which slides into a central passageway of the cross pin. In this embodiment, the cross pin may be implant in the channel, then the jig may be placed in the cross pin.

Figure 41:
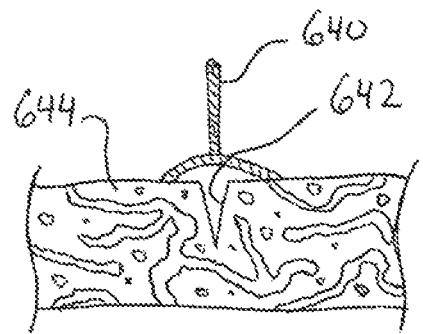
FIG. 41 shows cauterization of tissue using ultrasonic energy.
Figure 42:
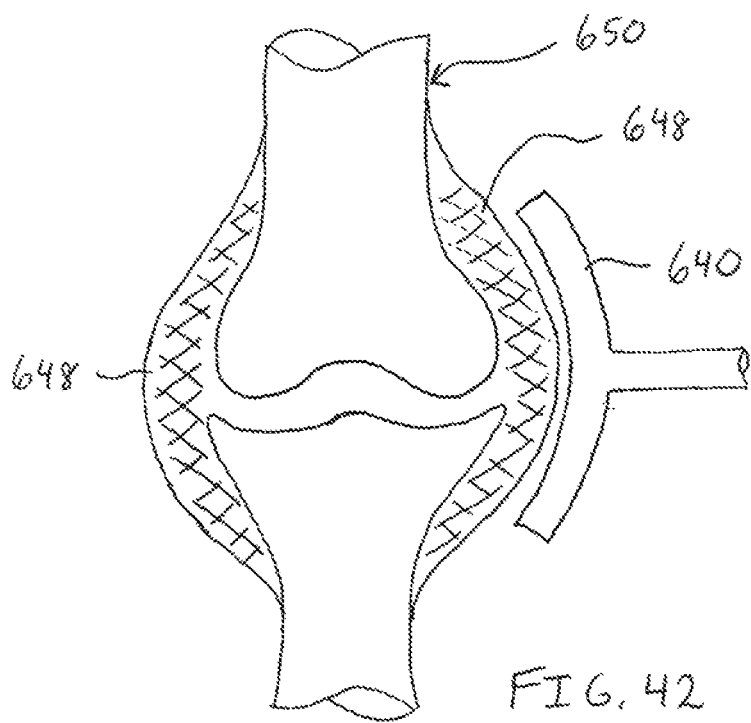
FIG. 42 illustrates cauterization of tissue using energy and gelatin.

In a related invention, FIG. 41 shows a tissue cauterization device 640. A cut or opening 642 is formed in soft tissue such as skin 644. To stop bleeding at the cut, ultrasonic energy may be applied to the tissue. An energy horn 640, similar to those previously described, may be placed in contact with bleeding tissue 644. Ultrasound energy emitted from the horn stops the flow of blood by hemostasis. In FIG. 42, ultrasound from an energy horn 640 is applied to gelatin 648 within a joint 650. The gelatin 648 binds to the tissue and stops bleeding. Gelatin, or other suitable substance, may also be used with the tissue cauterization device of FIG. 41.

Figure 43:
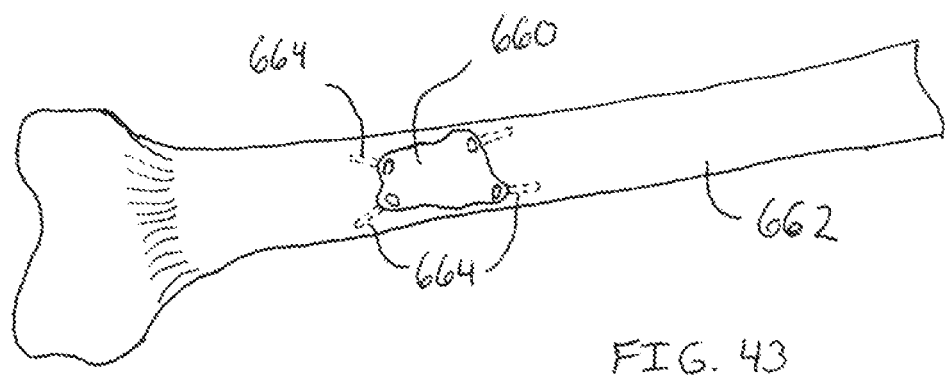
FIG. 43 shows the repair of tissue with a periosteal flap.

FIG. 43 illustrates a periosteal flap 660 used to repair a damaged bone 662. The flap 660 is fastened to the bone 662 using thermoplastic fasteners 664 and methods previously described. Tissue grafts may also secured intracorporeally using PEEK fasteners and ultrasonic energy.

It is also contemplated that metal may be ultrasonically welded to PEEK. For example, a fastener may be made of metal. By placing the metallic fastener on the end effector of the welding instrument, the fastener functions as an extension of the end effector. Therefore, applying pressure from an ultrasound-emitting metallic fastener to a PEEK implant drives the fastener into the implant and thereby secures the fastener to the implant. It is further contemplated that a thermoplastic fastener may be bonded with a metallic implant. Accordingly, the devices and methods described throughout may utilize metallic fasteners bonded to thermoplastic implants and thermoplastic fasteners bonded to metallic implants.

Figure 44A:
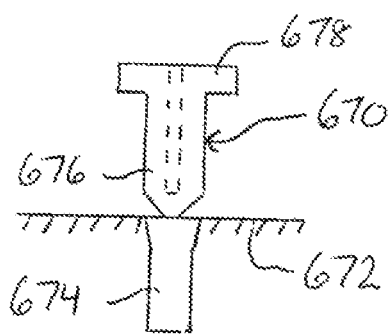
FIGS. 44A and 44B illustrate a method of bonding a thermoplastic fastener in bone.
Figure 44B:
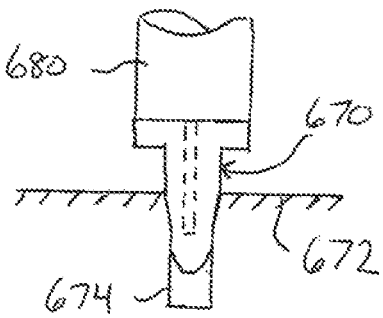

In a further embodiment of the present invention, a method for securing a thermoplastic fastener 670 into tissue 672 is provided. FIGS. 44A and 44B illustrate the method. In FIG. 44A, a channel 674 in drilled in tissue such as bone 672. The fastener 670 includes a post 676 and a lid 678, similar to other fasteners disclosed herein. The diameter of the post 676 is greater than the diameter of the channel 674 in the bone 672 such that the fastener 670 does not freely slide into the channel 674. In FIG. 44B, an end effector 680 is placed in and on the fastener 670. Ultrasonic energy is emitted from the end effector 680 to soften the thermoplastic material of the fastener 670. Simultaneously, downward pressure is applied to the end effector 680 and fastener 670 so that the softened material conforms to the smaller diameter of the channel 674. The fastener 670 is moved distally until it is fully seated in the bone 672. After energy is no longer emitted, the thermoplastic material re-hardens thereby securely bonding the fastener 670 to the bone 672.

In another application of the present invention, thermoplastic fasteners may be used to lock a drug delivery system to an implant or to tissue. For example, a reservoir, balloon, or bladder may be placed within the body and filled with a pharmaceutical substance, gene therapy, or cell therapy. Using PEEK or other thermoplastic, the reservoir may be sealed and stabilized in the body. The contents of the reservoir may leach out or elute out from pores or openings in the reservoir material. Alternatively, the thermoplastic may be biodegradable to allow the contents to escape from the reservoir and into the body. It is contemplated that other drug delivery systems may be used with the present invention. Also, the pharmaceutical agents may include antibiotics, hydroxypatite, anti-inflammatory agents, steroids, antibiotics, analgesic agents, chemotherapeutic agents, bone morphogenetic protein (BMP), demineralized bone matrix, collagen, growth factors, autogenetic bone marrow, progenitor cells, calcium sulfate, immo suppressants, fibrin, osteoinductive materials, apatite compositions, germicides, fetal cells, stem cells, enzymes, proteins, hormones, cell therapy substances, gene therapy substances, bone growth inducing material, osteoinductive materials, apatite compositions with collagen, demineralized bone powder, or any agent previously listed. U.S. Provisional Patent Application No. 60/728,206 entitled "Drug Eluting Implant" discloses means for delivering therapeutic agents. The above-mentioned provisional application is incorporated by reference herein in its entirety.

The welding system of the present invention may further include the process of welding collagen similar to the way PEEK is bonded. Collagen fibers may be infused within a biodegradable polymer or gelatin to enhance welding properties. An energy source, such as ultrasonic energy, may be used to weld the collagen. As previously described the quality of weld depends upon the welding parameters of time, energy time, wattage, frequency, pulsation, pressure, etc. In an exemplary embodiment, collagen is placed in biodegradable polyglycolic acid. Once implanted, the polymer would biodegrade leaving the collagen fibers to heal surrounding tissue. Also, imbedded in the polymer may be cells, antibiotics, keratin, tissue inductive factors, or other pharmaceutical agents disclosed herein.

Alternatively, the collagen fibers may be packed very densely and may be desiccated. The fibers may be welded together or an interfacial material such as talc, glass, graphite, or protein may be added to harden the fibers to a gelatin. In an exemplary embodiment, collagen fibers may be combined with denatured porcine collagen cells. The two substances may be welded together to form a unitary implant. The implant may be fastened within the body for cell therapy, gene therapy, or for the delivery of pharmaceutical agents.

Another welding technique that may be utilized with the present invention is plasma welding. Generally, there are four states of matter in physics: solid, liquid, gas, and plasma. Plasma is a gas in which atoms have been ionized. Therefore, plasma has magnetic and electrical fields that move unpredictably, altering the environment. As the environment changes, so does the plasma. These ionized gases or plasma can be used to fuse, bone or weld material within the body. Plasma welding may be controlled similar to the way thermal welding is controlled as previously described. A plasma stream may be used for polymeric welding, protein welding, or collagen welding. When welding intracorporeally, cold plasma welding may be used to prevent tissue necrosis. Cold plasma can weld tissue, polymers, metals, ceramics, and composites to each other and to one another. Cold plasma may also be used to debride wounds in surgery, to selectively kill bacteria, to roughen the surface of tissue to make it more receptive to pharmaceutical agents, or to prepare a surface of a bone for a joint replacement component. It can also be used to shrink tissue and polymers, ablate tissue, or smooth out wrinkles for plastic surgery either on the surface of the skin or under the skin. Cold plasma welding may be performed through a cannula in a straight line or curved/deflected to reach a target site within the body. The plasma energy may be altered by accelerating electrical charges or electromagnetic fields.

In a related invention, welding of thermoplastics, tissue, implants, etc. described herein may be performed utilizing suction or negative pressure. For example, suction may be applied to a bone to pull a cartilage graft or plate to the surface of the bone. A tube may be placed within the bone to create a negative pressure. This would temporarily hold the implant and contour it to the surface while an energy source is used to weld the graft to the bone with or without traditional or thermoplastic fasteners. Also, suction may be used to stabilize an implant during welding or while an adhesive is curing. Examples of biocompatible adhesives include mollusk adhesive, protein adhesive, fibrin adhesive, cyanoacrylates, or other known adhesives.

It is contemplated the surgical welding system of the present invention may be used with and integrated with the methods and devices disclosed in U.S. Provisional Application No. 60/765,857 entitled "Surgical Fixation Device" filed on Feb. 7, 2006. In the '857 document, various thermoplastic fixation devices are disclosed. The fixation devices may be, but are not limited to, degradable, biodegradable, bioerodible, bioabsorbable, mechanically expandable, hydrophilic, bendable, deformable, malleable, riveting, threaded, toggling, barded, bubbled, laminated, coated, blocking, pneumatic, one-piece, multi-component, solid, hollow, polygon-shaped, pointed, self-introducing, and combinations thereof. Also, the devices may include, but are not limited to, metallic material, polymeric material, ceramic material, composite material, body tissue, synthetic tissue, hydrophilic material, expandable material, compressible material, heat bondable material, and combinations thereof.

The methods and devices disclosed in the '857 document may be used in conjunction with any surgical procedure of the body. The fastening and repair of tissue or an implant may be performed in connection with surgery of a joint, bone, muscle, ligament, tendon, cartilage, capsule, organ, skin, nerve, vessel, or other body parts. For example, tissue may be repaired during intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, shoulder surgery, hernia repair surgery, and surgery of an intrasubstance ligament tear, annulus fibrosis, fascia lata, flexor tendons, etc.

It is contemplated that the devices and methods of the present invention be applied using minimally invasive incisions and techniques to fasten muscles, tendons, ligaments, bones, nerves, and blood vessels. A small incision(s) may be made adjacent the damaged tissue area to be repaired, and a tube, delivery catheter, sheath, cannula, or expandable cannula may be used to perform the methods of the present invention. U.S. Pat. No. 5,320,611 entitled "Expandable Cannula Having Longitudinal Wire and Method of Use" discloses cannulas for surgical and medical use expandable along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

U.S. Pat. Nos. 5,674,240; 5,961,499; and 6,338,730 also disclose cannulas for surgical and medical use expandable along their lengths. The cannula can be provided with a pointed end portion and can include wires having cores which are enclosed by jackets. The jackets are integrally formed as one piece with a sheath of the cannula. The cannula may be expanded by inserting members or by fluid pressure. An expandable chamber may be provided at the distal end of the cannula. The above mentioned patents are hereby incorporated by reference.

In addition to using a cannula with the present invention, an introducer may be utilized to position implants at a specific location within the body. U.S. Pat. No. 5,948,002 entitled "Apparatus and Method for Use in Positioning a Suture Anchor" discloses devices for controlling the placement depth of a fastener. Also, U.S. patent application Ser. No. 10/102,413 discloses methods of securing body tissue with a robotic mechanism. The above-mentioned patent and application are hereby incorporated by reference. Another introducer or cannula which may be used with the present invention is the VersaStep® System by Tyco® Healthcare.

The present invention may also be utilized with minimally invasive surgery techniques disclosed in U.S. patent application Ser. No. 10/191,751 and U.S. Pat. Nos. 6,702,821 and 6,770,078. These patent documents disclose, inter alia, apparatus and methods for minimally invasive joint replacement. The femoral, tibial, and/or patellar components of a knee replacement may be fastened or locked to each other and to adjacent tissue using fixation devices disclosed herein and incorporated by reference. Furthermore, the methods and devices of the present invention may be utilized for repairing, reconstructing, augmenting, and securing tissue or implants during and "on the way out" of a knee replacement procedure. For example, the anterior cruciate ligament and other ligaments may be repaired or reconstructed; quadriceps mechanisms and other muscles may be repaired; a damaged rotator cuff may be mended. The patent documents mentioned above are hereby incorporated by reference.

Furthermore, it is contemplated that the present invention may be used with bariatric surgery, colorectal surgery, plastic surgery, gastroesophageal reflex disease (GERD) surgery, or for repairing hernias. A band, mesh, or cage of synthetic material or body tissue may be placed around an intestine or other tubular body member. The band may seal the intestine. This method may be performed over a balloon or bladder so that anastomosis is maintained. The inner diameter of the tubular body part is maintained by the balloon. The outer diameter of the body part is then closed or wrapped with a band, mesh, or patch. The inner diameter of the tubular body member may be narrowed or restricted by the band. The band may be secured to the tubular body part or surrounding tissue with the devices and methods described herein and incorporated by reference.

It is further contemplated that the present invention may be used in conjunction with the devices and methods disclosed in U.S. Pat. No. 5,329,846 entitled "Tissue Press and System" and U.S. Pat. No. 5,269,785 entitled "Apparatus and Method for Tissue Removal." For example, an implant secured within the body using the present invention may include tissue harvested, configured, and implanted as described in the patents. The above-mentioned patents are hereby incorporated by reference.

Additionally, it is contemplated that the devices and methods of the present invention may be used with heat bondable materials as disclosed in U.S. Pat. No. 5,593,425 entitled "Surgical Devices Assembled Using Heat Bondable Materials." For example, the implants of the present invention may include heat bondable material. The material may be deformed to secure tissue or hold a suture or cable. The fasteners made of heat bondable material may be mechanically crimped, plastically crimped, or may be welded to a suture or cable with RF (Bovie devices), laser, ultrasound, electromagnet, ultraviolet, infrared, electro-shockwave, or other known energy. The welding may be performed in an aqueous, dry, or moist environment. The welding device may be disposable, sterilizable, single-use, and/or battery-operated. The above-mentioned patent is hereby incorporated by reference.

Furthermore, the methods of the present invention may be performed under indirect visualization, such as endoscopic guidance, computer assisted navigation, magnetic resonance imaging, CT scan, ultrasound, fluoroscopy, X-ray, or other suitable visualization technique. The implants, fasteners, fastener assemblies, and sutures of the present invention may include a radiopaque material for enhancing indirect visualization. The use of these visualization means along with minimally invasive surgery techniques permits physicians to accurately and rapidly repair, reconstruct, augment, and secure tissue or an implant within the body. U.S. Pat. Nos. 5,329,924; 5,349,956; and 5,542,423 disclose apparatus and methods for use in medical imaging. Also, the present invention may be performed using robotics, such as haptic arms or similar apparatus. The above-mentioned patents are hereby incorporated by reference.

Moreover, the devices and methods of the present invention may be used for the repair and reconstruction of a tubular pathway like a blood vessel, intestine, urinary tract, esophagus, or other similar body parts. For example, a blood vessel may be intentionally severed during a surgical operation, or the blood vessel may be damaged or torn as a result of an injury. Flexible fixation of the vessel would permit the vessel to function properly and also compress and stabilize the vessel for enhanced healing. To facilitate the repair or reconstruction of a body lumen, a balloon may be inserted into the lumen and expanded so the damaged, severed, or torn portion of the vessel is positioned against the outer surface of the inflated balloon. In this configuration, the implants and methods described and incorporated herein may be used to approximate the damaged portion of the vessel.

All references cited herein are expressly incorporated by reference in their entirety.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

What is claimed is:

1. A fracture repair device comprising:
a plate having at least one hole, the hole having a bonding surface comprised of a polymeric material, wherein the plate is positionable on the surface of a bone;
a fastener configured to secure the plate to the bone, the fastener comprised of a shaft and a head, the shaft configured to pass through the hole in the plate and secure the fastener to the bone, wherein the head is configured to be coupled to the plate, the fastener head having a bonding surface comprised of polymeric material, wherein the bonding surface of the fastener head is configured to be positioned against the bonding surface of the plate hole and coupled to the bonding surface of the plate hole by application of energy, the coupling occurring at a coupling location between bonding surface of the fastener head and the bonding surface of the plate hole;
an effector configured to apply the energy; and
at least one sensor associated with the effector and operative to indicate at least one of pressure applied to and position of at least one of the fastener and the bonding surface of the plate hole during the application of energy,
wherein after the energy is applied, the fastener shaft is free of any thermal modification from the applied energy.

2. The device of claim 1 wherein the head of the fastener is at least one of (i) threaded and configured for insertion into a threaded hole in the plate and (ii) unthreaded and configured for insertion into and unthreaded hole in the plate.

3. The device of claim 1 wherein the plate and the fastener are biodegradable.

4. The device of claim 1 wherein the applied energy by which the bonding surface of the fastener is coupled to the bonding surface of the plate hole is at least one of resistive heating, radiofrequency, ultrasound, microwave, laser, electromagnetic, electro shockwave, and plasma.

5. The device of claim 1 wherein the polymeric material of the bonding surface of the plate hole and the polymeric material of the bonding surface of the fastener head are comprised of PEEK.

6. The device of claim 1 wherein the sensor associated with the effector and operative to indicate position is at least one of a linear variable displacement transducer (LVDT) and a hall-effect sensor.

7. The device of claim 1 wherein at least one of the plate, fastener, and effector is configured to pass through at least one of a fixed cannula and an expandable cannula.

8. The device of claim 1 wherein the at least one sensor associated with the effector is configured to be operative to indicate a change in shape of the fastener during the application of energy, whereby the application of energy is changed based on a change in shape of the fastener indicated by the sensor.

9. The device of claim 1 wherein the at least one sensor associated with the effector is configured to be operative to communicate feedback to vary, start, and stop the application of energy.

10. The device of claim 1 wherein the effector is configured to be controlled with a robotic mechanism.

11. The device of claim 1 wherein the fastener comprises a metallic core enclosed by a polymeric material.

\* \* \* \* \*